United States Patent
Dumas

(10) Patent No.: US 8,242,279 B2
(45) Date of Patent: Aug. 14, 2012

(54) PROCESS FOR PREPARING 2-AMINO-5-CYANOBENZOIC ACID DERIVATIVES

(75) Inventor: Donald J. Dumas, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 109 days.

(21) Appl. No.: 12/920,401

(22) PCT Filed: Mar. 4, 2009

(86) PCT No.: PCT/US2009/036012
§ 371 (c)(1), (2), (4) Date: Aug. 31, 2010

(87) PCT Pub. No.: WO2009/111553
PCT Pub. Date: Sep. 11, 2009

(65) Prior Publication Data
US 2011/0003998 A1    Jan. 6, 2011

Related U.S. Application Data

(60) Provisional application No. 61/068,297, filed on Mar. 5, 2008.

(51) Int. Cl.
*C07D 401/00* (2006.01)
(52) U.S. Cl. .................................................. 546/275.4
(58) Field of Classification Search .................. None
See application file for complete search history.

(56) References Cited

U.S. PATENT DOCUMENTS
7,592,452 B2    9/2009    Muller et al.

FOREIGN PATENT DOCUMENTS

| EP | 1903030 A | 3/2008 |
|---|---|---|
| WO | 2004/013094 A1 | 2/2004 |
| WO | 2004/067528 A1 | 8/2004 |
| WO | 2006/062978 A1 | 6/2006 |
| WO | 2006/068669 A1 | 6/2006 |
| WO | WO 2006068669 A1 * | 6/2006 |
| WO | 2008/082502 A1 | 7/2008 |
| WO | 2009/085816 A1 | 7/2009 |

OTHER PUBLICATIONS

Schareina, T. et al, Chem Eur J 2007 vol. 13, pp. 6249-6254.*
T. Schareina et al., "A State-of-the-Art Cyanation of Aryl Bromides: A Novel and Versatile Copper Catalyst System Inspired by Nature", Chem. Eur. J. 2007, vol. 13, pp. 6249-6254.
T. Schareina et al., "Copper-Catalyzed Cyanation of Heteroaryl Bromides: A Novel and Versatile Catalyst System Inspired by Nature", Synlett 2007, pp. 555-558.
J. Zanon et al., "Copper-Catalyzed Domino Halide Exchange-Cyanation of Aryl Bromides", *J. Am. Chem. Soc.* 2003, vol. 125, pp. 2890-2891.

T. Schareina et al., "A Bio-inspired Copper Catalyst System for Practical Catalytic Cyanation of Aryl Bromides", *Synthesis* 2008, pp. 3351-3355.

* cited by examiner

*Primary Examiner* — Janet Andres
*Assistant Examiner* — Heidi Reese
(74) *Attorney, Agent, or Firm* — Renee M. Lett

(57) ABSTRACT

Disclosed is a method for preparing a compound of Formula 1 comprising contacting a compound of Formula 2 with a metal cyanide reagent, a copper(I) salt reagent, an iodide salt reagent and at least one compound of Formula 3

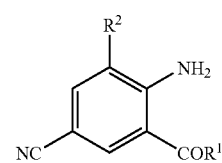

1

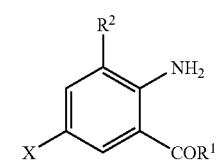

2

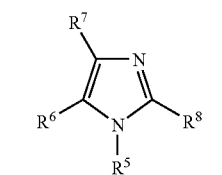

3 wherein $R^1$ is $NHR^3$ or $OR^4$; $R^2$ is $CH_3$ or Cl; $R^3$ is H, $C_1$-$C_4$ alkyl, cyclopropyl, cyclopropylcyclopropyl, cyclopropylmethyl or methylcyclopropyl; $R^4$ is H or $C_1$-$C_4$ alkyl; X is Br or Cl; and $R^5$, $R^6$, $R^7$ and $R^8$ are as defined in the disclosure.
Also disclosed is a method for preparing a compound of Formula 4 wherein $R^{11}$, $R^{12}$, $R^{13}$ and Z are as defined in the disclosure, using a compound of Formula 1 characterized by preparing the compound of Formula 1 by the method disclosed above or using a compound of Formula 1 prepared by the method disclosed above.

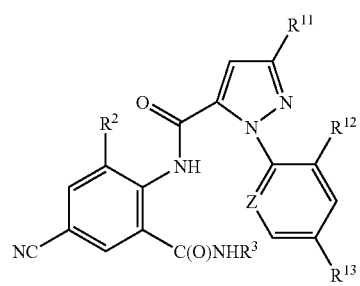

4

14 Claims, No Drawings

PROCESS FOR PREPARING 2-AMINO-5-CYANOBENZOIC ACID DERIVATIVES

FIELD OF THE INVENTION

The present invention pertains to a method for the preparation of 3-substituted 2-amino-5-cyanobenzoic acids and derivatives.

BACKGROUND OF THE INVENTION

Preparation of certain 2-amino-5-cyanobenzoic acids and their utility as intermediates for preparing corresponding insecticidal cyanoanthranilic diamides has been disclosed (see e.g., Scheme 9 in PCT Patent Publication WO 2004/067528; Scheme 9 and Example 2, Step A in PCT Patent Publication WO 2006/068669; and Scheme 15 and Example 6, Step B in PCT Patent Publication WO 2006/062978).

However, the need continues for new or improved methods suitable for rapidly and economically providing 2-amino-5-cyanobenzoic acids and derivatives.

SUMMARY OF THE INVENTION

The present invention is directed to a ethod for preparing a compound of Formula 1

1 wherein
  $R^1$ is $NHR^3$ or $OR^4$;
  $R^2$ is $CH_3$ or Cl;
  $R^3$ is H, $C_1$-$C_4$ alkyl, cyclopropyl, cyclopropylcyclopropyl, cyclopropylmethyl or methylcyclopropyl; and
  $R^4$ is H or $C_1$-$C_4$ alkyl;
comprising contacting (1) a compound of Formula 2

2 wherein X is Br or Cl;
with (2) a metal cyanide reagent, (3) a copper(I) salt reagent, (4) an iodide salt reagent and (5) at least one compound of Formula 3

3 wherein
  $R^5$ is H, phenyl or benzyl; or $C_1$-$C_{12}$ alkyl optionally substituted with $NR^9R^{10}$;
  each $R^6$, $R^7$ and $R^8$ is independently H, $C_1$-$C_{12}$ alkyl, phenyl or benzyl; or
  $R^6$ and $R^7$ are taken together as —CH=CH—CH=CH—; and
  $R^9$ and $R^{10}$ are taken together as —CH=N—CH=CH— optionally substituted with up to 3 substituents independently selected from $C_1$-$C_{12}$ alkyl;
provided that when X is Cl, then $R^2$ is methyl.

This invention also provides a method for preparing a compound of Formula 4

4 wherein
  $R^2$ is $CH_3$ or Cl;
  $R^3$ is H, $C_1$-$C_4$ alkyl, cyclopropyl, cyclopropylcyclopropyl, cyclopropylmethyl or methylcyclopropyl;
  Z is $CR^{14}$ or N;
  $R^{11}$ is Cl, Br, $CF_3$, $OCF_2H$ or $OCH_2CF_3$;
  $R^{12}$ is F, Cl or Br;
  $R^{13}$ is H, F or Cl; and
  $R^{14}$ is H, F, Cl or Br;
using a compound of Formula 1. The method is characterized by (a) preparing the compound of Formula 1 from the compound of Formula 2 by the method disclosed above, or (b) using as said compound of Formula 1 a compound of Formula 1 prepared by the method disclosed above.

DETAILS OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, the following definitions shall apply unless otherwise indicated. The term "optionally substituted" is used interchangeably with the phrase "substituted or unsubstituted" or with the term "(un)substituted." Unless otherwise indicated, when more than one substituent is present on a group each substitution is independent of the other. Also, a group stated to be optionally substituted with a substituent is substituted with zero or one instance of said substituent unless a higher limit is indicated.

In some instances herein ratios are recited as single numbers, which are relative to the number 1; for example, a ratio of 4 means 4:1.

As used herein, the term "cyanide equivalent" and related terms such as "cyanide equivalent ratio" when referring to a compound comprising one or more cyanide groups, refers to the number of cyanide ions ($CN^-$) per mole of the cyanide-containing compound. In particular, "cyanide equivalent(s)" denotes the number of moles of cyanide ion capable of being provided by a mole of the cyanide-containing compound (i.e. source of cyanide) for conversion of a compound of Formula 2 to a compound of Formula 1 according to the present method. For example, a hexacyanoferrate(II) reagent has six moles of cyanide ions per mole of hexacyanoferrate(II); therefore, if the cyanide equivalent ratio of a hexacyanoferrate(II) reagent relative to another reagent (e.g., compound of Formula 2) is 1:1, then the mole ratio would be 0.167:1. Furthermore, the method of the present invention involves the use of reagent (2) (i.e. a metal cyanide reagent), which can comprise one or more cyanide-containing compounds (e.g., one or more metal cyanides). In cases where reagent (2) comprises more than one cyanide-containing compound, the "cyanide equivalents" provided by reagent (2) is the sum of the number of equivalents of cyanide (i.e. moles of $CN^-$) provided by each of the cyanide-containing compounds in reagent (2). For example, for a particular reaction, reagent (2) might consist of a combination of sodium cyanide (NaCN) and copper(I) cyanide (CuCN); therefore the cyanide equivalent ratio relative to another reagent (e.g., a compound of Formula 2) is the sum of the number of cyanide equivalents provided by sodium cyanide and copper(I) cyanide relative to the number of moles of the other reagent. As both sodium cyanide and copper(I) cyanide contain one mole of cyanide ion per mole (i.e. formula weight) of compound, the cyanide equivalent ratio relative to another reagent is also the sum of the number of moles of sodium cyanide and copper(I) cyanide relative to the number of moles of the other reagent.

In the above recitations, the term "alkyl" includes straight-chain or branched alkyl, such as, methyl, ethyl, n-propyl, i-propyl, or the different butyl, pentyl or hexyl isomers.

The term "cyclopropylcyclopropyl," denotes cyclopropyl substitution on another cyclopropyl ring. Examples of "cyclopropylcyclopropyl," include 1,1'-bicyclopropyl-1-yl, 1,1'-bicyclopropyl-2-yl and the different cis- and trans-cyclopropylcyclopropyl isomers such as (1R,2S)-1,1'-bicyclopropyl-2-yl and (1R,2R)-1,1'-bicyclopropyl-2-yl.

As used herein, the term "ligand" refers to an organic molecule comprising at least one pair of electrons available for coordination with a metal atom (in this case a copper atom). The term "bidentate ligand" refers to an organic molecule comprising at least two electron pairs that are available for coordination with a metal atom (e.g., copper atom).

Carbon-based radical refers to a monovalent molecular component comprising a carbon atom that connects the radical to the remainder of the chemical structure through a single bond. Carbon-based radicals can optionally comprise saturated, unsaturated and aromatic groups, chains, rings and ring systems, and heteroatoms. Although carbon-based radicals are not subject to any particular limit in size, in the context of the present invention they typically comprise 1 to 16 carbon atoms and 0 to 3 heteroatoms. Of note are carbon-based radicals selected from $C_1$-$C_4$ alkyl, $C_1$-$C_2$ haloalkyl and phenyl optionally substituted with 1-3 substituents selected from $C_1$-$C_3$ alkyl, halogen and nitro.

The method of the present invention involves reagent (2) (i.e. a metal cyanide reagent), reagent (3) (i.e. a copper(I) salt reagent), and reagent (4) (i.e. an iodide salt reagent). Reagent (2) is alternatively and equivalently described as at least one metal cyanide, because a metal cyanide reagent contains one or more metal cyanides. Reagent (3) is alternatively and equivalently described as at least one copper(I) salt, because a copper(I) salt reagent contains one or more copper(I) salts. Reagent (4) is alternatively and equivalently described as at least one iodide salt, because an iodide salt reagent contains one or more iodide salts. Furthermore the number of moles of a metal cyanide reagent refers to the number of moles of cyanide contained in the reagent (as described above). The number of moles of a copper(I) salt reagent refers to the number of moles of copper(I) contained in the reagent. The number of moles of an iodide salt reagent refers to the number of moles of iodide contained in the reagent.

As referred to in the present disclosure, the term "carboxylic acid" means an organic chemical compound comprising at least one carboxylic acid functional group (i.e. —C(O)OH). The term "carboxylic acid" does not include the compound carbonic acid (i.e. HOC(O)OH). Carboxylic acids include, for example, formic acid, acetic acid, propionic acid, chloroacetic acid, benzoic acid, maleic acid, and citric acid. The term "effective $pK_a$" refers to the $pK_a$ of the carboxylic acid functional group, or if the compound has more than one carboxylic acid functional group, "effective $pK_a$" refers to the $pK_a$ of the most acidic carboxylic acid functional group. As referred to herein, the "effective pH" of a nonaqueous substance or mixture, such as a reaction mixture, is determined by mixing an aliquot of the substance or mixture with about 5 to 20 volumes of water and then measuring the pH of the resulting aqueous mixture (e.g., with a pH meter). As referred to herein, a "substantially anhydrous" substance means the substance contains no more than about 1% water by weight. The chemical name "isatoic anhydride" is another name corresponding to the current Chemical Abstracts name "2H-3,1-benzoxazine-2,4(1H)-dione".

Embodiments of the present invention include:

Embodiment A1

The method described in the Summary of the Invention for preparing a compound of Formula 1 comprising contacting reagent (1) (i.e. a compound of Formula 2) with reagent (2) (i.e. a metal cyanide reagent), reagent (3) (i.e. a copper(I) salt reagent), reagent (4) (i.e. an iodide salt reagent) and reagent (5) (i.e. at least one compound of Formula 3).

Embodiment A2

The method of Embodiment A1 wherein $R^1$ is $NHR^3$.

Embodiment A3

The method of Embodiment A1 or A2 wherein $R^3$ is $C_1$-$C_4$ alkyl, cyclopropyl, cyclopropylcyclopropyl, cyclopropylmethyl or methylcyclopropyl.

Embodiment A4

The method of Embodiment A3 wherein $R^3$ is $C_1$-$C_4$ alkyl or cyclopropylmethyl.

Embodiment A5

The method of Embodiment A4 wherein $R^3$ is methyl.

Embodiment A6

The method of any one of Embodiments A1 through A5 wherein $R^2$ is methyl.

Embodiment A7

The method of any one of Embodiments A1 through A6 wherein X is Br.

Embodiment A8

The method of any one of Embodiments A1 through A7 wherein reagent (1) comprises 2-amino-5-bromo-N,3-dimethylbenzamide.

Embodiment A9

The method of any one of Embodiments A1 through A8 wherein reagent (2) comprises one or more metal cyanides selected from the group consisting of alkali metal cyanides, alkali metal hexacyanoferrates(II) and copper(I) cyanide.

Embodiment A10

The method of Embodiment A9 wherein reagent (2) comprises one or more metal cyanides selected from the group consisting of alkali metal cyanides and alkali metal hexacyanoferrates(II).

Embodiment A11

The method of Embodiment A10 wherein reagent (2) comprises one or more metal cyanides selected from the group consisting of sodium cyanide, potassium cyanide, potassium hexacyanoferrate(II) and sodium hexacyanoferrate(II).

Embodiment A12

The method of Embodiment A11 wherein reagent (2) comprises one or more metal cyanides selected from the group consisting of sodium cyanide, potassium cyanide and potassium hexacyanoferrate(II).

Embodiment A13

The method of Embodiment A12 wherein reagent (2) comprises sodium cyanide or potassium hexacyanoferrate(II).

Embodiment A14

The method of Embodiment A13 wherein reagent (2) comprises sodium cyanide.

Embodiment A15

The method of any one of Embodiments A1 through A14 wherein the cyanide equivalent ratio of reagent (2) to reagent (1) is at least about 1.

Embodiment A16

The method of Embodiment A15 wherein the cyanide equivalent ratio of reagent (2) to reagent (1) is at least about 1.15.

Embodiment A17

The method of Embodiment A16 wherein the cyanide equivalent ratio of reagent (2) to reagent (1) is at least about 1.25.

Embodiment A17a

The method of Embodiment A17 wherein the cyanide equivalent ratio of reagent (2) to reagent (1) is at least about 1.4.

Embodiment A18

The method of any one of Embodiments A1 through A17a wherein the cyanide equivalent ratio of reagent (2) to reagent (1) is not larger than about 2.1.

Embodiment A19

The method of Embodiment A19 wherein the cyanide equivalent ratio of reagent (2) to reagent (1) is not larger than about 1.55.

Embodiment A19a

The method of Embodiment A19 wherein the cyanide equivalent ratio of reagent (2) to reagent (1) is not larger than about 1.5.

Embodiment A20

The method of Embodiment A19a wherein the cyanide equivalent ratio of reagent (2) to reagent (1) is not larger than about 1.4.

Embodiment A21

The method of any one of Embodiments A1 through A20 wherein $R^5$ is H; or $C_1$-$C_6$ alkyl optionally substituted with $NR^9R^{10}$.

Embodiment A22

The method of Embodiment 21 wherein $R^5$ is H, methyl, ethyl, n-propyl or n-butyl; or $C_1$-$C_6$ alkyl substituted with $NR^9R^{10}$.

Embodiment A23

The method of Embodiment A22 wherein $R^5$ is methyl or n-butyl.

Embodiment A24

The method of any of one Embodiments A1 through A22 wherein $R^9$ and $R^{10}$ are taken together as —CH=N—CH=CH—.

Embodiment A25

The method of any one of Embodiments A1 through A24 wherein each $R^6$, $R^7$ and $R^8$ when taken alone (i.e. $R^6$ and $R^7$ are not taken together) is independently H or $C_1$-$C_3$ alkyl.

Embodiment A26

The method of Embodiment A25 wherein each $R^6$, $R^7$ and $R^8$ when taken alone is independently H or methyl.

Embodiment A27

The method of Embodiment A26 wherein each $R^6$, $R^7$ and $R^8$ when taken alone is H.

Embodiment A27a

The method of any one of Embodiments A1 through A27 wherein each $R^6$, $R^7$ and $R^8$ are taken alone.

Embodiment A28

The method of any one of Embodiments A1 through A27a wherein reagent (5) comprises one or more compounds selected from the group consisting of 1-methyl-1H-imidazole, 1-ethyl-1H-imidazole, 1-propyl-1H-imidazole, 1-butyl-1H-imidazole, 1-pentyl-1H-imidazole, 1-hexyl-1H-imidazole, 4-methylimidazole, 1,1'-(1,4-butanediyl)bis-1H-imidazole, 1,1'-(1,5-pentanediyl)bis-1H-imidazole and 1,1'-(1,6-hexanediyl)bis-1H-imidazole.

Embodiment A28a

The method of Embodiment A28 wherein reagent (5) comprises one or more compounds selected from the group consisting of 1-methyl-1H-imidazole, 1-ethyl-1H-imidazole, 1-propyl-1H-imidazole, 1-butyl-1H-imidazole, 4-methylimidazole, 1,1'-(1,4-butanediyl)bis-1H-imidazole and 1,1'-(1,6-hexanediyl)bis-1H-imidazole.

Embodiment A28b

The method of Embodiment A28a wherein reagent (5) comprises one or more compounds selected from the group consisting of 1-methyl-1H-imidazole, 1-butyl-1H-imidazole, 4-methylimidazole and 1,1'-(1,6-hexanediyl)bis-1H-imidazole.

Embodiment A29

The method of any one of Embodiments A1 through A28b wherein reagent (5) comprises one or more compounds selected from the group consisting of 1-methyl-1H-imidazole, 1-ethyl-1H-imidazole, 1-propyl-1H-imidazole, 1-butyl-1H-imidazole, 1-pentyl-1H-imidazole, 1-hexyl-1H-imidazole, 1,1'-(1,4-butanediyl)bis-1H-imidazole, 1,1'-(1,5-pentanediyl)bis-1H-imidazole and 1,1'-(1,6-hexanediyl)bis-1H-imidazole.

Embodiment A30

The method of Embodiment A29 wherein reagent (5) comprises one or more compounds selected from the group consisting of 1-methyl-1H-imidazole, 1-ethyl-1H-imidazole, 1-butyl-1H-imidazole and 1,1'-(1,4-butanediyl)bis-1H-imidazole.

Embodiment A31

The method of Embodiment A28b or A30 wherein reagent (5) comprises 1-methyl-1H-imidazole or 1-butyl-1H-imidazole.

Embodiment A32

The method of Embodiment A31 wherein reagent (5) comprises 1-methyl-1H-imidazole.

Embodiment A33

The method of Embodiment A31 wherein reagent (5) comprises 1-butyl-1H-imidazole.

Embodiment A34

The method of any one of Embodiments A1 through A33 wherein the mole ratio of reagent (5) to reagent (3) (based on copper(I) content) is at least about 1.

Embodiment A34a

The method of Embodiment A34 wherein the mole ratio of reagent (5) to reagent (3) (based on copper(I) content) is at least about 1.5.

Embodiment A35

The method of Embodiment A34a wherein the mole ratio of reagent (5) to reagent (3) is at least about 2.

Embodiment A36

The method of Embodiment A35 wherein the mole ratio of reagent (5) to reagent (3) is at least about 2.5.

Embodiment A37

The method of Embodiment A36 wherein the mole ratio of reagent (5) to reagent (3) is at least about 3.

Embodiment A38

The method of Embodiment A37 wherein the mole ratio of reagent (5) to reagent (3) is at least about 4.

Embodiment A39

The method of any one of Embodiments A1 through A38 wherein the mole ratio of reagent (5) to reagent (3) (based on copper(I) content) is not larger than about 10.

Embodiment A40

The method of Embodiment A39 wherein the mole ratio of reagent (5) to reagent (3) is not larger than about 6.

Embodiment A41

The method of Embodiment A40 wherein the mole ratio of reagent (5) to reagent (3) is not larger than about 5.5.

Embodiment A42

The method of Embodiment A41 wherein the mole ratio of reagent (5) to reagent (3) is not larger than about 5.

Embodiment A43

The method of any one of Embodiments A1 through A42 wherein the mole ratio of reagent (3) (based on copper(I) content) to reagent (1) is at least about 0.01.

Embodiment A44

The method of Embodiment A43 wherein the mole ratio of reagent (3) to reagent (1) is at least about 0.1.

Embodiment A45

The method of Embodiment A44 wherein the mole ratio of reagent (3) to reagent (1) is at least about 0.15.

Embodiment A45a

The method of Embodiment A45 wherein the mole ratio of reagent (3) to reagent (1) is at least about 0.3 when X is Cl.

Embodiment A46

The method of any one of Embodiments A1 through A45a wherein the mole ratio of reagent (3) (based on copper(I) content) to reagent (1) is less than about 1.

Embodiment A47

The method of any one of Embodiments A1 through A46 wherein the mole ratio of reagent (3) (based on copper(I) content) to reagent (1) is not larger than about 0.99.

Embodiment A48

The method of Embodiment A47 wherein the mole ratio of reagent (3) to reagent (1) is not larger than about 0.5.

Embodiment A49

The method of Embodiment A48 wherein the mole ratio of reagent (3) to reagent (1) is not larger than about 0.4.

Embodiment A50

The method of Embodiment A49 wherein the mole ratio of reagent (3) to reagent (1) is not larger than about 0.3.

Embodiment A51

The method of Embodiment A50 wherein the mole ratio of reagent (3) to reagent (1) is not larger than about 0.25 when X is Br.

Embodiment A52

The method of Embodiment A51 wherein the mole ratio of reagent (3) to reagent (1) is not larger than about 0.2 when X is Br.

Embodiment A53

The method of any one of Embodiments A1 through A52 wherein the mole ratio of reagent (4) to reagent (1) is at least about 0.001.

Embodiment A54

The method of Embodiment A53 wherein the mole ratio of reagent (4) to reagent (1) is at least about 0.05.

Embodiment A55

The method of Embodiment A54 wherein the mole ratio of reagent (4) to reagent (1) is at least about 0.1.

Embodiment A56

The method of Embodiment A55 wherein the mole ratio of reagent (4) to reagent (1) is at least about 0.15.

Embodiment A57

The method of any one of Embodiments A1 through A56 wherein the mole ratio of reagent (4) to reagent (1) is less than about 1.

Embodiment A58

The method of any one of Embodiments A1 through A57 wherein the mole ratio of reagent (4) to reagent (1) is not larger than about 0.5.

Embodiment A59

The method of Embodiment A58 wherein the mole ratio of reagent (4) to reagent (1) is not larger than about 0.4.

Embodiment A60

The method of Embodiment A59 wherein the mole ratio of reagent (4) to reagent (1) is not larger than about 0.3.

Embodiment A61

The method of Embodiment 60 wherein the mole ratio of reagent (4) to reagent (1) is not larger than about 0.2.

Embodiment A62

The method of any one of Embodiments A1 through A61 wherein reagent (3) and reagent (4) comprise copper(I) iodide.

Embodiment A63

The method of any one of Embodiments A1 through A62 wherein reagent (1), reagent (2), reagent (3), reagent (4) and reagent (5) are contacted in a suitable organic solvent.

Embodiment A64

The method of any one of Embodiments A1 through A63 wherein reagent (1) is contacted with a suitable organic solvent to form a mixture, and then reagent (2), reagent (3), reagent (4) and reagent (5) are sequentially added to the mixture.

Embodiment A65

The method of any one of Embodiments A63 and A64 wherein the suitable organic solvent comprises one or more solvents selected from the group consisting of halogenated and nonhalogenated aliphatic and aromatic hydrocarbons.

Embodiment A66

The method of Embodiment A65 wherein the suitable organic solvent comprises one or more solvents selected from the group consisting of xylenes, toluene, chlorobenzene, methoxybenzene (also known as anisole), 1,2,4-trimethylbenzene, 1,3,5-trimethylbenzene (also known as mesitylene), ethylbenzene, (1-methylethyl)benzene (also known as cumene), $C_1$-$C_3$ alkyl-substituted naphthalenes (e.g., 1-methylnaphthalene, 2-methylnaphthalene, 1,5-dimethylnaphthalene, 2,6-dimethylnaphthalene and 1,3-dimethylnaphthalene), ShellSol A100 (mixture of $C_9$-$C_{10}$ aromatic hydrocarbons) and ShellSol A150 (mixture of $C_{10}$-$C_{11}$ aromatic hydrocarbons).

Embodiment A67

The method of Embodiment A66 wherein the suitable organic solvent comprises one or more solvents selected from the group consisting of xylenes, toluene, chlorobenzene, anisole, 1,2,4-trimethylbenzene, mesitylene, 1-methylnaphthalene, ShellSol A100 and ShellSol A150.

Embodiment A67a

The method of Embodiment A66 wherein the suitable organic solvent comprises one or more solvents selected from the group consisting of xylenes, toluene, 1,2,4-trimethylbenzene, mesitylene and 1-methylnaphthalene.

Embodiment A68

The method of Embodiment A67 or A67a wherein the suitable organic solvent comprises xylenes, toluene, 1-methylnaphthalene or mesitylene.

Embodiment A69

The method of Embodiment A68 wherein the suitable organic solvent comprises xylenes, toluene or mesitylene.

Embodiment A69a

The method of Embodiment A68 wherein the suitable organic solvent comprises 1-methylnaphthalene or mesitylene.

Embodiment A70

The method of Embodiment A69 wherein the suitable organic solvent comprises xylenes.

Embodiment A71

The method of Embodiment A69 wherein the suitable organic solvent comprises toluene.

Embodiment A72

The method of any one of Embodiments A69 and A69a wherein the suitable organic solvent comprises mesitylene.

Embodiment A73

The method of any one of Embodiments A63 through A72 wherein the ratio of the volume of the suitable organic solvent to the weight of reagent (1) is at least about 2 mL/g.

Embodiment A74

The method of Embodiment A73 wherein the ratio of the volume of the suitable organic solvent to the weight of reagent (1) is at least about 3 mL/g.

Embodiment A75

The method of Embodiment A74 wherein the ratio of the volume of the suitable organic solvent to the weight of reagent (1) is at least about 4 mL/g.

Embodiment A76

The method of any one of Embodiments A63 through A75 wherein the ratio of the volume of the suitable organic solvent to reagent (1) is not larger than about 10 mL/g.

Embodiment A77

The method of Embodiment A76 wherein the ratio of the volume of the suitable organic solvent to the weight of reagent (1) is not larger than about 6 mL/g.

Embodiment A78

The method of Embodiment A77 wherein the ratio of the volume of the suitable organic solvent to the weight of reagent (1) is not larger than about 5 mL/g.

Embodiment A79

The method of any one of Embodiments A1 through A78 wherein reagent (1), reagent (2), reagent (3), reagent (4) and reagent (5) are contacted in the presence of a suitable organic solvent to form a mixture, the pressure above the mixture is increased above atmospheric pressure and the temperature of the mixture is increased above the normal boiling point of the solvent (i.e. boiling point at 100 kPa or 14.5 psia pressure).

Embodiment A80

The method of Embodiment A79 wherein the suitable organic solvent comprises xylenes, toluene or anisole.

Embodiment A81a

The method of Embodiment A80 wherein the suitable organic solvent comprises xylenes or toluene.

Embodiment A82

The method of any one of Embodiments A1 through A81a wherein reagent (1), reagent (2), reagent (3), reagent (4) and reagent (5) are contacted with a suitable organic solvent at a temperature not greater than about 200° C.

Embodiment A83

The method of Embodiment A82 wherein reagent (1), reagent (2), reagent (3), reagent (4) and reagent (5) are contacted with a suitable organic solvent at a temperature not greater than about 180° C.

Embodiment A84

The method of Embodiment A83 wherein reagent (1), reagent (2), reagent (3), reagent (4) and reagent (5) are contacted with a suitable organic solvent at a temperature not greater than about 170° C.

Embodiment A85

The method of Embodiment A84 wherein reagent (1), reagent (2), reagent (3), reagent (4) and reagent (5) are contacted with a suitable organic solvent at a temperature not greater than about 165° C.

Embodiment A86

The method of any one of Embodiments A1 through A85 wherein reagent (1), reagent (2), reagent (3), reagent (4) and reagent (5) are contacted with a suitable organic solvent at a temperature greater than about 115° C.

Embodiment A87

The method of Embodiment A86 wherein reagent (1), reagent (2), reagent (3), reagent (4) and reagent (5) are contacted with a suitable organic solvent at a temperature greater than about 145° C.

Embodiment A88

The method of Embodiment A87 wherein reagent (1), reagent (2), reagent (3), reagent (4) and reagent (5) are contacted with a suitable organic solvent at a temperature greater than about 155° C.

Embodiment A89

The method of Embodiment A88 wherein reagent (1), reagent (2), reagent (3), reagent (4) and reagent (5) are contacted with a suitable organic solvent at a temperature greater than about 160° C.

Embodiment A90

The method of Embodiment A1 wherein X is Br and the compound of Formula 1 is prepared as a solid, comprising contacting reagent (1) with a suitable organic solvent to form a mixture, and then sequentially adding reagent (2), reagent (3), reagent (4) and reagent (5) to the mixture, maintaining the temperature of the mixture between about 145 and 180° C. for about 5 to about 8 h, cooling the mixture to between about 0 and 50° C., adding water to the mixture, optionally adding a copper-coordinating agent to the reaction mixture, optionally stirring for about 1 to about 24 h, and then recovering the compound of Formula 1 as a solid from the mixture.

Embodiment A91

The method of Embodiment A1 wherein X is Cl and the compound of Formula 1 is prepared as a solid, comprising contacting reagent (1) with a suitable organic solvent to form a mixture, and then sequentially adding reagent (2), reagent (3), reagent (4) and reagent (5) to the mixture, maintaining the temperature of the mixture between about 150 and 200° C. for about 5 to about 24 h, cooling the mixture to between about 0 and 50° C., adding water to the mixture, optionally adding a copper-coordinating agent to the reaction mixture, optionally stirring for about 1 to about 24 h, and then recovering the compound of Formula 1 as a solid from the mixture.

Embodiment B1

The method described in the Summary of the Invention for preparing a compound of Formula 4 using a compound of Formula 1 prepared from a compound of Formula 2.

Embodiment B2

The method of Embodiment B1 wherein the compound of Formula 1 is prepared from a compound of Formula 2 by the method of any one of Embodiments A1 through A91.

Embodiment B3

The method of Embodiment B1 or B2 wherein Z is N.

Embodiment B4

The method of Embodiment B1 or B2 wherein Z is CH.

Embodiment B5

The method of any one of Embodiments B1 through B4 wherein $R^3$ is $C_1$-$C_4$ alkyl, cyclopropyl, cyclopropylcyclopropyl, cyclopropylmethyl or methylcyclopropyl.

Embodiment B6

The method of Embodiment B5 wherein $R^3$ is $C_1$-$C_4$ alkyl or cyclopropylmethyl.

Embodiment B7

The method of Embodiment B6 wherein $R^3$ is methyl.

Embodiment B8

The method of any one of Embodiments B1 through B7 wherein $R^2$ is methyl.

Embodiment B9

The method of any one of Embodiments B1 through B8 wherein $R^{11}$ is Br.

Embodiment B10

The method of any one of Embodiments B1 through B9 wherein $R^{12}$ is Cl.

Embodiment B11. The method of any one of Embodiments B1 through B10 wherein $R^{13}$ is H.

Embodiment B12

The method of any one of Embodiments A1 through A91 or B1 through B11 wherein the compound of Formula 1 is 2-amino-5-cyano-N,3-dimethylbenzamide.

Embodiment C1

The method described in the Summary of the Invention or any one of Embodiments A1 through A91 or B1 through B12 wherein $R^5$ is H; or $C_1$-$C_{12}$ alkyl optionally substituted with $NR^9R^{10}$, unless a narrower definition is specified.

Embodiment C2

The method described in the Summary of the Invention or any one of Embodiments A1 through A91, B1 through B12 or C1 wherein each $R^6$, $R^7$ and $R^8$ is independently H or $C_1$-$C_{12}$ alkyl, unless a narrower definition is specified.

Embodiments of this invention can be combined in any manner. Of note is the method of any one of Embodiments A1-A90 or B1-B12 wherein X is Br. Also of note is the method of any one of Embodiments A1-A89, A91 or B1-B12 wherein X is Cl.

In the following Schemes 1-8 the definitions of $R^1$, $R^2$, $R^3$, $R^4$, $R^5$, $R^6$, $R^7$, $R^8$, $R^{11}$, $R^{12}$, $R^{13}$, X and Z in the compounds of Formulae 1 through 10 are as defined above in the Summary of the Invention and description of Embodiments unless otherwise indicated. Formulae 1a, 1b and 1c are subsets of Formula 1. Formula 2a is a subset of Formula 2.

As shown in Scheme 1, in a method of the present invention a compound of Formula 1 is prepared by contacting a compound of Formula 2 with at least one metal cyanide (i.e. a metal cyanide reagent), at least one copper(I) salt (i.e. a copper(I) salt reagent), at least one iodide salt (i.e. an iodide salt reagent) and at least one compound of Formula 3.

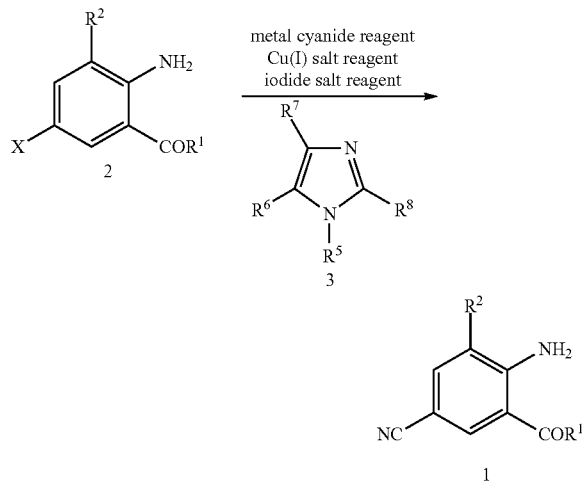

Scheme 1

In the present method the metal cyanide reagent particularly comprises at least one compound selected from the group consisting of alkali metal cyanides, alkali metal hexacyanoferrates(II) and copper(I) cyanide. Suitable alkali metal cyanides include compounds of the formula $M^1CN$ wherein $M^1$ is an alkali metal such as sodium or potassium. Suitable alkali metal hexacyanoferrates(II) include, for example, potassium hexacyanoferrate(II) and sodium hexacyanoferrate(II), both of which are commercially available at low cost, are non-toxic, easy to handle, and have six cyanide ions available for transfer to compounds of Formula 2. Highest yields of Formula 1 compounds are usually achieved when using a metal cyanide reagent comprising sodium cyanide. Typically the cyanide equivalent ratio of the metal cyanide reagent relative to the compound of Formula 2 is from about 1 to about 2.1, and more typically from about 1.15 to about 1.55. However, the use of larger amounts of the metal cyanide reagent can be advantageous for removing copper during isolation of the compound of Formula 1. Alkali metal cyanides such as sodium cyanide are particularly useful as copper-coordinating agents facilitating removal of copper during isolation of the compound of Formula 1. When additional amounts of a metal cyanide reagent comprising an alkali metal cyanide are included in the reaction mixture to facilitate later removal of copper, the equivalent ratio of metal cyanide reagent relative to the compound of Formula 2 typically is from about 1.4 to about 2.1 or even higher. When using an alkali metal cyanide it may be beneficial to reduce the particle size of the alkali metal cyanide by standard means, such as grinding or milling, before adding the alkyl metal cyanide to the reaction mixture. Typically an alkali metal cyanide that has been ground or milled is particularly advantageous when using only a stoichiometric amount or slightly more of the alkali metal cyanide. In contrast, when an alkali metal cyanide is used in large excess, such as an amount sufficient for not only the cyanation step but also later removal of copper from the reaction mixture (i.e. about 1.4 to 2.1 relative to Formula 2), grinding or milling the alkali metal cyanide may provide a negligible benefit compared to using the alkali metal cyanide not ground or milled before addition to the reaction mixture.

In the method of Scheme 1, the copper(I) salt reagent is believed to act as a source of a chemical species which catalyzes the conversion of Formula 2 compounds to Formula 1. Suitable copper(I) salt reagents comprise one or more compounds selected from the group consisting of copper(I) salts, such as copper(I) iodide, copper(I) bromide, copper(I) chloride, copper(I) cyanide and copper(I) triflate ($CuOSO_2CF_3$). The mole ratio of the copper(I) salt reagent (based on Cu(I)) to the compound of Formula 2 is from about 0.01 to about 1, and typically from about 0.01 to about 0.99, and more typically from about 0.1 to about 0.4. When X is Br, optimal results are typically obtained from mole ratios from about 0.1 to about 0.3 of the copper(I) salt reagent to the compound of Formula 2. Because compounds of Formula 2 wherein X is Cl are generally less reactive than corresponding compounds of Formula 2 in the reaction of Scheme 1, greater amounts of copper(I) are typically used to promote the reaction when X is Cl. Therefore when X is Cl, mole ratios from about 0.3 to about 0.4 of the copper(I) salt reagent to the compound of Formula 2 are typically used.

Without being bound by any particular theory, it is believed under the conditions of the present method a 5-bromo or chloro derivative of Formula 2 is at least partially converted to the corresponding 5-iodo derivative in the presence of an iodide salt. Suitable iodide salt reagents comprise one or more compounds selected from the group consisting of quaternary ammonium, alkali and alkaline earth metal iodide salts such as copper(I) iodide, sodium iodide, potassium iodide, zinc iodide, lithium iodide, calcium iodide, tetrabutylammonium iodide and tetramethylammonium iodide. The mole ratio of the iodide salt to the compound of Formula 2 is typically from about 0.001 to about 1, and more typically from about 0.05 to about 0.4, and most typically from about 0.1 to about 0.4.

In the method of Scheme 1 highest yields of Formula 1 compounds with optimal reaction rates are often obtained when copper(I) iodide (CuI) is used as the source of the copper(I) salt reagent and the iodide salt reagent. When copper(I) iodide (CuI) is used in the present method typically the mole ratio is from about 0.1 to about 0.4 relative to the compound of Formula 2. In some cases it can be beneficial to use copper(I) iodide in combination with another iodide salt reagent, such as sodium iodide, potassium iodide, zinc iodide, tetrabutylammonium iodide or tetramethylammonium iodide. The usefulness of combining copper(I) iodide with another iodide salt reagent depends on the specific reaction conditions and substrate. Typically optimal yields of Formula 1 compounds can be obtained from the present process simply by using copper(I) iodide as the only source of iodide salt reagent.

Compounds of Formula 3 act as ligands in the method of Scheme 1. Both monodentate chelating ligands comprising an optionally substituted imidazole ring and bidentate chelating ligands comprising 2 optionally substituted imidazole rings can be used. These ligands have been found to accelerate the rate of conversion of compounds of Formula 2 to Formula 1. Not being bound by any particular theory, it is believed these ligands facilitate the reaction by increasing the solubility, reactivity and/or stability of the active copper(I) catalytic species via the formation of a copper-ligand complex. Formula 3 compounds including imidazole and a wide variety of imidazole-substituted derivatives are useful as ligands in the present method. Typical ligands of Formula 3 include compounds wherein $R^5$, $R^6$, $R^7$ and $R^8$ are independently H or $C_1$-$C_4$ alkyl such as 1-methyl-1H-imidazole, 1-ethyl-1H-imidazole, 1-propyl-1H-imidazole, 1-butyl-1H-imidazole, 1-pentyl-1H-imidazole, 1-hexyl-1H-imidazole and 4-methylimidazole. Also useful are bis(imidazolyl)alkanes (i.e. wherein $R^5$ is $C_1$-$C_{12}$ alkyl substituted with $NR^9R^{10}$) such as 1,1'-(1,4-butanediyl)bis-1H-imidazole, 1,1'-(1,5-pentanediyl)bis-1H-imidazole and 1,1'-(1,6-hexanediyl)bis-1H-imidazole. In the method of Scheme 1 typically the highest yields of Formula 1 compounds and the most favorable reaction rates are achieved with the use of one or more of the following commercially available ligands: 1-methyl-1H-imidazole, 1-butyl-1H-imidazole, 4-methylimidazole and 1,1'-(1,6-hexanediyl)bis-1H-imidazole. The mole ratio of the compound or compounds of Formula 3 to the copper(I) salt reagent is typically from about 1 to about 10. As mole ratios greater than 1 can often accelerate the reaction while ratios above 6 generally offer little additional benefit while increasing cost, the ratio is preferably from about 1.5 to about 6.

The reaction of Scheme 1 is typically conducted in a suitable organic solvent. A variety of solvents can be used to form the suitable solvent for this method. Typically, the method is most satisfactorily conducted using solvents in which compounds of Formula 2 are preferably completely or at least substantially soluble and the metal cyanide reagent has a low solubility in the volume of solvents used and at the reaction temperatures. Examples of suitable solvents include halogenated and nonhalogenated aliphatic and aromatic hydrocarbons such as xylenes, toluene, chlorobenzene, methoxybenzene (also known as anisole), 1,2,4-trimethylbenzene, 1,3,5-trimethylbenzene (also known as mesitylene), ethylbenzene, (1-methylethyl)benzene (also known as cumene), $C_1$-$C_3$ alkyl-substituted naphthalenes (e.g., 1-methylnaphthalene, 2-methylnaphthalene, 1,5-dimethylnaphthalene, 2,6-dimethylnaphthalene and 1,3-dimethylnaphthalene) and aromatic solvent mixtures which are sold, for example, by Shell Chemical under the trade name ShellSol, in particular ShellSol A100 (mixture of $C_9$-$C_{10}$ aromatic hydrocarbons) and ShellSol A150 (mixture of $C_{10}$-$C_{11}$ aromatic hydrocarbons), including mixtures of the foregoing solvents. The method is most satisfactorily conducted using a solvent that allows for reaction temperatures between about 150 and 180° C. This can be accomplished by using a solvent with a normal boiling point (i.e. boiling point at 100 kPa pressure) within or above this range or by operating at elevated pressure with a lower boiling solvent such as xylenes or toluene. The solvents xylenes or toluene are useful solvents, as high yields of Formula 1 compounds are typically obtained using these solvents, particularly when the present method is conducted at elevated pressure. When using xylenes as a solvent a single isomer (i.e. o-xylene, m-xylene or p-xylene) can be used, but use of the isomeric mixture of xylenes is commercially preferable as it provides equally good results at lower cost. The method is also conveniently conducted using a solvent with a normal boiling point in the range of about 150 and 180° C. such as 1,3,5-trimethylbenzene, 1-methylnaphthalene, $C_9$-$C_{11}$ aromatic solvent mixtures, or mixtures thereof. In particular, the use of a solvent (i.e. with a normal boiling point boiling the range of about 150 and 180° C.) comprising 1-methylnaphthalene or 1,3,5-trimethylbenzene has been found to results in high yields of Formula 1 compounds. The volume of the organic solvent relative to the weight of the compound of Formula 2 is typically between about 2 mL/g and about 10 mL/g. Amounts of solvent greater than 2 mL/g can facilitate stirring the reaction mixture, but larger amounts of solvent can slow the reaction as well as increase cost; therefore typically the volume of solvent to the weight of the compound Formula 2 is between about 2 mL/g and about 5 mL/g, and more typically between about 2 mL/g and 4 mL/g. The solvent can be added in various ways and times during the course of the reaction, such as: in one batch at the start of the reaction sequence, or portionwise during the reaction sequence, or intermittently during the course of adding one or more reagents. For example, one or more reagents can be dispersed, dissolved or partially dissolved in the suitable organic solvent and then added to a mixture comprising the other reagents and an additional amount of the suitable organic solvent.

In the present method, the order in which the reactants are combined is not critical to the outcome of the reaction. One order of combination, for example, involves combining the compound of Formula 2 with the suitable organic solvent to form a mixture, and then sequentially adding the metal cyanide reagent, the copper(I) salt reagent, the iodide salt reagent and at the least one compound of Formula 3 to the mixture. Alternatively, in some cases it is advantageous to dissolve the at least one compound of Formula 3 and the copper(I) salt reagent in the suitable organic solvent and add this solution to a mixture comprising the compound of Formula 2, metal cyanide reagent, iodide salt reagent and suitable organic solvent. Or, alternatively, the at least one compound of Formula 3 can be dissolved in the suitable organic solvent and added to a mixture comprising the compound of Formula 2, metal cyanide reagent, copper(I) salt reagent, iodide salt reagent and the suitable organic solvent. For these modes of addition, typically the suitable organic solvent (i.e. solvent compound or mixture of solvent compounds) used to dissolve the compound(s) of Formula 3 and the copper(I) salt reagent is the same suitable organic solvent used to form the mixture comprising the reaction components. A variety of other orders of addition are also useful for the present method.

The method of Scheme 1 is preferably conducted in an oxygen-free environment, although not essential for the successful outcome of the reaction. Reducing the presence of atmospheric oxygen in the reaction vessel prior to and during the addition of the reagents and maintaining an oxygen-free environment during the course of the reaction has been found to be advantageous. Standard techniques for obtaining an oxygen-free environment can be used including, for example, evacuating the reaction vessel using a vacuum pump and then repressurizing to atmospheric pressure with an inert gas (e.g., nitrogen or argon). This method can be repeated two or more times to further reduce the oxygen present in the reaction vessel. Alternatively, the reaction vessel can be purged with an inert gas and then a positive pressure of inert gas can be maintained throughout the reaction.

The present method is typically conducted at temperatures between about 115 and 200° C. and more typically between about 145 and 200° C. Temperatures between about 150 and 180° C. often achieve the highest product yield and purity with the most favorable reaction rates; for example, in most cases compounds of Formula 1 are obtained in yields of 95% or greater in about 5 to about 8 h.

The product of Formula 1 can be isolated by standard techniques known in the art, including filtration, extraction, evaporation and crystallization. For example, the reaction medium can be diluted with about 2 to 8 parts by weight of water relative to the compound of Formula 2 to dissolve inorganic salts that are present in the reaction medium. As the compounds of Formula 1 are typically solids at ambient temperature and generally sparingly soluble in the reaction solvent, they are most easily isolated by filtration, followed by washing with water and optionally an organic solvent (e.g., xylenes, toluene, 1,3,5-trimethylbenzene). If the compounds of Formula 1 are soluble in the reaction solvent, they are most conveniently isolated by diluting the reaction medium with water to dissolve inorganic salts, then separating the organic phase, optionally followed by washing with water, to remove residual amounts of salts and/or metal cyanides, and then removing the solvent by distillation or evaporation at reduced pressure. In some cases it can be advantageous to add a water-soluble copper-coordinating agent to optimize the removal of copper prior to isolating compounds of Formula 1. Useful copper-coordinating agents include, for example, 2,2'-thiodiethanol, ethylenediamine, N,N-dimethylethylenediamine, N,N,N',N'-tetramethylethylenediamine and alkali metal cyanides. Particularly useful for the removal of copper is ethylenediamine and alkali metal cyanides. If an alkali metal cyanide (e.g., sodium cyanide) is used in the present method as a copper-coordinating agent typically about 0.3 to about 0.6 moles relative to the compounds of Formula 2 is useful for reducing the amount of residual copper in compounds of Formula 1. This amount of sodium cyanide can be added when the metal cyanide reagent is added (i.e. during the cyanation reaction as discussed above) or at the completion of the reaction and prior to isolating compounds of Formula 1. For the first mode of addition the alkali metal cyanide is added in anhydrous form, and for the second it is added either in anhydrous form or as an aqueous solution. Compounds of Formula 1 can be further purified by recrystallization from an appropriate organic solvent. Examples of appropriate solvents include methanol, ethanol, i-propanol, n-propanol, toluene, xylenes and chlorobenzene. The method of Scheme 1 is illustrated in Examples 1-21 below. Examples 3 and 4 illustrate the method of Scheme 1 including the treatment of the reaction mixture with ethylenediamine prior to isolation of the compound of Formula 1.

The features of the present method provide an efficient means using inexpensive reagents to produce 3-substituted 2-amino-5-cyanobenzoic acid derivatives of Formula 1 in high yields (typically 95% or greater based on the moles of Formula 2 compound used) in about 5 to about 8 h. Of particular note is that the present method can be used to provide remarkably high yields of the compounds of Formula 1 in excellent purity even though these compounds as well as the starting compounds of Formula 2 contain amino substituents and in some cases amide substituents that can potentially participate in side reactions.

Starting compounds of Formula 2 can be made by a variety of methods known in the art. As shown in Scheme 2, according to one method compounds of Formula 2 are prepared by halogenation of a compound of Formula 5 using a variety of reagents known in the literature including bromine, chlorine, sulfuryl chloride, N-chlorosuccinimide (NCS), N-bromosuccinimide (NBS) and halogenating reagents such as mixtures comprising hydrogen peroxide and hydrogen halide. For leading references describing these methods, see PCT Patent Publications WO 1998/16503 (Scheme 4 and Example 132), WO 2006/068669 (Scheme 11), WO 2003/015519 (Scheme 4 and Example 1, Step A) and WO 2006/062978 (Scheme 15; Example 4, Step B and Example 5, Step B).

Scheme 2

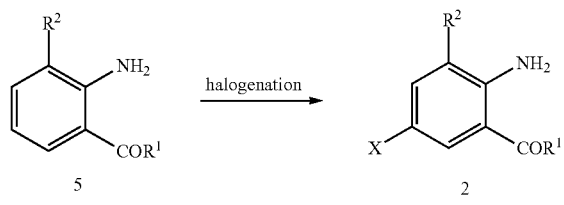

Another method for preparing compounds of Formula 2 wherein X is Br and $R^1$ is $NHR^3$ involves bromination of compounds of Formula 5 by treatment with a gas containing bromine, as illustrated by the procedure of Reference Example 1 (Reference Example 1 is also found in PCT Patent Publication WO 2008/082502).

Compounds of Formula 2a (Formula 2 wherein $R^1$ is $NHR^3$) can also be prepared by contacting an isatoic anhydride of Formula 6 with an alkyl amine of Formula 7 in the presence of a carboxylic acid as illustrated in Scheme 3.

Scheme 3

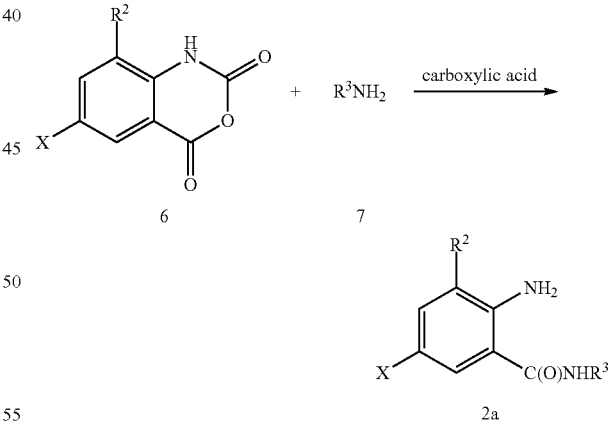

wherein $R^1$ is $NHR^3$

As amines such as the compound of Formula 7 are bases, in the absence of the carboxylic acid, the mixture of the compounds of Formulae 6 and 7 would be basic (i.e. effective pH>7). The carboxylic acid acts as a buffer to reduce the effective pH of the reaction mixture. A wide variety of carboxylic acids are useful, as the only requirement is for at least one carboxylic acid group to impart acidity. Other functional groups can be present, and more than one carboxylic acid group can be present on the carboxylic acid molecule. Typically the carboxylic acid has an effective $pK_a$ in the range of about 2 to about 5. Carboxylic acids include, for example, formic acid, acetic acid, propionic acid, chloroacetic acid, benzoic acid, phthalic acid, maleic acid, tartaric acid and citric acid. For reason of cost, inexpensive carboxylic acids such as formic acid, acetic acid, propionic acid and benzoic acid are preferred. Acetic acid, which is commercially available at low cost in its anhydrous form (known as "glacial acetic acid") is particularly preferred.

The combination of the carboxylic acid with the basic amine of Formula 7 forms an amine salt of the carboxylic acid. This amine salt can be preformed before addition of the isatoic anhydride compound of Formula 6, or the amine salt can be generated in situ by metering the amine of Formula 7 into a mixture of the compound of Formula 6 and the carboxylic acid. For either mode of addition, maintaining the effective pH of the mixture during the reaction between about 3 and about 7 is generally optimal.

As the effective pH of the mixture results from the buffering effect of the carboxylic acid in combination with the amine of Formula 7, the effective pH can be adjusted according to the effective $pK_a$ of the carboxylic acid by adjusting the molar ratio of carboxylic acid to the amine of Formula 7. Typically the molar amounts of the amine of Formula 7 to carboxylic acid are in the range from about 0.8 to about 3. More particularly, when the mode of combination involves metering the amine of Formula 7 into a mixture of the isatoic anhydride compound of Formula 6 and carboxylic acid, the molar ratio of Formula 7 amine to carboxylic acid is preferably from about 0.95 to about 3. When the mode of combination involves forming the amine salt before addition of the compound of Formula 6 the molar ratio of Formula 7 amine to carboxylic acid is preferably from about 0.8 to about 1.05; as long as a nearly equimolar ratio (e.g., about 0.95 to about 1.05) of Formula 7 amine to carboxylic acid is used, the amine salt thus formed is typically used in a ratio of about 1.1 to about 5 molar equivalents relative to the compound of Formula 6. For optimal conversions, the molar ratio of amine of Formula 7 to isatoic anhydride compound of Formula 6 should be at least 1.0, although the molar ratio is preferred to be from about 1.1 to about 1.5 for reasons of efficiency and of economy, regardless of how the components are mixed. The molar amount of amine of Formula 7 relative to compound of Formula 6 can be substantially greater than 1.5, particularly when a nearly equimolar ratio (e.g., about 0.95 to about 1.05) of amine to acid is used.

Highest product yield and purity is achieved when the reaction medium is substantially anhydrous. The reaction medium is thus typically formed from substantially anhydrous compounds of Formulae 6 and 7 and carboxylic acid. Preferably the reaction medium and forming materials contain about 5% or less, more preferably about 1% or less, and most preferably about 0.1% water or less (by weight). If the carboxylic acid is acetic acid, it is preferably in the form of glacial acetic acid.

The reaction of Scheme 3 is typically conducted in a liquid phase. In many cases the reaction can be carried out without solvent other than the compounds of Formulae 2a, 6 and 7 and the carboxylic acid. But a preferred procedure involves use of a solvent that can suspend and at least partially dissolve the reactants. Preferred solvents are those which are non-reactive with the reaction components and have a dielectric constant of about 5 or greater, such as alkyl nitriles, esters, ethers, or ketones. Preferably the solvent should be substantially anhydrous to facilitate achieving a substantially anhydrous reaction medium. The weight ratio of solvent to the compound of Formula 6 is typically from about 1 to about 20, and preferably about 5 for reasons of efficiency and economy.

Carbon dioxide forms as a byproduct of the reaction of Scheme 3. Most of the carbon dioxide formed evolves from the reaction medium as a gas. The addition of the compound of Formula 6 into reaction medium containing the amine of Formula 7 or the addition of the amine of Formula 7 into the reaction medium containing the compound of Formula 6 is preferably conducted at such a rate and temperature as to facilitate controlling the evolution of carbon dioxide. The temperature of the reaction medium is typically between about 5 and 75° C., more typically between about 35 and 55° C.

The product of Formula 2a can be isolated by standard techniques known in the art, including pH adjustment, extraction, evaporation, crystallization and chromatography. For example, the reaction medium can be diluted with about 3 to 15 parts by weight of water relative to the starting compound of Formula 6, the pH can be optionally adjusted with either acid or base to optimize the removal of either acidic or basic impurities, the water phase can be optionally separated, and most of the organic solvent can be removed by distillation or evaporation at reduced pressure. As the compounds of Formula 2a are typically crystalline solids at ambient temperature, they are generally most easily isolated by filtration, optionally followed by washing with water and then drying.

As shown in Scheme 4, isatoic anhydrides of Formula 6 can be prepared from anthranilic acids of Formula 2b (Formula 2 wherein $R^1$ is $OR^4$ and $R^4$ is H, which can be prepared by the method of Scheme 2) via a cyclization reaction involving treatment of the anthranilic acids with phosgene or a phosgene equivalent such as triphosgene or an alkyl chloroformate (e.g., methyl chloroformate) in a suitable solvent such as toluene or tetrahydrofuran. The method is described in PCT Patent Publication WO 2006/068669, including a specific example relevant to Scheme 4. Also see Coppola, *Synthesis* 1980, 505 and Fabis et al., *Tetrahedron* 1998, 10789.

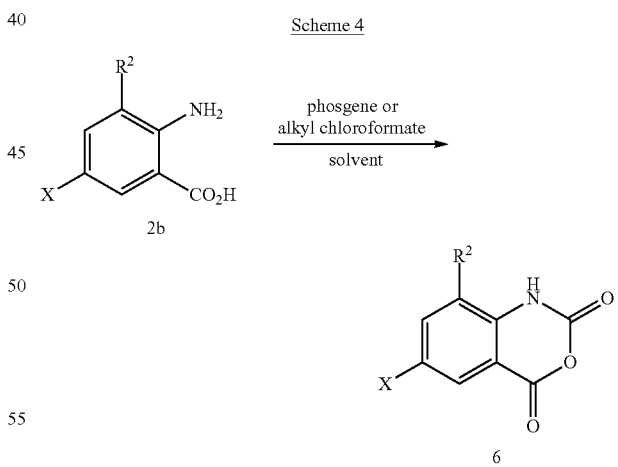

Scheme 4

Compounds of Formula 3 are commercially available and the synthetic literature describes many general methods for forming imidazoles; see, for example, Grimmett, *Science of Synthesis* 2002, 12, 325-528 and references cited therein. Bis(imidazolyl)alkanes of Formula 3 such as 1,1'-(1,4-butanediyl)bis-1H-imidazole, 1,1'-(1,5-pentanediyl)bis-1H-imidazole, 1,1'-(1,6-hexanediyl)bis-1H-imidazole, and the like can be prepared by the reaction of the corresponding dihaloalkane (e.g., 1,4-dibromobutane, 1,5-dibromopentane, 1,6-dibromohexane) with 2 equivalents of an optionally substituted imidazole in the presence of a base, according to the general procedures described by Diez-Barra et al., *Heterocycles* 1992, 34(7), 1365-1373, Torres et al., *Journal of Heterocyclic Chemistry* 1988, 25(3), 771-782, Sato, et al., *Heterocycles* 2003, 60(4), 779-784, and Luo et al., *Heterocycles* 1995, 41(7), 1421-1424.

In another aspect of the present invention, compounds of Formula 1 prepared by the method of Scheme 1 are useful as intermediates for preparing compounds of Formula 4. Compounds of Formula 4 are useful as insecticides, as described, for example in PCT Patent Publicatis WO 2003/015518 and WO 2006/055922.

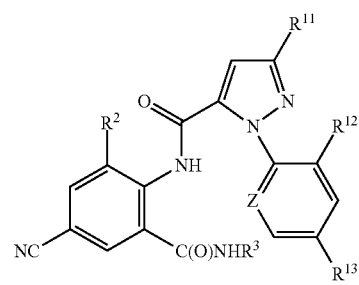

4 wherein $R^2$ is $CH_3$ or Cl;

$R^3$ is H, $C_1$-$C_4$ alkyl, cyclopropyl, cyclopropylcyclopropyl, cyclopropylmethyl or methylcyclopropyl;

Z is $CR^{14}$ or N;

$R^{11}$ is Cl, Br, $CF_3$, $OCF_2H$ or $OCH_2CF_3$;

$R^{12}$ is F, Cl or Br;

$R^{13}$ is H, F or Cl; and $R^{14}$ is H, F, Cl or Br;

A variety of methods are possible for the preparation of a compound of Formula 4 from a compound of Formula 1. As outlined in Scheme 5, one such method involves the coupling of a compound of Formula 1a (Formula 1 wherein $R^1$ is $OR^4$ and $R^4$ is H) with a pyrazole-5-carboxylic acid of Formula 8, resulting in a cyanobenzoxazinone of Formula 9. Subsequent reaction of the cyanobenzoxazinone with an amine of Formula 7 provides a compound of Formula 4. Conditions for the first step involve sequential addition of methanesulfonyl chloride in the presence of a tertiary amine such as triethylamine or pyridine to a pyrazole of Formula 8, followed by the addition of a compound of Formula 1a, followed by a second addition of tertiary amine and methanesulfonyl chloride. The reaction can be run neat or in a variety of suitable solvents including tetrahydrofuran, diethyl ether, dioxane, toluene, dichloromethane or chloroform with optimum temperatures ranging from room temperature to the reflux temperature of the solvent. The second step, reaction of benzoxazinones with amines to produce anthranilamides, is well documented in the chemical literature. For a general review of benzoxazinone chemistry see Jakobsen et al., *Biorganic and Medicinal Chemistry* 2000, 8, 2095-2103 and references cited within, and G. M. Coppola, *J. Heterocyclic Chemistry* 1999, 36, 563-588. Also see PCT Patent Publication WO 2004/067528, which teaches the general method shown in Scheme 5, including experimental examples relevant to Scheme 5.

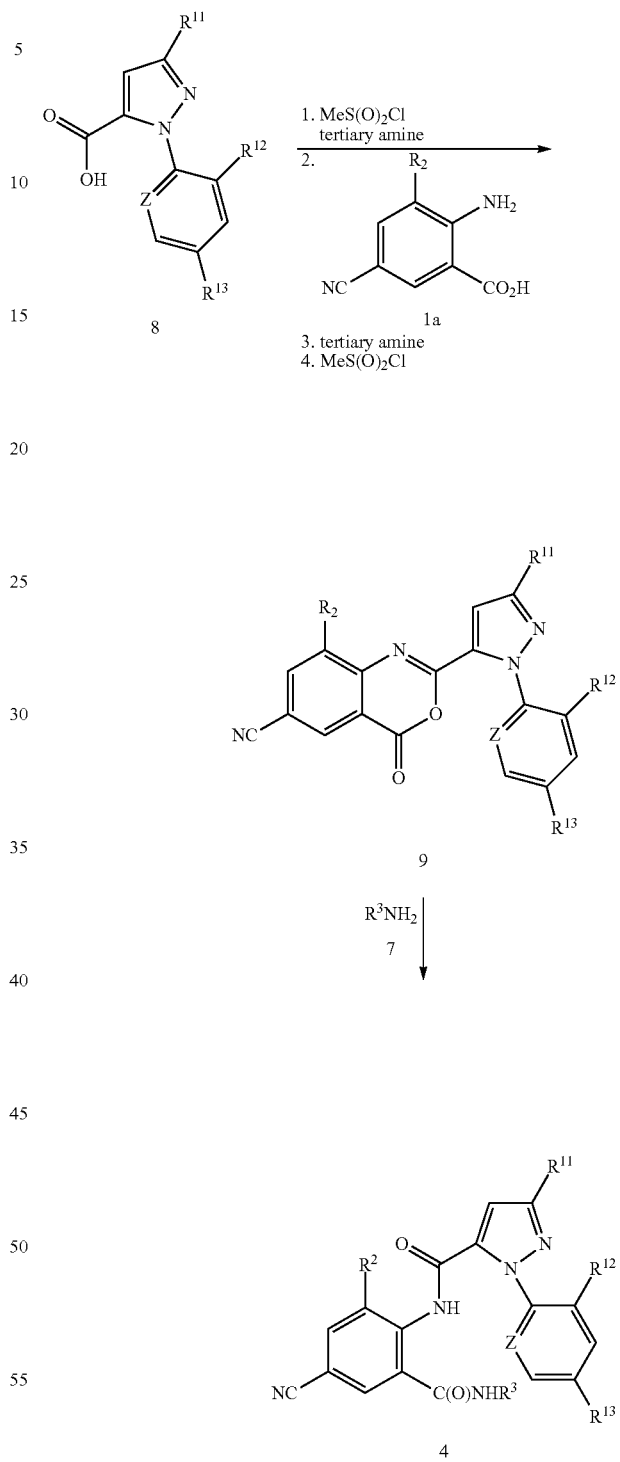

Another method of preparing compounds of Formula 4 is shown in Scheme 6. In this method a compound of Formula 4 is prepared by combining a compound of Formula 1b (Formula 1 wherein $R^1$ is $NHR^3$), a pyrazole of Formula 8 and sulfonyl chloride according to the general method taught in PCT Patent Publication WO 2006/062978, which is hereby incorporated herein in its entirety by reference.

Scheme 6

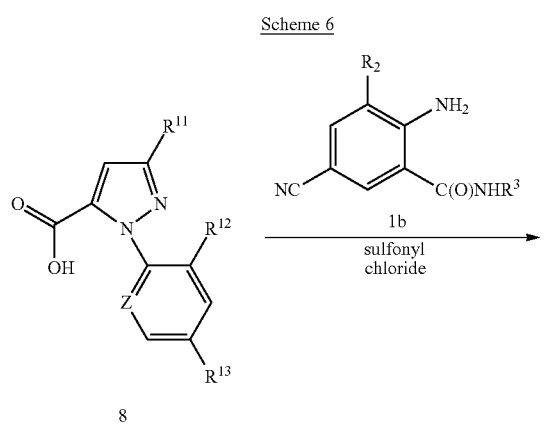

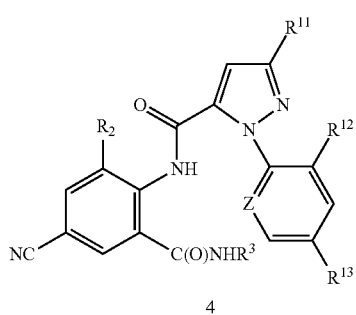

As described in WO 2006/062978, a variety of reaction conditions are possible for this transformation. Typically a sulfonyl chloride is added to a mixture of the compounds of Formulae 1b and 8 in the presence of a solvent and a base. Sulfonyl chlorides are generally of the formula $RS(O)_2Cl$ wherein R is a carbon-based radical. Usually for this method R is $C_1$-$C_4$ alkyl, $C_1$-$C_2$ haloalkyl, or phenyl optionally substituted with 1-3 substituents independently selected from the group consisting of halogen, $C_1$-$C_3$ alkyl and nitro. Commercially available sulfonyl chlorides include methanesulfonyl chloride (R is $CH_3$), propanesulfonyl chloride (R is $(CH_2)_2CH_3$), benzenesulfonyl chloride (R is phenyl), and p-toluenesulfonyl chloride (R is 4-methylphenyl). Methanesulfonyl chloride is of note for reasons of lower cost, ease of addition and/or less waste. At least one molar equivalent of the sulfonyl chloride per mole of the compound of Formula 8 is stoichiometrically needed for complete conversion. Typically the molar ratio of sulfonyl chloride to the compound of Formula 8 is no more than about 2.5, more typically no more than about 1.4.

The compound of Formula 4 is formed when the starting compounds of Formulae 1b, 8 and the sulfonyl chloride are contacted with each other in a combined liquid phase, in which each is at least partially soluble. Since the starting materials of Formulae 1b and 8 are typically solids at ordinary ambient temperatures, the method is most satisfactorily conducted using a solvent in which the starting compounds have significant solubility. Thus typically the method is conducted in a liquid phase comprising a solvent. In some cases the carboxylic acid of Formula 8 may have only slight solubility, but its salt with added base may have more solubility in the solvent. Suitable solvents for this method include nitriles such as acetonitrile and propionitrile; esters such as methyl acetate, ethyl acetate, and butyl acetate; ketones such as acetone, methyl ethyl ketone (MEK), and methyl butyl ketone; haloalkanes such as dichloromethane and trichloromethane; ethers such as ethyl ether, methyl tert-butyl ether, tetrahydrofuran (THF), and p-dioxane; aromatic hydrocarbons such as benzene, toluene, chlorobenzene, and dichlorobenzene; tertiary amines such as trialkylamines, dialkylanilines, and optionally substituted pyridines; and mixtures of the foregoing. Solvents of note include acetonitrile, propionitrile, ethyl acetate, acetone, MEK, dichloromethane, methyl tent-butyl ether, THF, p-dioxane, toluene, and chlorobenzene. Of particular note as the solvent is acetonitrile, as it often provides products in superior yield and/or purity.

As the reaction of the method of Scheme 6 generates hydrogen chloride as a byproduct, which would otherwise bind to basic centers on the compounds of Formulae 1b, 4 and 8, the method is most satisfactorily conducted in the presence of at least one added base. The base can also facilitate constructive interaction of the carboxylic acid with the sulfonyl chloride compound and the anthranilamide. Reaction of an added base with the carboxylic acid of Formula 8 forms a salt, which may have greater solubility than the carboxylic acid in the reaction medium. Although the base may be added at the same time, in alternation, or even after the addition of the sulfonyl chloride, the base is typically added before the addition of the sulfonyl chloride. Some solvents such as tertiary amines also serve as bases, and when these are used as solvents they will be in large stoichiometric excess as bases. When the base is not used as the solvent the nominal mole ratio of the base to the sulfonyl chloride is typically from about 2.0 to about 2.2, and is preferably from about 2.1 to about 2.2. Preferred bases are tertiary amines, including substituted pyridines. More preferred bases include 2-picoline, 3-picoline, 2,6-lutidine, and pyridine. Of particular note as the base is 3-picoline, as its salts with carboxylic acids of Formula 8 are often highly soluble in solvents such as acetonitrile. The method of Scheme 6 is illustrated in Example 22 below.

The compounds of Formula 4 can be isolated from the reaction mixtures by methods known to those skilled in the art, including crystallization, filtration and extraction. As disclosed in WO 2006/062978, in some cases under the coupling reaction conditions of Scheme 6 compounds of Formula 4 can partially cyclize to form iminobenzoxazine derivatives of Formula 10, as shown below in Scheme 7.

Scheme 7

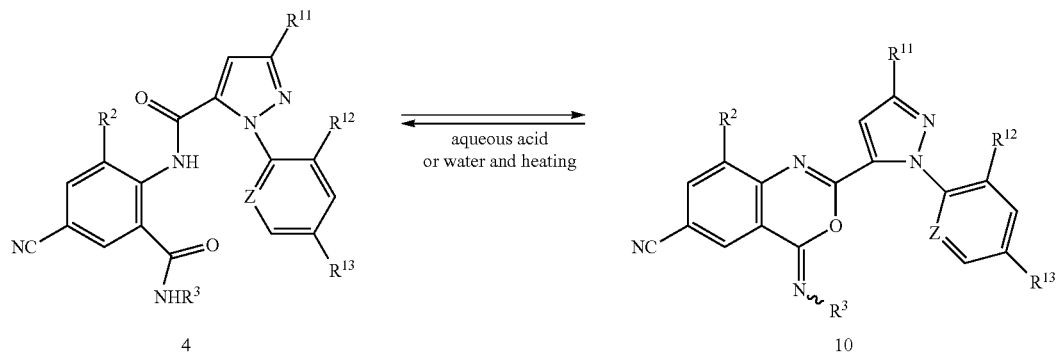

As discussed in WO 2006/062978, in these cases it is often advantageous to convert the iminobenzoxazine compounds of Formula 10 back to the amides of Formula 4 prior to isolation. This conversion can be accomplished by treatment of the reaction mixture with an aqueous acid solution (e.g., aqueous hydrochloric acid); or by isolating the mixture of Formula 10 and Formula 4 compounds, and then treating the mixture with an aqueous acid solution, optionally in the presence of a suitable organic solvent (e.g., acetonitrile). WO 2006/062978 discloses specific examples relevant to the method of Scheme 6, including examples illustrating treatment of the reaction mixture with an aqueous acid solution prior to isolating compounds of Formula 4. Example 22 below illustrates the method of Scheme 6 including the treatment of the reaction mixture with aqueous hydrochloric acid prior to isolating the compound of Formula 4.

Alternatively, compounds of Formula 10 can be converted back to compounds of Formula 4 prior to isolation by contacting the reaction mixture with water and heating. Typically, the conversion of Formula 10 compounds to Formula 4 compounds can be achieved by adding between about 2 to 6 parts by weight of water relative to the weight of the starting compound of Formula 1 and then heating to between about 45 and about 65° C. The conversion of the compound of Formula 10 to the compound of Formula 4 is usually complete in 1 h or less. Reference Example 2 below illustrates the method of Scheme 6 including the treatment of the reaction mixture with water and heating prior to isolating the compound of Formula 4.

Pyrazole-5-carboxylic acids of Formula 8 can be prepared from 5-oxo-3-pyrazolidinecarboxylates by treatment with a halogenating agent to give 3-halo-4,5-dihydro-1H-pyrazole-5-carboxylates, which can subsequently be treated with an oxidizing agent to provide esters of Formula 8. The esters can then be converted to the acids (i.e. Formula 8). Halogenating agents that can be used include, for example, phosphorus oxyhalides, phosphorus trihalides, phosphorus pentahalides, thionyl chloride, dihalotrialkylphosphoranes, dihalodiphenylphosphoranes, oxalyl chloride and phosgene. The oxidizing agents can be, for example, hydrogen peroxide, organic peroxides, potassium persulfate, sodium persulfate, ammonium persulfate, potassium monopersulfate (e.g., Oxone®) or potassium permanganate. See PCT Patent Publications WO 2003/016283, WO 2004/087689 and WO 2004/011453 for a description of the halogenation and oxidation methods, and a procedure for preparing the starting 5-oxo-3-pyrazolidinecarboxylates. To convert the esters to carboxylic acids a variety of methods reported in the chemical literature can be used, including nucleophilic cleavage under anhydrous conditions or hydrolysis involving the use of either acids or bases (see T. W. Greene and P. G. M. Wuts, *Protective Groups in Organic Synthesis*, 2nd ed., John Wiley & Sons, Inc., New York, 1991, pp. 224-269 for a review of methods). Base-catalyzed hydrolytic methods are preferred to prepare the carboxylic acids of Formula 8 from the corresponding esters. Suitable bases include alkali metal hydroxides (such as lithium, sodium, or potassium hydroxides). For example, the esters can be dissolved in a mixture of water and alcohol such as methanol. Upon treatment with sodium hydroxide or potassium hydroxide, the esters saponify to provide the sodium or potassium salt of the carboxylic acid. Acidification with a strong acid, such as hydrochloric acid or sulfuric acid, gives the carboxylic acids. PCT Patent Publication WO 2003/016283 provides a relevant experimental example illustrating the base-catalyzed hydrolysis method for the conversion of an ester to an acid.

Alternatively, pyrazole-5-carboxylic acids of Formula 8 can be prepared from 4,5-dihydro-5-hydroxy-1H-pyrazole-5-carboxylates via an acid-catalyzed dehydration reaction to give the esters, which can then be converted to the acids of Formula 8. Typical reaction conditions involve treatment of 4,5-dihydro-5-hydroxy-1H-pyrazole-5-carboxylates with an acid, for example, sulfuric acid, in an organic solvent, such as acetic acid, at temperatures between about 0 and 100° C. The method is described PCT Patent Publication WO 2003/016282. Conversion of the esters to acids can be done using the methods described above. Also, WO 2003/016282 provides a relevant experimental example for the conversion of an ester to an acid.

Anthranilic amides of Formula 1a can also be prepared from the corresponding acids or esters of Formula 1c (Formula 1 wherein $R^1$ is $OR^4$ and $R^4$ is H or $C_1$-$C_4$ alkyl) as shown below in Scheme 8. Forming amides from carboxylic acids typically involves addition of a coupling agent (e.g., silicon tetrachloride, or alternatively dicyclohexylcarbodiimide or 1-ethyl-3-(3-dimethylaminopropyl)carbodiimide often in the presence of 1-hydroxy-benzotriazole). Preparation of anthranilic amides from anthranilic acids is disclosed in M. J. Kornet, *Journal of Heterocyclic Chemistry* 1992, 29(1), 103-5; PCT Publication WO 01/66519-A2; T. Asano et al., *Bioorganic & Medicinal Chemistry Letters* 2004, 14(9), 2299-2302; H. L. Birch et al., *Bioorganic & Medicinal Chemistry Letters* 2005, 15(23), 5335-5339; and D. Kim et al., *Bioorganic & Medicinal Chemistry Letters* 2005, 15(8), 2129-2134. Also T. Asano et al. reports preparation of an anthranilic amide from an anthranilic acid through an N-protected aniline intermediate or through a 4H-3,1-benzoxazine-2,4 (1H)-dione (isatoic anhydride) intermediate. Forming amides from esters often involves heating the ester with the appropriate amine in a polar solvent such as ethylene glycol. A procedure useful for conversion of anthranilic esters to anthranilic amides is described in PCT Patent Publication WO 2006/062978. Also, E. B. Skibo et al., *Journal of Medicinal Chemistry* 2002, 45(25), 5543-5555 discloses preparation of an anthranilic amide from the corresponding anthranilic ester using sodium cyanide catalyst.

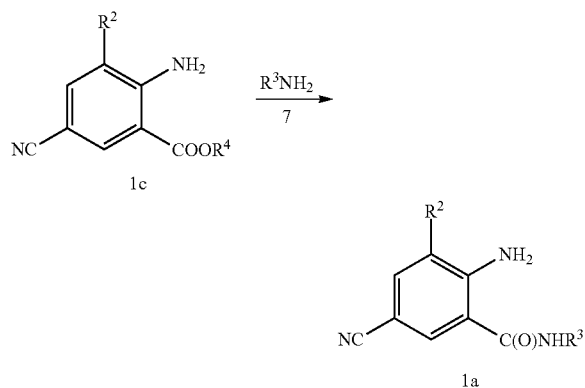

The methods of Schemes 5 and 6 are illustrative of just two of many methods for converting a compound of Formula 1 to the carboxamide compound of Formula 4. A wide variety of general methods known in the art for preparing carboxamides from carboxylic acids and amines. For a general review, see M. North, *Contemporary Org. Synth.* 1995, 2, 269-287. Particular methods include contacting a compound of Formula 1b with a compound of Formula 8 in the presence of a dehydrating coupling agent such as 1,1'-carbonyldiimidazole, bis (2-oxo-3-oxazolidinyl)phosphinic chloride or benzotriazol-1-yloxytris(dimethylamino)phosphonium hexafluorophosphate, or a polymer-bound analogous reagent such as polymer-bound dicyclohexylcarbodiimide, typically in an inert solvent such as dichloromethane or N,N-dimethylformamide, as is generally disclosed in PCT Patent Publication WO 2003/15518. Also disclosed in WO 2003/15518 is a method of preparing an acyl chloride counterpart of the compound of Formula 8, such as by contact with thionyl chloride or oxalyl chloride in the presence of a catalytic amount of N,N-dimethylformamide, and then contacting the derived acyl chloride with the compound of Formula 1b in the presence of an acid scavenger, such as an amine base (e.g., triethylamine, N,N-diisopropylethylamine, pyridine, and polymer-supported analogs) or a hydroxide or carbonate (e.g., NaOH, KOH, $Na_2CO_3$, $K_2CO_3$), typically in an inert solvent such as tetrahydrofuran, 1,4-dioxane, ethyl ether or dichloromethane. The product compounds of Formula 4 can be isolated from the reaction mixtures by methods known to those skilled in the art, including crystallization, filtration, and extraction.

Without further elaboration, it is believed that one skilled in the art using the preceding description can utilize the present invention to its fullest extent. The following Examples are, therefore, to be construed as merely illustrative, and not limiting of the disclosure in any way whatsoever. The following Examples illustrate synthesis procedures, and the starting material of each Example may not have necessarily been prepared by a particular preparative run whose procedure is described in other Examples. In Examples 13 through 16 the reaction mixtures were analyzed by reversed phase HPLC(HP Zorbax® Eclipse XDB-C8, manufactured by Agilent Technologies, 3.5 µm, 4.6 mm×75 mm). The solvent system was solvent A: water with the pH adjusted to 2.5 by the addition of phosphoric acid, and solvent B: acetonitrile (gradient started at 0 minutes with 81% solvent A and 19% solvent B, and solvent B was increased to 87% over 27 minutes; flow was 1.5 mL/minute). In Examples 17 through 21 the reaction mixtures were analyzed by reversed phase HPLC (HP Zorbax® SB-Phenyl, manufactured by Agilent Technologies, 3.5 µm, 4.6 mm×15 mm). The solvent system was solvent A: water with the pH adjusted to 3.0 by the addition of phosphoric acid, and solvent B: acetonitrile (gradient started at 0 minutes with 83% solvent A and 17% solvent B, and solvent B was increased to 95% over 15 minutes; flow was 1.5 mL/minute). $^1$H NMR spectra are reported in ppm downfield from tetramethylsilane; s is singlet, d is doublet, m is multiplet, br s is broad singlet, and br d means broad doublet.

Reference Example 1

Preparation of
2-amino-5-bromo-N,3-dimethylbenzamide (a
Compound of Formula 2)

A 1000-mL flask equipped with a mechanical stirrer, thermocouple, condenser and Teflon® fluoropolymer tubing (1/16" (0.16) cm I.D.×1/8" (0.32 cm) O.D.) (positioned such that the end of the tubing was submerged below the surface of the reaction mixture) was charged with acetic acid (226 mL). A solution of aqueous sodium hydroxide (50%, 25 g) in water (85 g) was added over 15 minutes, and then 2-amino-N,3-dimethylbenzamide (50 g, 0.305 mol) (see PCT Patent Publication WO 2006/062978 for a method of preparation) was added and the mixture was heated at 55° C. A two-necked 200-mL flask fitted on one neck with a Teflon® tubing dip tube was charged with liquid bromine (50.1 g), and the other neck was connected to the Teflon® tubing on the 1000-mL flask. Nitrogen gas was then flowed through the dip tube below the surface of the liquid bromine at a rate of about 0.012 m³ (0.4 cu ft) per h for 2.5 h, during which time all of the bromine evaporated and the bromine vapor entrained in the nitrogen gas flowed out of the two-necked 200-mL flask and entered the reaction mixture through the Teflon® tubing. The reaction temperature was held at about 55° C. during the bromine vapor addition and for 30 minutes thereafter, and then cooled to 45° C. and stirred overnight. A solution of aqueous sodium hydroxide (50%, 52 g) in water (88 mL) was added to the reaction mixture at a rate of 0.8 mL/minute. After about 10% of the total volume of the sodium hydroxide solution had been added, the addition was stopped and the reaction mixture was stirred for 1 h at 45° C. After 1 h the remaining sodium hydroxide solution was added at a rate of 0.8 mL/minute. After the addition was complete, the reaction was stirred for 30 minutes at 45° C., and then cooled to 10° C. and stirred for 1 h. The mixture was filtered and the solid collected was washed with methanol (130 mL) and water (260 mL), and then dried to a constant weight in a vacuum-oven at 45° C. to give the title compound as a solid (67 g, 99.4 area % purity by HPLC, 90% yield) melting at 133-135° C.

$^1$H NMR (DMSO-$d_6$) δ 8.30 (m, 1H), 7.49 (d, 1H), 7.22 (d, 1H), 6.35 (br s, 2H), 2.70 (d, 3H), 2.06 (s, 3H).

Example 1

Preparation of 2-amino-5-cyano-N,3-dimethylbenzamide (a Compound of Formula 1)

A 100-mL, three-necked flask equipped with a mechanical stirrer, thermometer and condenser was charged with 2-amino-5-bromo-N,3-dimethylbenzamide (prepared by the method of Reference Example 1) (99.1% purity, 5.0 g, 0.02 mol) and 1-methylnaphthalene (20 g) while maintaining a flow of nitrogen through a gas inlet line connected to the condenser. The reaction mixture was stirred at room temperature, and sodium cyanide (ground to a powder just prior to use) (1.25 g, 0.024 mol, assuming 95% purity), copper(I) iodide (0.57 g, 0.003 mol, 98% purity) and 1-butyl-1H-imidazole (2.15 g, 0.017 mol, 98% purity) were added. The mixture was heated to between 158 and 167° C. for 5 h and then allowed to cool overnight. Water (20 mL) was added dropwise to the reaction mixture over 5 minutes while stirring. After stirring for an additional 1 h, the reaction mixture was filtered, and the solid collected was washed water (3×10 mL), xylenes (10 mL) and dried to a constant weight in a vacuum-oven at 80° C. to give the title compound as a light brown solid (3.4 g).

$^1$H NMR (DMSO-$d_6$) δ 8.40 (br s, 1H), 7.79 (br s, 1H), 7.41 (br s, 1H), 7.18 (br s, 2H), 2.72 (d, 3H), 2.08 (s, 3H).

Example 2

A Second Preparation of 2-amino-5-cyano-N,3-dimethylbenzamide

A 100-mL, three-necked flask equipped with a mechanical stirrer, thermometer and condenser was charged with 2-amino-5-bromo-N,3-dimethylbenzamide (prepared by the method of Reference Example 1) (5.0 g, 0.02 mol, 99.1% purity) and 1-methylnaphthalene (20 g) while maintaining a flow of nitrogen through a gas inlet line connected to the condenser. The reaction mixture was stirred at room temperature and sodium cyanide (ground to a powder just prior to use) (1.25 g, 0.024 mol, assuming 95% purity), copper(I) iodide (0.57 g, 0.003 mol, 98% purity) and 1-methyl-1H-imidazole (1.40 g, 0.017 mol, 99%) were added. The mixture was heated to between 160 and 165° C. for 6 h and then transferred to a 200-mL flask and allowed to cool overnight. Water (20 mL) was added dropwise to the reaction mixture over 5 minutes while stirring. After stirring for an additional 2 h, the reaction mixture was filtered and the collected solid was washed with water (3×10 mL) and xylenes (10 mL) and dried to a constant weight in a vacuum-oven at 80° C. to give the title compound as a light brown solid (3.85 g).

$^1$H NMR (DMSO-$d_6$) δ 8.40 (br s, 1H), 7.80 (br s, 1H), 7.40 (br s, 1H), 7.15 (br s, 2H), 2.72 (d, 3H), 2.07 (s, 3H).

Example 3

A Third Preparation of 2-amino-5-cyano-N,3-dimethylbenzamide

A 500-mL four-necked flask equipped with a mechanical stirrer, thermocouple, condenser, side-arm addition funnel and sodium hydroxide/sodium hypochlorite scrubber was charged with 2-amino-5-bromo-N,3-dimethylbenzamide (prepared by the method of Reference Example 1) (24.6 g, 0.10 mol, 99% purity) and mesitylene (100 g) while maintaining an atmosphere of nitrogen through a gas inlet line connected to the condenser. The reaction mixture was stirred at room temperature and sodium cyanide (ground to a powder just prior to use) (6.2 g, 0.121 mol, assuming 95% purity), copper(I) iodide (2.9 g, 0.015 mol, 98% purity) and 1-butyl-1H-imidazole (10.8 g, 0.085 mol, 98% purity) were added, after which time the nitrogen inlet line was attached directly to the reaction flask. The reaction mixture was heated at reflux (about 166-170° C.) for 7 h, while venting through the scrubber. After cooling overnight, water (100 mL) was added to the reaction mixture and stirring was continued for 1 h. Ethylenediamine (0.09 g, about 0.015 mol, 99% purity) was added to the mixture, and stirring was continued for an additional 15 minutes. The mixture was filtered, and the solid collected was washed with water (3×50 mL), mesitylene (50 g) and dried to a constant weight in a vacuum-oven at 55° C. to give the title compound as a light brown solid (18.3 g).

$^1$H NMR (DMSO-$d_6$) δ 8.44 (br d, 1H), 7.82 (d, 1H), 7.44 (br s, 1H), 7.17 (br s, 2H), 2.75 (d, 3H), 2.10 (s, 3H).

Example 4

A Fourth Preparation of 2-amino-5-cyano-N,3-dimethylbenzamide

A 500-mL four-necked flask equipped with a mechanical stirrer, thermocouple, condenser, side-arm addition funnel and sodium hydroxide/sodium hypochlorite scrubber was charged with 2-amino-5-bromo-N,3-dimethylbenzamide (prepared by the method of Reference Example 1) (24.6 g, 0.10 mol, 99% purity) and mesitylene (100 g) while maintaining an atmosphere of nitrogen through a gas inlet line connected to the condenser. The reaction mixture was stirred at room temperature and sodium cyanide (ground to a powder just prior to use) (6.2 g, 0.121 mol, assuming, 95% purity), copper(I) iodide (2.9 g, 0.015 mol, 98% purity) and 1-butyl-1H-imidazole (5.4 g, 0.0425 mol, 98% purity) were added, after which time the nitrogen inlet line was attached directly to the reaction flask. The reaction mixture was heated at reflux (about 166-170° C.) for 6 h, while venting through the scrubber. After cooling overnight, water (100 mL) was added to the reaction mixture and stirring was continued for 1 h. Ethylenediamine (0.09 g, about 0.015 mol, 99% purity) was added to the reaction mixture, and stirring was continued for an additional 3.5 h. The mixture was filtered, and the solid collected was washed with water (3×50 mL), mesitylene (50 g) and dried to a constant weight in a vacuum-oven at 55° C. to give the title compound as a light brown solid (19.0 g).

$^1$H NMR (DMSO-$d_6$) δ 8.44 (br d, 1H), 7.83 (d, 1H), 7.44 (br s, 1H), 7.19 (br s, 2H), 2.74 (d, 3H), 2.10 (s, 3H).

Example 5

A Fifth Preparation of 2-amino-5-cyano-N,3-dimethylbenzamide

A 500-mL four-necked flask equipped with a mechanical stirrer, thermocouple, condenser, side-arm addition funnel and sodium hydroxide/sodium hypochlorite scrubber was charged with 2-amino-5-bromo-N,3-dimethylbenzamide (prepared by the method of Reference Example 1) (24.6 g, 0.10 mol, 99% purity) and mesitylene (100 g) while maintaining an atmosphere of nitrogen through a gas inlet line connected to the condenser. The reaction mixture was stirred at room temperature and sodium cyanide (ground to a powder just prior to use) (7.7 g, 0.15 mol, assuming 95% purity), copper(I) iodide (2.9 g, 0.015 mol, 98% purity) and 1-butyl-1H-imidazole (10.8 g, 0.085 mol, 98% purity) were added, after which time the nitrogen inlet line was attached directly to the reaction flask. The reaction mixture was heated at reflux (about 166-170° C.) for 7 h, while venting through the scrubber. After cooling overnight, water (100 mL) was added to the reaction mixture and stirring was continued for 1 h. The mixture was filtered, and the solid collected was washed with water (3×50 mL), mesitylene (50 g) and dried to a constant weight in a vacuum-oven at 55° C. to give the title compound as a light yellow solid (16.9 g).

$^1$H NMR (DMSO-$d_6$) δ 8.44 (br d, 1H), 7.82 (d, 1H), 7.44 (br s, 1H), 7.19 (br s, 2H), 2.74 (d, 3H), 2.10 (s, 3H).

Example 6

A Sixth Preparation of 2-amino-5-cyano-N,3-dimethylbenzamide

A 500-mL four-necked flask equipped with a mechanical stirrer, thermocouple, condenser, side-arm addition funnel and sodium hydroxide/sodium hypochlorite scrubber was charged with 2-amino-5-bromo-N,3-dimethylbenzamide (prepared by the method of Reference Example 1) (24.6 g, 0.10 mol, 99% purity) and mesitylene (100 g) while maintaining an atmosphere of nitrogen through a gas inlet line connected to the condenser. The mixture was stirred at room temperature and sodium cyanide (ground to a powder just prior to use) (7.7 g, 0.15 mol, assuming 95% purity), copper (I) iodide (2.9 g, 0.015 mol, 98% purity) and 1-butyl-1H-imidazole (7.6 g, 0.06 mol, 98% purity) were added, after which time the nitrogen inlet line was attached directly to the reaction flask. The reaction mixture was heated at reflux (about 166-170° C.) for 6.75 h, while venting through the scrubber. After cooling to 25° C., water (100 mL) was added to the reaction mixture and stirring was continued for 1 h. The mixture was filtered, and the solid collected was washed with water (3×50 mL), mesitylene (50 g) and dried to a constant weight in a vacuum-oven at 55° C. to give the title compound as a light yellow solid (17.7 g).

$^1$H NMR (DMSO-$d_6$) δ 8.44 (br d, 1H), 7.82 (d, 1H), 7.44 (br s, 1H), 7.19 (br s, 2H), 2.74 (d, 3H), 2.10 (s, 3H).

Example 7

A Seventh Preparation of 2-amino-5-cyano-N,3-dimethylbenzamide

A 500-mL four-necked flask equipped with a mechanical stirrer, thermocouple, condenser, side-arm addition funnel and sodium hydroxide/sodium hypochlorite scrubber was charged with 2-amino-5-bromo-N,3-dimethylbenzamide (prepared by the method of Reference Example 1) (24.6 g, 0.10 mol, 99% purity) and mesitylene (100 g) while maintaining an atmosphere of nitrogen through a gas inlet line connected to the condenser. The mixture was stirred at room temperature and sodium cyanide (ground to a powder just prior to use) (7.7 g, 0.15 mol, assuming 95% purity) and copper(I) iodide (2.9 g, 0.015 mol, 98% purity) and 1-ethyl-1H-imidazole (5.9 g, 0.06 mol, 98% purity) were added, after which time the nitrogen inlet line was attached directly to the reaction flask. The reaction mixture was heated at reflux (about 166-170° C.) for 8 h, while venting through the scrubber. After cooling overnight, water (100 mL) was added, and stirring was continued for 1 h. The mixture was filtered, and the solid collected was washed with water (3×50 mL), mesitylene (50 g) and dried to a constant weight in a vacuum-oven at 55° C. to give the title compound as a light yellow solid (18.0 g).

$^1$H NMR (DMSO-$d_6$) δ 8.44 (br d, 1H), 7.82 (d, 1H), 7.44 (br s, 1H), 7.19 (br s, 2H), 2.74 (d, 3H), 2.11 (s, 3H).

Example 8

An Eighth Preparation of 2-amino-5-cyano-N,3-dimethylbenzamide

A 500-mL four-necked flask equipped with a mechanical stirrer, thermocouple, condenser, side-arm addition funnel and sodium hydroxide/sodium hypochlorite scrubber was charged with 2-amino-5-bromo-N,3-dimethylbenzamide (prepared by the method of Reference Example 1) (24.6 g, 0.10 mol, 99% purity) and mesitylene (100 g) while maintaining an atmosphere of nitrogen through a gas inlet line connected to the condenser. The mixture was stirred at room temperature, and sodium cyanide (ground to a powder just prior to use) (7.7 g, 0.15 mol, assuming 95% purity), copper (I) iodide (2.9 g, 0.015 mol, 98% purity) and 1-butyl-1H-imidazole (9.5 g, 0.075 mol, 98% purity) were added, after which time the nitrogen inlet line was attached directly to the reaction flask. The reaction mixture was heated at reflux (about 166-170° C.) for 6 h, while venting through the scrubber. After cooling overnight, water (100 mL) was added to the reaction mixture, and stirring was continued for 1 h. The mixture was filtered, and the solid collected was washed with water (3×50 mL), mesitylene (50 g) and dried to a constant weight in a vacuum-oven at 55° C. to give the title compound as a light yellow solid (17.0 g).

Example 9

A Ninth Preparation of 2-amino-5-cyano-N,3-dimethylbenzamide

A 500-mL four-necked flask equipped with a mechanical stirrer, thermocouple, condenser, side-arm addition funnel and sodium hydroxide/sodium hypochlorite scrubber was charged with 2-amino-5-bromo-N,3-dimethylbenzamide (prepared by the method of Reference Example 1) (24.6 g, 0.10 mol, 99% purity) and mesitylene (100 g) while maintaining an atmosphere of nitrogen through a gas inlet line connected to the condenser. The reaction mixture was stirred at room temperature, and granular sodium cyanide (Alfa Aesar®, 7.7 g, 0.15 mol, assuming 95% purity), copper(I) iodide (2.9 g, 0.015 mol, 98% purity) and 1-butyl-1H-imidazole (10.8 g, 0.085 mol, 98% purity) were added to the reaction mixture, after which time the nitrogen inlet line was attached directly to the reaction flask. The reaction mixture was heated at reflux (about 166-170° C.) for 6 h, while venting through the scrubber and then allow to cool overnight. Water (100 mL) was added to the reaction mixture and stirring was continued for 45 minutes. More water (25 mL) was added to the reaction mixture and stirring continued for an additional 15 minutes. The mixture was filtered, and the solid collected was washed with water (3×50 mL), mesitylene (50 g) and dried to a constant weight in a vacuum-oven at 55° C. to give the title compound as a light yellow solid (16.8 g).

$^1$H NMR (DMSO-$d_6$) δ 8.44 (br d, 1H), 7.82 (d, 1H), 7.44 (br s, 1H), 7.18 (br s, 2H), 2.74 (d, 3H), 2.10 (s, 3H).

Example 10

A Tenth Preparation of 2-amino-5-cyano-N,3-dimethylbenzamide

A 100-mL three-necked flask equipped with a mechanical stirrer, thermometer and condenser was charged with 2-amino-5-bromo-N,3-dimethylbenzamide (prepared by the method of Reference Example 1) (99% purity, 5.0 g, 0.02 mol) and mesitylene (20 g) while maintaining a flow of nitrogen through a gas inlet line connected to the condenser. The reaction mixture was stirred at room temperature, and sodium cyanide powder (CyPlus®, 1.40 g, 0.027 mol, assuming 95% purity), copper(I) cyanide (0.27 g, 0.003 mol, 99% purity), sodium iodide (0.45 g, 0.003 mol, 99% purity) and 1-butyl-1H-imidazole (1.9 g, 0.015 mol, 98% purity) were added. The mixture was heated at reflux (about 167-168° C.) for 6 h and then allowed to cool overnight. Water (20 mL) was added dropwise to the reaction mixture over 5 minutes while stirring. After stirring for an additional 1 h, the reaction mixture was filtered, and the solid collected was washed successively with water (3×10 mL), mesitylene (10 mL) and dried to a constant weight in a vacuum-oven at 55° C. to give the title compound as a light yellow solid (3.4 g).

$^1$H NMR (DMSO-$d_6$) δ 8.44 (br s, 1H), 7.82 (br s, 1H), 7.44 (br s, 1H), 7.18 (br s, 2H), 2.74 (d, 3H), 2.10 (s, 3H).

Example 11

An Eleventh Preparation of 2-amino-5-cyano-N,3-dimethylbenzamide

A 100-mL reactor (HP autoMATE high pressure reactor system constructed of Hastelloy® C and produced by HEL, Inc., Lawrenceville, N.J.) was equipped with a mechanical stirrer (constructed of Hastelloy® C) with a twin turbine agitator (bottom turbine pumping up and top turbine pumping down). The reactor was purged with nitrogen, then maintained under a nitrogen atmosphere, and charged successively with 2-amino-5-bromo-N,3-dimethylbenzamide (prepared by the method of Reference Example 1) (99% purity, 7.4 g, 0.03 mol), sodium cyanide powder (CyPlus®, 2.3 g, 0.045 mol, assuming 95% purity), copper(I) iodide (98% purity, 0.87 g, 0.0045 mol), xylenes (30 g) and 1-butyl-1H-imidazole (3.2 g, 0.0255 mol, 98% purity). The reactor was pressurized to 345 kPa with nitrogen and then vented. The nitrogen pressurization/venting procedure was repeated five times. Stirring was started at 300 rpm, and the reactor was leak tested by pressurization to 690 kPa for 20 minutes. The reactor was vented, the vent was closed, and the reaction mixture was heated at 170° C. for 6 h. The reaction mixture was cooled to between 20 and 25° C., and the reactor was vented and allowed to stand over the weekend. The reaction mixture was transferred to a 250-mL Erlenmeyer flask, and water (30 g) was added. After stirring for 1 h, the reaction mixture was filtered and the solid collected was washed successively with water (3×15 mL) and xylenes (15 mL), and dried to a constant weight in a vacuum-oven at 55° C. to give the title compound as a light yellow solid (5.2 g).

$^1$H NMR (DMSO-$d_6$) δ 8.44 (br s, 1H), 7.82 (br s, 1H), 7.44 (br s, 1H), 7.18 (br s, 2H), 2.74 (d, 3H), 2.10 (s, 3H).

Example 12

An Twelfth Preparation of 2-amino-5-cyano-N,3-dimethylbenzamide

A 100-mL reactor (HP autoMATE high pressure reactor system constructed of Hastelloy® C and produced by HEL, Inc.) was equipped with a mechanical stirrer (constructed of Hastelloy® C) with a twin turbine agitator (bottom turbine pumping up and top turbine pumping down). The reactor was purged with nitrogen, then maintained under a nitrogen atmosphere, and charged successively with 2-amino-5-bromo-N, 3-dimethylbenzamide (prepared by the method of Reference Example 1) (99% purity, 7.4 g, 0.03 mol), sodium cyanide powder (CyPlus®, 2.3 g, 0.045 mol, assuming 95% purity), copper(I) iodide (98% purity, 0.87 g, 0.0045 mol), toluene (30 g) and 1-butyl-1H-imidazole (3.2 g, 0.0255 mol, 98% purity). The reactor was pressurized to 345 kPa with nitrogen and then vented. The nitrogen pressurization/venting procedure was repeated five times. Stirring was started at 300 rpm, and the reactor was leak tested by pressurization to 690 kPa for 20 minutes. The reactor was vented, the vent was closed, and the reaction mixture was heated at 170° C. for 6 h. The reaction mixture was cooled to between 20 and 25° C., and the reactor was vented and allowed to stand over the weekend. Then the reaction mixture was transferred to a 250-mL Erlenmeyer flask, and water (30 g) was added. After stirring for 1 h, the reaction mixture was filtered, and the solid collected was washed successively with water (3×15 mL) and toluene (15 mL), and dried to a constant weight in a vacuum-oven at 55° C. to give the title compound as a light yellow solid (5.0 g).

$^1$H NMR (DMSO-$d_6$) δ 8.44 (br s, 1H), 7.83 (br s, 1H), 7.44 (br s, 1H), 7.19 (br s, 2H), 2.75 (d, 3H), 2.11 (s, 3H).

Example 13

A Thirteenth Preparation of 2-amino-5-cyano-N,3-dimethylbenzamide

A 100-mL reactor (HP autoMATE high pressure reactor system constructed of Hastelloy® C and produced by HEL, Inc.) was equipped with a mechanical stirrer (constructed of Hastelloy® C) with a twin turbine agitator (bottom turbine pumping up and top turbine pumping down). The reactor was purged with nitrogen, then maintained under a nitrogen atmosphere, and charged successively with 2-amino-5-bromo-N, 3-dimethylbenzamide (prepared by the method of Reference Example 1) (99% purity, 7.4 g, 0.03 mol), sodium cyanide powder (CyPlus®, 2.3 g, 0.045 mol, assuming 95% purity), copper(I) iodide (98% purity, 0.87 g, 0.0045 mol) and xylenes (20 g). The reactor was pressurized to 345 kPa with nitrogen and then vented. The nitrogen pressurization/venting procedure was repeated two times. Stirring was started at 300 rpm, and the reactor was leak tested by pressurization to 690 kPa for 20 minutes. The reactor was vented to atmospheric pressure, and a solution of 1-methylimidazole (1.86 g, 0.0255 mol, 99% purity) in xylenes (10 mL) was added to the reaction mixture. The reactor was pressurized to 345 kPa with nitrogen and then vented. The nitrogen pressurization/venting procedure was repeated two times. The reactor vent was closed, and the mixture was heated at 170° C. for 8 h. Then the reaction mixture was cooled to between 20 and 25° C., and the reactor was vented and allowed to stand overnight. Then the reaction mixture was diluted with N,N-dimethylformamide (DMF) (total weight of the reaction mixture after dilution with DMF was 100 g) and analyzed by HPLC, which indicated 98% conversion of the 2-amino-5-bromo-N,3-dimethylbenzamide with 2-amino-5-cyano-N,3-dimethylbenzamide being the major product.

Example 14

A Fourteenth Preparation of 2-amino-5-cyano-N,3-dimethylbenzamide

A 100-mL reactor (HP autoMATE high pressure reactor system constructed of Hastelloy® C and produced by HEL, Inc.) was equipped with a mechanical stirrer (constructed of Hastelloy® C) with a twin turbine agitator (bottom turbine pumping up and top turbine pumping down). The reactor was purged with nitrogen, then maintained under a nitrogen atmosphere, and charged successively with 2-amino-5-bromo-N,3-dimethylbenzamide (prepared by the method of Reference Example 1) (99% purity, 7.4 g, 0.03 mol), sodium cyanide powder (CyPlus®, 2.3 g, 0.045 mol, assuming 95% purity), copper(I) iodide (98% purity, 0.87 g, 0.0045 mol) and toluene (20 g). The reactor was pressurized to 345 kPa with nitrogen and then vented. The nitrogen pressurization/venting procedure was repeated two times. Stirring was started at 300 rpm, and the reactor was leak tested by pressurization to 690 kPa for 20 minutes. The reactor was vented to atmospheric pressure, and a solution of 1-methylimidazole (1.86 g, 0.0255 mol, 99% purity) in toluene (10 mL) was added to the reaction mixture. The reactor was pressurized to 345 kPa with nitrogen and then vented. The nitrogen pressurization/venting procedure was repeated two times. The reactor vent was closed, and the mixture was heated at 170° C. for 8 h. The reaction mixture was cooled to between 20 and 25° C., and the reactor was vented and allowed to stand overnight. Then the reaction mixture was diluted with DMF (total weight of the reaction mixture after dilution with DMF was 100 g) and analyzed by HPLC, which indicated 99% conversion of the 2-amino-5-bromo-N,3-dimethylbenzamide with 2-amino-5-cyano-N,3-dimethylbenzamide being the major product.

Example 15

A Fifteenth Preparation of 2-amino-5-cyano-N,3-dimethylbenzamide

A 100-mL reactor (HP autoMATE high pressure reactor system constructed of Hastelloy® C and produced by HEL, Inc.) was equipped with a mechanical stirrer (constructed of Hastelloy® C) with a twin turbine agitator (bottom turbine pumping up and top turbine pumping down). The reactor was purged with nitrogen, then maintained under a nitrogen atmosphere, and charged successively with 2-amino-5-bromo-N,3-dimethylbenzamide (prepared by the method of Reference Example 1) (99% purity, 7.4 g, 0.03 mol), sodium cyanide powder (CyPlus®, 2.3 g, 0.045 mol, assuming 95% purity), copper(I) iodide (98% purity, 0.87 g, 0.0045 mol) and xylenes (20 g). The reactor was pressurized to 345 kPa with nitrogen and then vented. The nitrogen pressurization/venting procedure was repeated two times. Stirring was started at 300 rpm, and the reactor was leak tested by pressurization to 690 kPa for 20 minutes. The reactor was vented to atmospheric pressure and a solution of 4-methylimidazole (1.86 g, 0.0255 mol, 98% purity) in xylenes (10 mL) was added to the reaction mixture. The reactor was pressurized to 345 kPa with nitrogen and then vented. The nitrogen pressurization/venting procedure was repeated two times. The reactor vent was closed, and the mixture was heated at 170° C. for 12 h. The reaction mixture was cooled to between 20 and 25° C., and the reactor was vented and allowed to stand overnight. Then the reaction mixture was diluted with DMF (total weight of the reaction mixture after dilution with DMF was 100 g) and analyzed by HPLC, which indicated 88% conversion of the 2-amino-5-bromo-N,3-dimethylbenzamide with 2-amino-5-cyano-N,3-dimethylbenzamide being the major product.

Example 16

A Sixteenth Preparation of 2-amino-5-cyano-N,3-dimethylbenzamide

A 100-mL reactor (HP autoMATE high pressure reactor system constructed of Hastelloy® C and produced by HEL, Inc.) was equipped with a mechanical stirrer (constructed of Hastelloy® C) with a twin turbine agitator (bottom turbine pumping up and top turbine pumping down). The reactor was purged with nitrogen, then maintained under a nitrogen atmosphere, and charged successively with 2-amino-5-bromo-N,3-dimethylbenzamide (prepared by the method of Reference Example 1) (99% purity, 7.4 g, 0.03 mol), sodium cyanide powder (CyPlus®, 2.3 g, 0.045 mol, assuming 95% purity), copper(I) iodide (98% purity, 0.87 g, 0.0045 mol), 1,6-bis(imidazol-1-yl)hexane (2.5 g, 0.011 mol) and xylenes (30 g). The reactor was pressurized to 345 kPa with nitrogen and then vented. The nitrogen pressurization/venting procedure was repeated two times. Stirring was started at 300 rpm, and the reactor was leak tested by pressurization to 690 kPa for 20 minutes. The reactor was vented to atmospheric pressure, the vent was then closed and the reaction mixture was heated at 170° C. for 12 h. The reaction mixture was cooled to between 20 and 25° C., and the reactor was vented and allowed to stand overnight. Then the reaction mixture was diluted with DMF (total weight of the reaction mixture after dilution with DMF was 100 g) and analyzed by HPLC, which indicated 93% conversion of the 2-amino-5-bromo-N,3-dimethylbenzamide with 2-amino-5-cyano-N,3-dimethylbenzamide being the major product.

Example 17

A Seventeenth Preparation of 2-amino-5-cyano-N,3-dimethylbenzamide

A 125-mL reactor (Advantage Series® 3400 Process Chemistry Workstation, sold by Biotage) was equipped with a mechanical stirrer (shaft constructed of Hastelloy® C with polyetheretherketone (PEEK) stirrer bearing and PEEK turbine style agitator), temperature probe (constructed of Hastelloy® C) and a reflux condenser. The reactor was charged with 2-amino-5-bromo-N,3-dimethylbenzamide (prepared by the method of Reference Example 1) (99% purity, 9.8 g, 0.04 mol), copper(I) iodide (98% purity, 1.17 g, 0.006 mol) and granular sodium cyanide (Alfa Aesar®, 3.09 g, 0.060 mol, assuming 95% purity). The reactor was purged with nitrogen through a gas inlet line connected to the condenser, then a solution of 1-butyl-1H-imidazole (0.76 g, 0.006 mol, 98% purity) in mesitylene (40 g) was added to the reaction mixture. The agitator was turned on at 300 rpm, and the mixture heated to reflux for 6 h. The reaction mixture was cooled 20° C. and allowed to stand overnight. Then the reaction mixture was diluted with DMF (total weight of the reaction mixture after dilution with DMF was 130 g) and analyzed by HPLC, which indicated 97% conversion of the 2-amino-5-bromo-N,3-dimethylbenzamide with 2-amino-5-cyano-N,3-dimethylbenzamide being the major product.

Example 18

An Eighteenth Preparation of 2-amino-5-cyano-N,3-dimethylbenzamide

The title compound was prepared by the procedure of Example 17 using a different amount of 1-butyl-1H-imidazole (1.52 g, 0.012 mol). Analysis of the reaction mixture by HPLC indicated 97% conversion of the 2-amino-5-bromo-N, 3-dimethylbenzamide with 2-amino-5-cyano-N,3-dimethyl-benzamide being the major product.

Example 19

A Nineteenth Preparation of 2-amino-5-cyano-N,3-dimethylbenzamide

The title compound was prepared by the procedure of Example 17 using a different amount of 1-butyl-1H-imidazole (2.27 g, 0.018 mol). Analysis of the reaction mixture by HPLC indicated 97% conversion of the 2-amino-5-bromo-N,3-dimethylbenzamide with 2-amino-5-cyano-N,3-dimethyl-benzamide being the major product.

Example 20

A Twentieth Preparation of 2-amino-5-cyano-N,3-dimethylbenzamide

The title compound was prepared by the procedure of Example 17 using a different amount of 1-butyl-1H-imidazole (3.03 g, 0.024 mol). Analysis of the reaction mixture by HPLC indicated 99% conversion of the 2-amino-5-bromo-N,3-dimethylbenzamide with 2-amino-5-cyano-N,3-dimethyl-benzamide being the major product.

Example 21

A Twenty First Preparation of 2-amino-5-cyano-N,3-dimethylbenzamide

The title compound was prepared by the procedure of Example 17 using a different amount of 1-butyl-1H-imidazole (3.82 g, 0.030 mol). Analysis of the reaction mixture by HPLC indicated 98% conversion of the 2-amino-5-bromo-N,3-dimethylbenzamide with 2-amino-5-cyano-N,3-dimethyl-benzamide being the major product.

Example 22

Preparation of 3-bromo-1-(3-chloro-2-pyridinyl)-N-[4-cyano-2-methyl-6-[(methylamino)carbonyl]phenyl]-1H-pyrazole-5-carboxamide To a mixture of 3-bromo-1-(3-chloro-2-pyridinyl)-1H-pyrazole-5-carboxylic acid (see PCT Patent Publication WO 2003/015519 for a method of preparation) (3.02 g, 0.010 mol) and 2-amino-5-cyano-N,3-dimethylbenzamide (prepared by the method of Example 9, with the exception that the 2-amino-5-bromo-N,3-dimethylbenzamide was obtained from a commercial source and sodium cyanide powder from CyPlus® was used) (1.99 g, 0.0105 mol) in acetonitrile (16 mL) was added 3-picoline (2.92 mL, 0.030 mol). The reaction mixture was cooled to 15 to 20° C., and then methanesulfonyl chloride (8.2 g, 0.071 mol) was added dropwise. After stirring for 2 h at 20° C., water (7.5 mL) was added dropwise to the reaction mixture while maintaining the temperature at 20 to 25° C. After 15 minutes, concentrated hydrochloric acid (0.50 mL) was added, and the reaction mixture was stirred for 1 h at 20° C. The mixture was filtered, and the solids collected were washed with acetonitrile-water (3:1 mixture, 2×2 mL) and water (2×2 mL), and dried under nitrogen to afford the title compound (4.86 g) as an off-white solid melting at 206-208° C.

$^1$H NMR (DMSO-d$_6$) δ 10.52 (br s, 1H), 8.50 (dd, 1H), 8.36 (m, 1H), 8.17 (dd, 1H), 7.88 (d, 1H), 7.76 (d, 1H), 7.62 (m, 1H), 7.41 (s, 1H), 2.66 (d, 3H), 2.21 (s, 3H).

Reference Example 2

Preparation of 3-bromo-1-(3-chloro-2-pyridinyl)-N-[4-cyano-2-methyl-6-[(methylamino)carbonyl]phenyl]-1H-pyrazole-5-carboxamide (a Compound of Formula 4)

To a mixture of 3-bromo-1-(3-chloro-2-pyridinyl)-1H-pyrazole-5-carboxylic acid (see PCT Patent Publication WO 2003/015519 for a method of preparation) (15 g, 0.049 mol, 97.4% purity) and 2-amino-5-cyano-N,3-dimethylbenzamide (see PCT Patent Publication WO 2006/62978 for a method of preparation) (10.0 g, 0.0525 mol) in acetonitrile (80 mL) was added 3-picoline (13.9 g, 0.148 mol). The reaction mixture was cooled to 15 to 20° C., and then methanesulfonyl chloride (8.2 g, 0.071 mol) was added dropwise. After 1 h, water (37.3 g) was added dropwise to the reaction mixture while maintaining the temperature at 15 to 20° C. The mixture was heated at 45 to 50° C. for 30 minutes and then cooled to 15 to 25° C. for 1 h. The mixture was filtered, and the solids collected were washed with acetonitrile-water (approximately a 5:1 mixture, 2×10 mL) and acetonitrile (2×10 mL), and then dried under nitrogen to afford the title compound (24.0 g, 93.6% corrected yield based on an assay of 91.6%) as an off-white solid.

$^1$H NMR (DMSO-d$_6$) δ 10.53 (br s, 1H), 8.49 (dd, 1H), 8.36 (m, 1H), 8.16 (dd, 1H), 7.87 (d, 1H), 7.76 (d, 1H), 7.60 (m, 1H), 7.41 (s, 1H), 2.67 (d, 3H), 2.21 (s, 3H).

Table 1 illustrates the particular transformations to prepare compounds of Formula 1 according to a method of the present invention. For these transformations, the copper(I) salt reagent and the iodide salt reagent are copper(I) iodide. In Table 1 and the following tables: t means tertiary, s means secondary, n means normal, i means iso, c means cyclo, Me means methyl, Et means ethyl, Pr means propyl, and Bu means butyl. Concatenations of groups are abbreviated similarly; for example, "c-PrCH$_2$" means cyclopropylmethyl.

TABLE 1

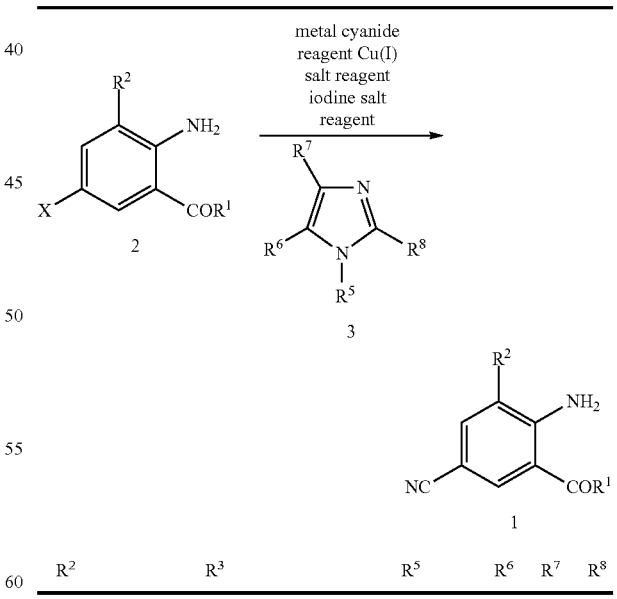

| $R^2$ | $R^3$ | $R^5$ | $R^6$ | $R^7$ | $R^8$ |
|---|---|---|---|---|---|
| $R^1$ is NHR$^3$, X is Br, and the metal cyanide is sodium cyanide. | | | | | |
| Me | H | Me | H | H | H |
| Me | Me | Me | H | H | H |
| Me | Et | Me | H | H | H |
| Me | n-Pr | Me | H | H | H |
| Me | i-Pr | Me | H | H | H |

TABLE 1-continued

| | | | | | |
|---|---|---|---|---|---|
| Me | n-Bu | Me | H | H | H |
| Me | i-Bu | Me | H | H | H |
| Me | s-Bu | Me | H | H | H |
| Me | t-Bu | Me | H | H | H |
| Me | c-Pr | Me | H | H | H |
| Me | c-PrCH$_2$ | Me | H | H | H |
| Me | 1-CH$_3$-c-Pr | Me | H | H | H |
| Me | 2-CH$_3$-c-Pr | Me | H | H | H |
| Me | 1,1'-bicyclopropyl-2-yl | Me | H | H | H |
| Me | 1,1'-bicyclopropyl-1-yl | Me | H | H | H |
| Me | (1R,2S)-1,1'-bicyclopropyl-2-yl | Me | H | H | H |

R$^1$ is NHR$^3$, X is Br, and the metal cyanide is potassium cyanide.

| | | | | | |
|---|---|---|---|---|---|
| Me | H | Me | H | H | H |
| Me | Me | Me | H | H | H |
| Me | Et | Me | H | H | H |
| Me | n-Pr | Me | H | H | H |
| Me | i-Pr | Me | H | H | H |
| Me | n-Bu | Me | H | H | H |
| Me | i-Bu | Me | H | H | H |
| Me | s-Bu | Me | H | H | H |
| Me | t-Bu | Me | H | H | H |
| Me | c-Pr | Me | H | H | H |
| Me | c-PrCH$_2$ | Me | H | H | H |
| Me | 1-CH$_3$-c-Pr | Me | H | H | H |
| Me | 2-CH$_3$-c-Pr | Me | H | H | H |
| Me | 1,1'-bicyclopropyl-2-yl | Me | H | H | H |
| Me | 1,1'-bicyclopropyl-1-yl | Me | H | H | H |
| Me | (1R,2S)-1,1'-bicyclopropyl-2-yl | Me | H | H | H |

R$^1$ is NHR$^3$, X is Br, and the metal cyanide is potassium hexacyanoferrate(II).

| | | | | | |
|---|---|---|---|---|---|
| Me | H | Me | H | H | H |
| Me | Me | Me | H | H | H |
| Me | Et | Me | H | H | H |
| Me | n-Pr | Me | H | H | H |
| Me | i-Pr | Me | H | H | H |
| Me | n-Bu | Me | H | H | H |
| Me | i-Bu | Me | H | H | H |
| Me | s-Bu | Me | H | H | H |
| Me | t-Bu | Me | H | H | H |
| Me | c-Pr | Me | H | H | H |
| Me | c-PrCH$_2$ | Me | H | H | H |
| Me | 1-CH$_3$-c-Pr | Me | H | H | H |
| Me | 2-CH$_3$-c-Pr | Me | H | H | H |
| Me | 1,1'-bicyclopropyl-2-yl | Me | H | H | H |
| Me | 1,1'-bicyclopropyl-1-yl | Me | H | H | H |
| Me | (1R,2S)-1,1'-bicyclopropyl-2-yl | Me | H | H | H |

R$^1$ is NHR$^3$, X is Br, and the metal cyanide is sodium cyanide.

| | | | | | |
|---|---|---|---|---|---|
| Me | H | n-Bu | H | H | H |
| Me | Me | n-Bu | H | H | H |
| Me | Et | n-Bu | H | H | H |
| Me | n-Pr | n-Bu | H | H | H |
| Me | i-Pr | n-Bu | H | H | H |
| Me | n-Bu | n-Bu | H | H | H |
| Me | i-Bu | n-Bu | H | H | H |
| Me | s-Bu | n-Bu | H | H | H |
| Me | t-Bu | n-Bu | H | H | H |
| Me | c-Pr | n-Bu | H | H | H |
| Me | c-PrCH$_2$ | n-Bu | H | H | H |
| Me | 1-CH$_3$-c-Pr | n-Bu | H | H | H |
| Me | 2-CH$_3$-c-Pr | n-Bu | H | H | H |
| Me | 1,1'-bicyclopropyl-2-yl | n-Bu | H | H | H |
| Me | 1,1'-bicyclopropyl-1-yl | n-Bu | H | H | H |
| Me | (1R,2S)-1,1'-bicyclopropyl-2-yl | n-Bu | H | H | H |

R$^1$ is NHR$^3$, X is Br, and the metal cyanide is potassium cyanide.

| | | | | | |
|---|---|---|---|---|---|
| Me | H | n-Bu | H | H | H |
| Me | Me | n-Bu | H | H | H |
| Me | Et | n-Bu | H | H | H |
| Me | n-Pr | n-Bu | H | H | H |
| Me | i-Pr | n-Bu | H | H | H |
| Me | n-Bu | n-Bu | H | H | H |
| Me | i-Bu | n-Bu | H | H | H |
| Me | s-Bu | n-Bu | H | H | H |
| Me | t-Bu | n-Bu | H | H | H |
| Me | c-Pr | n-Bu | H | H | H |
| Me | c-PrCH$_2$ | n-Bu | H | H | H |
| Me | 1-CH$_3$-c-Pr | n-Bu | H | H | H |
| Me | 2-CH$_3$-c-Pr | n-Bu | H | H | H |
| Me | 1,1'-bicyclopropyl-2-yl | n-Bu | H | H | H |
| Me | 1,1'-bicyclopropyl-1-yl | n-Bu | H | H | H |
| Me | (1R,2S)-1,1'-bicyclopropyl-2-yl | n-Bu | H | H | H |

R$^1$ is NHR$^3$, X is Br, and the metal cyanide is potassium hexacyanoferrate(II).

| | | | | | |
|---|---|---|---|---|---|
| Me | H | n-Bu | H | H | H |
| Me | Me | n-Bu | H | H | H |
| Me | Et | n-Bu | H | H | H |
| Me | n-Pr | n-Bu | H | H | H |
| Me | i-Pr | n-Bu | H | H | H |
| Me | n-Bu | n-Bu | H | H | H |
| Me | i-Bu | n-Bu | H | H | H |
| Me | s-Bu | n-Bu | H | H | H |
| Me | t-Bu | n-Bu | H | H | H |
| Me | c-Pr | n-Bu | H | H | H |
| Me | c-PrCH$_2$ | n-Bu | H | H | H |
| Me | 1-CH$_3$-c-Pr | n-Bu | H | H | H |
| Me | 2-CH$_3$-c-Pr | n-Bu | H | H | H |
| Me | 1,1'-bicyclopropyl-2-yl | n-Bu | H | H | H |
| Me | 1,1'-bicyclopropyl-1-yl | n-Bu | H | H | H |
| Me | (1R,2S)-1,1'-bicyclopropyl-2-yl | n-Bu | H | H | H |

R$^1$ is NHR$^3$, R$^9$ and R$^{10}$ are taken together as —CH═N—CH═CH—, X is Br, and the metal cyanide is sodium cyanide.

| | | | | | |
|---|---|---|---|---|---|
| Me | H | (CH$_2$)$_4$NR$^9$R$^{10}$ | H | H | H |
| Me | Me | (CH$_2$)$_4$NR$^9$R$^{10}$ | H | H | H |
| Me | Et | (CH$_2$)$_4$NR$^9$R$^{10}$ | H | H | H |
| Me | n-Pr | (CH$_2$)$_4$NR$^9$R$^{10}$ | H | H | H |
| Me | i-Pr | (CH$_2$)$_4$NR$^9$R$^{10}$ | H | H | H |
| Me | n-Bu | (CH$_2$)$_4$NR$^9$R$^{10}$ | H | H | H |
| Me | i-Bu | (CH$_2$)$_4$NR$^9$R$^{10}$ | H | H | H |
| Me | s-Bu | (CH$_2$)$_4$NR$^9$R$^{10}$ | H | H | H |
| Me | t-Bu | (CH$_2$)$_4$NR$^9$R$^{10}$ | H | H | H |
| Me | c-Pr | (CH$_2$)$_4$NR$^9$R$^{10}$ | H | H | H |
| Me | c-PrCH$_2$ | (CH$_2$)$_4$NR$^9$R$^{10}$ | H | H | H |
| Me | 1-CH$_3$-c-Pr | (CH$_2$)$_4$NR$^9$R$^{10}$ | H | H | H |
| Me | 2-CH$_3$-c-Pr | (CH$_2$)$_4$NR$^9$R$^{10}$ | H | H | H |
| Me | 1,1'-bicyclopropyl-2-yl | (CH$_2$)$_4$NR$^9$R$^{10}$ | H | H | H |
| Me | 1,1'-bicyclopropyl-1-yl | (CH$_2$)$_4$NR$^9$R$^{10}$ | H | H | H |
| Me | (1R,2S)-1,1'-bicyclopropyl-2-yl | (CH$_2$)$_4$NR$^9$R$^{10}$ | H | H | H |

R$^1$ is NHR$^3$, R$^9$ and R$^{10}$ are taken together as —CH═N—CH═CH—, X is Br, and the metal cyanide is potassium cyanide.

| | | | | | |
|---|---|---|---|---|---|
| Me | H | (CH$_2$)$_4$NR$^9$R$^{10}$ | H | H | H |
| Me | Me | (CH$_2$)$_4$NR$^9$R$^{10}$ | H | H | H |
| Me | Et | (CH$_2$)$_4$NR$^9$R$^{10}$ | H | H | H |
| Me | n-Pr | (CH$_2$)$_4$NR$^9$R$^{10}$ | H | H | H |
| Me | i-Pr | (CH$_2$)$_4$NR$^9$R$^{10}$ | H | H | H |
| Me | n-Bu | (CH$_2$)$_4$NR$^9$R$^{10}$ | H | H | H |
| Me | i-Bu | (CH$_2$)$_4$NR$^9$R$^{10}$ | H | H | H |
| Me | s-Bu | (CH$_2$)$_4$NR$^9$R$^{10}$ | H | H | H |
| Me | t-Bu | (CH$_2$)$_4$NR$^9$R$^{10}$ | H | H | H |
| Me | c-Pr | (CH$_2$)$_4$NR$^9$R$^{10}$ | H | H | H |
| Me | c-PrCH$_2$ | (CH$_2$)$_4$NR$^9$R$^{10}$ | H | H | H |
| Me | 1-CH$_3$-c-Pr | (CH$_2$)$_4$NR$^9$R$^{10}$ | H | H | H |
| Me | 2-CH$_3$-c-Pr | (CH$_2$)$_4$NR$^9$R$^{10}$ | H | H | H |
| Me | 1,1'-bicyclopropyl-2-yl | (CH$_2$)$_4$NR$^9$R$^{10}$ | H | H | H |

TABLE 1-continued

| | | | | | |
|---|---|---|---|---|---|
| Me | 1,1'-bicyclopropyl-1-yl | $(CH_2)_4NR^9R^{10}$ | H | H | H |
| Me | (1R,2S)-1,1'-bicyclopropyl-2-yl | $(CH_2)_4NR^9R^{10}$ | H | H | H |

$R^1$ is $NHR^3$, $R^9$ and $R^{10}$ are taken together
as —CH=N—CH=CH—,
X is Br, and the metal cyanide is
potassium hexacyanoferrate(II).

| | | | | | |
|---|---|---|---|---|---|
| Me | H | $(CH_2)_4NR^9R^{10}$ | H | H | H |
| Me | Me | $(CH_2)_4NR^9R^{10}$ | H | H | H |
| Me | Et | $(CH_2)_4NR^9R^{10}$ | H | H | H |
| Me | n-Pr | $(CH_2)_4NR^9R^{10}$ | H | H | H |
| Me | i-Pr | $(CH_2)_4NR^9R^{10}$ | H | H | H |
| Me | n-Bu | $(CH_2)_4NR^9R^{10}$ | H | H | H |
| Me | i-Bu | $(CH_2)_4NR^9R^{10}$ | H | H | H |
| Me | s-Bu | $(CH_2)_4NR^9R^{10}$ | H | H | H |
| Me | t-Bu | $(CH_2)_4NR^9R^{10}$ | H | H | H |
| Me | c-Pr | $(CH_2)_4NR^9R^{10}$ | H | H | H |
| Me | c-PrCH$_2$ | $(CH_2)_4NR^9R^{10}$ | H | H | H |
| Me | 1-CH$_3$-c-Pr | $(CH_2)_4NR^9R^{10}$ | H | H | H |
| Me | 2-CH$_3$-c-Pr | $(CH_2)_4NR^9R^{10}$ | H | H | H |
| Me | 1,1'-bicyclopropyl-2-yl | $(CH_2)_4NR^9R^{10}$ | H | H | H |
| Me | 1,1'-bicyclopropyl-1-yl | $(CH_2)_4NR^9R^{10}$ | H | H | H |
| Me | (1R,2S)-1,1'-bicyclopropyl-2-yl | $(CH_2)_4NR^9R^{10}$ | H | H | H |

$R^1$ is $NHR^3$, $R^9$ and $R^{10}$ are taken together
as —CH=N—CH=CH—,
X is Br, and the metal cyanide is sodium cyanide.

| | | | | | |
|---|---|---|---|---|---|
| Me | H | $(CH_2)_5NR^9R^{10}$ | H | H | H |
| Me | Me | $(CH_2)_5NR^9R^{10}$ | H | H | H |
| Me | Me | $(CH_2)_6NR^9R^{10}$ | H | H | H |
| Me | Et | $(CH_2)_6NR^9R^{10}$ | H | H | H |
| Me | n-Pr | $(CH_2)_5NR^9R^{10}$ | H | H | H |
| Me | i-Pr | $(CH_2)_6NR^9R^{10}$ | H | H | H |
| Me | n-Bu | $(CH_2)_5NR^9R^{10}$ | H | H | H |
| Me | i-Bu | $(CH_2)_6NR^9R^{10}$ | H | H | H |
| Me | s-Bu | $(CH_2)_5NR^9R^{10}$ | H | H | H |
| Me | t-Bu | $(CH_2)_5NR^9R^{10}$ | H | H | H |
| Me | c-Pr | $(CH_2)_6NR^9R^{10}$ | H | H | H |
| Me | c-PrCH$_2$ | $(CH_2)_5NR^9R^{10}$ | H | H | H |
| Me | 1-CH$_3$-c-Pr | $(CH_2)_5NR^9R^{10}$ | H | H | H |
| Me | 2-CH$_3$-c-Pr | $(CH_2)_6NR^9R^{10}$ | H | H | H |
| Me | 1,1'-bicyclopropyl-2-yl | $(CH_2)_5NR^9R^{10}$ | H | H | H |
| Me | 1,1'-bicyclopropyl-1-yl | $(CH_2)_6NR^9R^{10}$ | H | H | H |
| Me | (1R,2S)-1,1'-bicyclopropyl-2-yl | $(CH_2)_5NR^9R^{10}$ | H | H | H |

$R^1$ is $NHR^3$, $R^9$ and $R^{10}$ are taken together
as —CH=N—CH=CH—,
X is Br, and the metal cyanide is potassium cyanide.

| | | | | | |
|---|---|---|---|---|---|
| Me | H | $(CH_2)_6NR^9R^{10}$ | H | H | H |
| Me | Me | $(CH_2)_6NR^9R^{10}$ | H | H | H |
| Me | Et | $(CH_2)_6NR^9R^{10}$ | H | H | H |
| Me | n-Pr | $(CH_2)_5NR^9R^{10}$ | H | H | H |
| Me | i-Pr | $(CH_2)_5NR^9R^{10}$ | H | H | H |
| Me | n-Bu | $(CH_2)_6NR^9R^{10}$ | H | H | H |
| Me | i-Bu | $(CH_2)_5NR^9R^{10}$ | H | H | H |
| Me | s-Bu | $(CH_2)_5NR^9R^{10}$ | H | H | H |
| Me | t-Bu | $(CH_2)_6NR^9R^{10}$ | H | H | H |
| Me | c-Pr | $(CH_2)_5NR^9R^{10}$ | H | H | H |
| Me | c-PrCH$_2$ | $(CH_2)_5NR^9R^{10}$ | H | H | H |
| Me | 1-CH$_3$-c-Pr | $(CH_2)_5NR^9R^{10}$ | H | H | H |
| Me | 2-CH$_3$-c-Pr | $(CH_2)_5NR^9R^{10}$ | H | H | H |
| Me | 1,1'-bicyclopropyl-2-yl | $(CH_2)_6NR^9R^{10}$ | H | H | H |
| Me | 1,1'-bicyclopropyl-1-yl | $(CH_2)_5NR^9R^{10}$ | H | H | H |
| Me | (1R,2S)-1,1'-bicyclopropyl-2-yl | $(CH_2)_6NR^9R^{10}$ | H | H | H |

$R^1$ is $NHR^3$, $R^9$ and $R^{10}$ are taken together
as —CH=N—CH=CH—,
X is Br, and the metal cyanide is
potassium hexacyanoferrate(II).

| | | | | | |
|---|---|---|---|---|---|
| Me | H | $(CH_2)_5NR^9R^{10}$ | H | H | H |
| Me | Me | $(CH_2)_5NR^9R^{10}$ | H | H | H |
| Me | Et | $(CH_2)_5NR^9R^{10}$ | H | H | H |
| Me | n-Pr | $(CH_2)_5NR^9R^{10}$ | H | H | H |
| Me | i-Pr | $(CH_2)_5NR^9R^{10}$ | H | H | H |
| Me | n-Bu | $(CH_2)_6NR^9R^{10}$ | H | H | H |
| Me | i-Bu | $(CH_2)_5NR^9R^{10}$ | H | H | H |
| Me | s-Bu | $(CH_2)_5NR^9R^{10}$ | H | H | H |
| Me | t-Bu | $(CH_2)_5NR^9R^{10}$ | H | H | H |
| Me | c-Pr | $(CH_2)_5NR^9R^{10}$ | H | H | H |
| Me | c-PrCH$_2$ | $(CH_2)_5NR^9R^{10}$ | H | H | H |
| Me | 1-CH$_3$-c-Pr | $(CH_2)_5NR^9R^{10}$ | H | H | H |
| Me | 2-CH$_3$-c-Pr | $(CH_2)_5NR^9R^{10}$ | H | H | H |
| Me | 1,1'-bicyclopropyl-2-yl | $(CH_2)_5NR^9R^{10}$ | H | H | H |
| Me | 1,1'-bicyclopropyl-1-yl | $(CH_2)_6NR^9R^{10}$ | H | H | H |
| Me | (1R,2S)-1,1'-bicyclopropyl-2-yl | $(CH_2)_5NR^9R^{10}$ | H | H | H |

$R^1$ is $NHR^3$, $R^9$ and $R^{10}$ are taken together
as —CH=N—CH=CH—,
X is Br, and the metal cyanide is sodium cyanide.

| | | | | | |
|---|---|---|---|---|---|
| Me | Me | Me | Me | H | H |
| Me | Me | Me | H | Me | H |
| Me | Me | H | H | Me | H |
| Me | Me | Me | H | H | Me |
| Me | Me | Me | H | Me | Me |
| Me | Me | Et | H | H | H |
| Me | Me | n-Pr | H | H | H |
| Me | Me | i-Pr | H | H | H |
| Me | Me | n-Bu | Me | H | H |
| Me | Me | n-Bu | H | Me | H |
| Me | Me | n-Bu | H | H | Me |
| Me | Me | n-Bu | H | Me | Me |
| Me | Me | s-Bu | H | H | H |
| Me | Me | i-Bu | H | H | H |
| Me | Me | t-Bu | H | H | H |
| Me | Me | n-pentyl | H | H | H |
| Me | Me | n-hexyl | H | H | H |
| Me | Me | n-heptyl | H | H | H |
| Me | Me | n-octyl | H | H | H |
| Me | Me | n-nonyl | H | H | H |
| Me | Me | n-decyl | H | H | H |
| Me | Me | n-decyl | Me | H | H |
| Me | Me | n-undecyl | H | H | H |
| Me | Me | n-dodecyl | H | H | H |
| Me | i-Pr | Me | H | H | H |
| Me | i-Pr | n-Bu | H | H | H |
| Me | i-Pr | $(CH_2)_4NR^9R^{10}$ | H | H | H |
| Me | i-Pr | $(CH_2)_5NR^9R^{10}$ | H | H | H |
| Me | i-Pr | $(CH_2)_6NR^9R^{10}$ | H | H | H |

$R^1$ is $NHR^3$, $R^9$ and $R^{10}$ are taken together
as —CH=N—CH=CH—,
X is Br, and the metal cyanide is potassium cyanide.

| | | | | | |
|---|---|---|---|---|---|
| Me | Me | Me | Me | H | H |
| Me | Me | Me | H | Me | H |
| Me | Me | Me | H | H | Me |
| Me | Me | Me | H | Me | Me |
| Me | Me | Et | H | H | H |
| Me | Me | n-Pr | H | H | H |
| Me | Me | i-Pr | H | H | H |
| Me | Me | n-Bu | Me | H | H |
| Me | Me | n-Bu | H | Me | H |
| Me | Me | n-Bu | H | H | Me |
| Me | Me | n-Bu | H | Me | Me |
| Me | Me | s-Bu | H | H | H |
| Me | Me | i-Bu | H | H | H |
| Me | Me | t-Bu | H | H | H |
| Me | Me | n-pentyl | H | H | H |
| Me | Me | n-hexyl | H | H | H |
| Me | Me | n-heptyl | H | H | H |
| Me | Me | n-octyl | H | H | H |
| Me | Me | n-nonyl | H | H | H |
| Me | Me | n-decyl | H | H | H |
| Me | Me | n-decyl | Me | H | H |
| Me | Me | n-undecyl | H | H | H |
| Me | Me | n-dodecyl | H | H | H |
| Me | i-Pr | Me | H | H | H |
| Me | i-Pr | n-Bu | H | H | H |
| Me | i-Pr | $(CH_2)_4NR^9R^{10}$ | H | H | H |

TABLE 1-continued

| R² | R⁴ | R⁵ | R⁶ | R⁷ | R⁸ |
|---|---|---|---|---|---|
| Me | i-Pr | (CH₂)₅NR⁹R¹⁰ | H | H | H |
| Me | i-Pr | (CH₂)₆NR⁹R¹⁰ | H | H | H |

$R^1$ is $NHR^3$, $R^9$ and $R^{10}$ are taken together
as —CH=N—CH=CH—,
X is Br, and the metal cyanide is
potassium hexacyanoferrate(II).

| R² | R⁴ | R⁵ | R⁶ | R⁷ | R⁸ |
|---|---|---|---|---|---|
| Me | Me | Me | Me | H | H |
| Me | Me | Me | H | Me | H |
| Me | Me | Me | H | H | Me |
| Me | Me | Me | H | Me | Me |
| Me | Me | Et | H | H | H |
| Me | Me | n-Pr | H | H | H |
| Me | Me | i-Pr | H | H | H |
| Me | Me | n-Bu | Me | H | H |
| Me | Me | n-Bu | H | Me | H |
| Me | Me | n-Bu | H | H | Me |
| Me | Me | n-Bu | H | Me | Me |
| Me | Me | s-Bu | H | H | H |
| Me | Me | i-Bu | H | H | H |
| Me | Me | t-Bu | H | H | H |
| Me | Me | n-pentyl | H | H | H |
| Me | Me | n-hexyl | H | H | H |
| Me | Me | n-heptyl | H | H | H |
| Me | Me | n-octyl | H | H | H |
| Me | Me | n-nonyl | H | H | H |
| Me | Me | n-decyl | H | H | H |
| Me | Me | n-decyl | Me | H | H |
| Me | Me | n-undecyl | H | H | H |
| Me | Me | n-dodecyl | H | H | H |
| Me | i-Pr | Me | H | H | H |
| Me | i-Pr | n-Bu | H | H | H |
| Me | i-Pr | (CH₂)₄NR⁹R¹⁰ | H | H | H |
| Me | i-Pr | (CH₂)₅NR⁹R¹⁰ | H | H | H |
| Me | i-Pr | (CH₂)₆NR⁹R¹⁰ | H | H | H |

$R^1$ is $NHR^3$, $R^9$ and $R^{10}$ are taken together
as —CH=N—CH=CH—,
X is Cl, and the metal cyanide is sodium cyanide.

| R² | R⁴ | R⁵ | R⁶ | R⁷ | R⁸ |
|---|---|---|---|---|---|
| Me | Me | Me | H | H | H |
| Me | Me | Et | H | H | H |
| Me | Me | n-Pr | H | H | H |
| Me | Me | n-Bu | H | H | H |
| Me | Me | (CH₂)₄NR⁹R¹⁰ | H | H | H |
| Me | i-Pr | Me | H | H | H |
| Me | i-Pr | (CH₂)₄NR⁹R¹⁰ | H | H | H |

$R^1$ is $NHR^3$, $R^9$ and $R^{10}$ are taken together
as —CH=N—CH=CH—,
X is Cl, and the metal cyanide is
potassium hexacyanoferrate(II).

| R² | R⁴ | R⁵ | R⁶ | R⁷ | R⁸ |
|---|---|---|---|---|---|
| Me | Me | Me | H | H | H |
| Me | Me | Et | H | H | H |
| Me | Me | n-Pr | H | H | H |
| Me | Me | n-Bu | H | H | H |
| Me | Me | (CH₂)₄NR⁹R¹⁰ | H | H | H |
| Me | i-Pr | Me | H | H | H |
| Me | i-Pr | (CH₂)₄NR⁹R¹⁰ | H | H | H |

$R^1$ is $NHR^3$, $R^9$ and $R^{10}$ are taken together
as —CH=N—CH=CH—,
X is Br, and the metal cyanide is sodium cyanide.

| R² | R⁴ | R⁵ | R⁶ | R⁷ | R⁸ |
|---|---|---|---|---|---|
| Cl | Me | Me | H | H | H |
| Cl | Me | Et | H | H | H |
| Cl | Me | n-Pr | H | H | H |
| Cl | Me | n-Bu | H | H | H |
| Cl | Me | (CH₂)₄NR⁹R¹⁰ | H | H | H |
| Cl | i-Pr | Me | H | H | H |
| Cl | i-Pr | (CH₂)₄NR⁹R¹⁰ | H | H | H |

$R^1$ is $OR^4$, $R^9$ and $R^{10}$ are taken together
as —CH=N—CH=CH—,
X is Br, and the metal cyanide is sodium cyanide.

| R² | R⁴ | R⁵ | R⁶ | R⁷ | R⁸ |
|---|---|---|---|---|---|
| Me | H | Me | H | H | H |
| Me | Me | Me | H | H | H |
| Me | Et | Me | H | H | H |
| Me | n-Pr | Me | H | H | H |
| Me | i-Pr | Me | H | H | H |
| Me | n-Bu | Me | H | H | H |
| Me | s-Bu | Me | H | H | H |
| Me | i-Bu | Me | H | H | H |
| Me | t-Bu | Me | H | H | H |
| Me | H | n-Bu | H | H | H |
| Me | Me | n-Bu | H | H | H |
| Me | Et | n-Bu | H | H | H |
| Me | n-Pr | n-Bu | H | H | H |
| Me | i-Pr | n-Bu | H | H | H |
| Me | n-Bu | n-Bu | H | H | H |
| Me | s-Bu | n-Bu | H | H | H |
| Me | i-Bu | n-Bu | H | H | H |
| Me | t-Bu | n-Bu | H | H | H |
| Me | H | (CH₂)₄NR⁹R¹⁰ | H | H | H |
| Me | Me | (CH₂)₄NR⁹R¹⁰ | H | H | H |
| Me | Et | (CH₂)₄NR⁹R¹⁰ | H | H | H |
| Me | n-Pr | (CH₂)₄NR⁹R¹⁰ | H | H | H |
| Me | i-Pr | (CH₂)₄NR⁹R¹⁰ | H | H | H |
| Me | n-Bu | (CH₂)₄NR⁹R¹⁰ | H | H | H |
| Me | s-Bu | (CH₂)₄NR⁹R¹⁰ | H | H | H |
| Me | i-Bu | (CH₂)₄NR⁹R¹⁰ | H | H | H |
| Me | t-Bu | (CH₂)₄NR⁹R¹⁰ | H | H | H |
| Me | H | (CH₂)₆NR⁹R¹⁰ | H | H | H |
| Me | Me | (CH₂)₅NR⁹R¹⁰ | H | H | H |
| Me | Et | (CH₂)₅NR⁹R¹⁰ | H | H | H |
| Me | n-Pr | (CH₂)₅NR⁹R¹⁰ | H | H | H |
| Me | i-Pr | (CH₂)₅NR⁹R¹⁰ | H | H | H |
| Me | n-Bu | (CH₂)₅NR⁹R¹⁰ | H | H | H |
| Me | s-Bu | (CH₂)₅NR⁹R¹⁰ | H | H | H |
| Me | i-Bu | (CH₂)₅NR⁹R¹⁰ | H | H | H |
| Me | t-Bu | (CH₂)₅NR⁹R¹⁰ | H | H | H |
| Me | H | (CH₂)₆NR⁹R¹⁰ | H | H | H |
| Me | Me | (CH₂)₆NR⁹R¹⁰ | H | H | H |
| Me | Et | (CH₂)₆NR⁹R¹⁰ | H | H | H |
| Me | n-Pr | (CH₂)₆NR⁹R¹⁰ | H | H | H |
| Me | i-Pr | (CH₂)₆NR⁹R¹⁰ | H | H | H |
| Me | n-Bu | (CH₂)₆NR⁹R¹⁰ | H | H | H |
| Me | s-Bu | (CH₂)₆NR⁹R¹⁰ | H | H | H |
| Me | i-Bu | (CH₂)₆NR⁹R¹⁰ | H | H | H |
| Me | t-Bu | (CH₂)₆NR⁹R¹⁰ | H | H | H |
| Cl | H | Me | H | H | H |
| Cl | Me | Me | H | H | H |
| Cl | Et | Me | H | H | H |
| Cl | n-Pr | Me | H | H | H |
| Cl | i-Pr | Me | H | H | H |
| Cl | n-Bu | Me | H | H | H |
| Cl | s-Bu | Me | H | H | H |
| Cl | i-Bu | Me | H | H | H |
| Cl | t-Bu | Me | H | H | H |
| Cl | H | n-Bu | H | H | H |
| Cl | Me | n-Bu | H | H | H |
| Cl | Et | n-Bu | H | H | H |
| Cl | n-Pr | n-Bu | H | H | H |
| Cl | i-Pr | n-Bu | H | H | H |
| Cl | n-Bu | n-Bu | H | H | H |
| Cl | s-Bu | n-Bu | H | H | H |
| Cl | i-Bu | n-Bu | H | H | H |
| Cl | t-Bu | n-Bu | H | H | H |
| Cl | H | (CH₂)₄NR⁹R¹⁰ | H | H | H |
| Cl | Me | (CH₂)₄NR⁹R¹⁰ | H | H | H |
| Cl | Et | (CH₂)₄NR⁹R¹⁰ | H | H | H |
| Cl | n-Pr | (CH₂)₄NR⁹R¹⁰ | H | H | H |
| Cl | i-Pr | (CH₂)₄NR⁹R¹⁰ | H | H | H |
| Cl | n-Bu | (CH₂)₄NR⁹R¹⁰ | H | H | H |
| Cl | s-Bu | (CH₂)₄NR⁹R¹⁰ | H | H | H |
| Cl | i-Bu | (CH₂)₄NR⁹R¹⁰ | H | H | H |
| Cl | t-Bu | (CH₂)₄NR⁹R¹⁰ | H | H | H |
| Cl | H | (CH₂)₄NR⁹R¹⁰ | H | H | H |
| Cl | Me | (CH₂)₆NR⁹R¹⁰ | H | H | H |
| Cl | Et | (CH₂)₅NR⁹R¹⁰ | H | H | H |
| Cl | n-Pr | (CH₂)₅NR⁹R¹⁰ | H | H | H |

TABLE 1-continued

| | | | | | |
|---|---|---|---|---|---|
| Cl | i-Pr | (CH$_2$)$_5$NR$^9$R$^{10}$ | H | H | H |
| Cl | n-Bu | (CH$_2$)$_5$NR$^9$R$^{10}$ | H | H | H |
| Cl | s-Bu | (CH$_2$)$_5$NR$^9$R$^{10}$ | H | H | H |
| Cl | i-Bu | (CH$_2$)$_5$NR$^9$R$^{10}$ | H | H | H |
| Cl | t-Bu | (CH$_2$)$_5$NR$^9$R$^{10}$ | H | H | H |
| Cl | H | (CH$_2$)$_6$NR$^9$R$^{10}$ | H | H | H |
| Cl | Me | (CH$_2$)$_6$NR$^9$R$^{10}$ | H | H | H |
| Cl | Et | (CH$_2$)$_6$NR$^9$R$^{10}$ | H | H | H |
| Cl | n-Pr | (CH$_2$)$_6$NR$^9$R$^{10}$ | H | H | H |
| Cl | i-Pr | (CH$_2$)$_6$NR$^9$R$^{10}$ | H | H | H |
| Cl | n-Bu | (CH$_2$)$_6$NR$^9$R$^{10}$ | H | H | H |
| Cl | s-Bu | (CH$_2$)$_6$NR$^9$R$^{10}$ | H | H | H |
| Cl | i-Bu | (CH$_2$)$_6$NR$^9$R$^{10}$ | H | H | H |
| Cl | t-Bu | (CH$_2$)$_6$NR$^9$R$^{10}$ | H | H | H |

R$^1$ is OR$^4$, X is Br, and the metal cyanide is potassium cyanide.

| | | | | | |
|---|---|---|---|---|---|
| Me | Me | Me | Me | H | H |
| Me | Me | Me | H | Me | H |
| Me | Me | Me | H | H | Me |
| Me | Me | Me | H | Me | Me |
| Me | Me | Et | H | H | H |
| Me | Me | n-Pr | H | H | H |
| Me | Me | i-Pr | H | H | H |
| Me | Me | n-Bu | Me | H | H |
| Me | Me | n-Bu | H | Me | H |
| Me | Me | n-Bu | H | H | Me |
| Me | Me | n-Bu | H | Me | Me |
| Me | Me | s-Bu | H | H | H |
| Me | Me | i-Bu | H | H | H |
| Me | Me | t-Bu | H | H | H |
| Me | Me | n-pentyl | H | H | H |
| Me | Me | n-hexyl | H | H | H |
| Me | Me | n-heptyl | H | H | H |
| Me | Me | n-octyl | H | H | H |
| Me | Me | n-nonyl | H | H | H |
| Me | Me | n-decyl | H | H | H |
| Me | Me | n-decyl | Me | H | H |
| Me | Me | n-undecyl | H | H | H |
| Me | Me | n-dodecyl | H | H | H |
| Me | Et | Et | H | H | H |
| Me | Et | n-Pr | H | H | H |
| Me | Et | i-Pr | H | H | H |
| Me | Et | n-Bu | Me | H | H |
| Me | Et | n-Bu | H | Me | H |
| Me | Et | n-Bu | H | H | Me |
| Me | Et | n-Bu | H | Me | Me |
| Me | Et | s-Bu | H | H | H |
| Me | Et | i-Bu | H | H | H |
| Me | Et | t-Bu | H | H | H |
| Me | Et | n-pentyl | H | H | H |
| Me | Et | n-hexyl | H | H | H |
| Me | Et | n-heptyl | H | H | H |
| Me | Et | n-octyl | H | H | H |
| Me | Et | n-nonyl | H | H | H |
| Me | Et | n-decyl | H | H | H |
| Me | Et | n-decyl | Me | H | H |
| Me | Et | n-undecyl | H | H | H |
| Me | Et | n-dodecyl | H | H | H |
| Me | n-Pr | Et | H | H | H |
| Me | n-Pr | n-Pr | H | H | H |
| Me | n-Pr | i-Pr | H | H | H |
| Me | n-Pr | n-Bu | Me | H | H |
| Me | n-Pr | n-Bu | H | Me | H |
| Me | n-Pr | n-Bu | H | H | Me |
| Me | n-Pr | n-Bu | H | Me | Me |
| Me | i-Pr | Et | H | H | H |
| Me | i-Pr | n-Pr | H | H | H |
| Me | i-Pr | i-Pr | H | H | H |
| Me | i-Pr | n-Bu | Me | H | H |
| Me | i-Pr | n-Bu | H | Me | H |
| Me | i-Pr | n-Bu | H | H | Me |
| Me | i-Pr | n-Bu | H | Me | Me |

R$^1$ is OR$^4$, X is Br, and the metal cyanide is potassium hexacyanoferrate(II).

| | | | | | |
|---|---|---|---|---|---|
| Me | Me | Me | Me | H | H |
| Me | Me | Me | H | Me | H |

Table 2 illustrates particular transformations to prepare compounds of Formula 4 from compounds of Formula 2 according to a method of the present invention. Conversion of the compound of Formula 1 to the compound of Formula 4 can, for example, be accomplished according to the method of Scheme 6 using a sulfonyl chloride such as methanesulfonyl chloride in the presence of a solvent such as acetonitrile and a base such as 3-picoline. For these transformations, the metal cyanide reagent is sodium cyanide, the copper(I) salt reagent and the iodide salt reagent are copper(I) iodide, and the compound of Formula 3 is 1-methyl-1H-imidazole (i.e. R$^5$ is Me, R$^6$, R$^7$ and R$^8$ are H).

TABLE 2

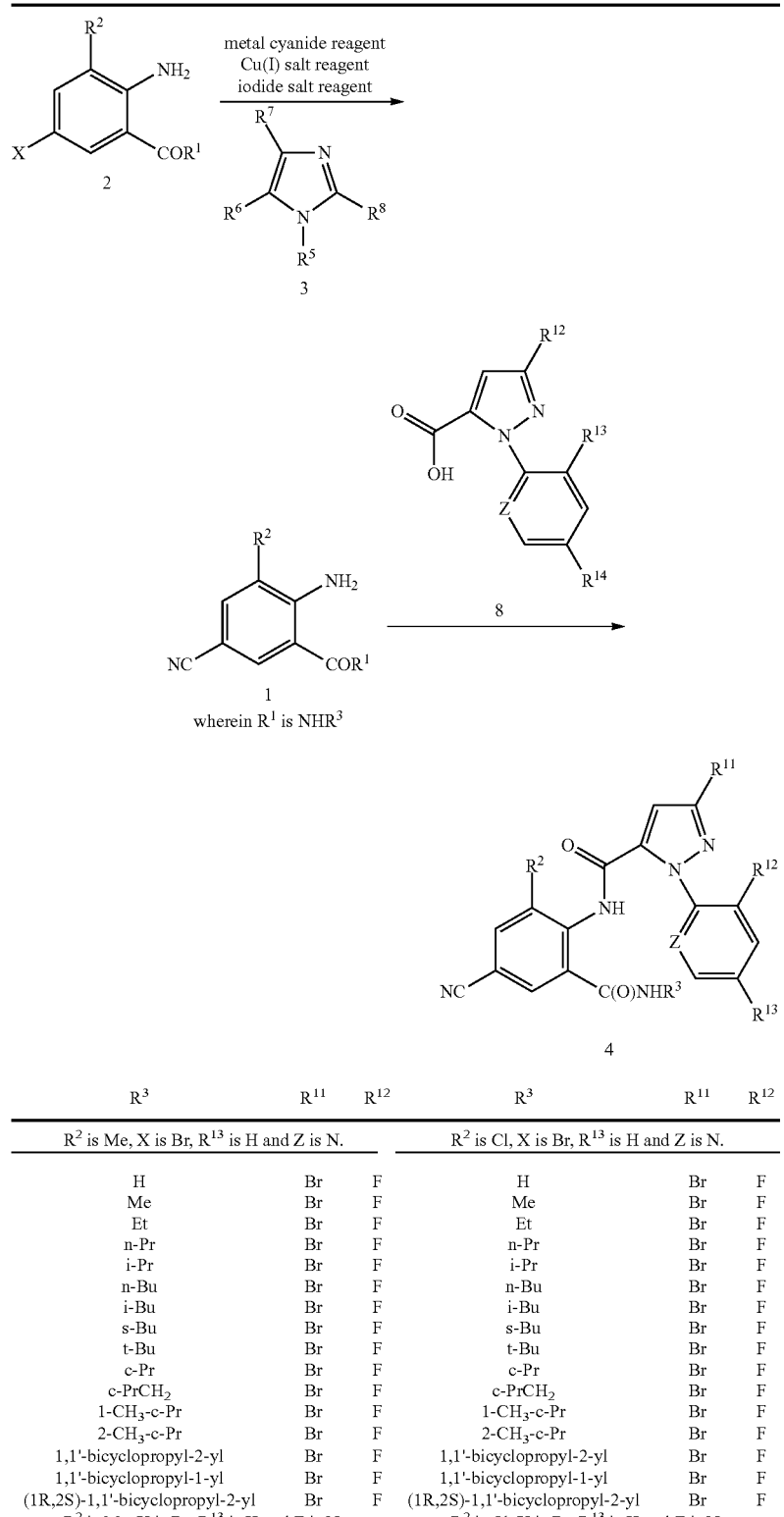

| R³ | R¹¹ | R¹² | R³ | R¹¹ | R¹² |
|---|---|---|---|---|---|
| R² is Me, X is Br, R¹³ is H and Z is N. | | | R² is Cl, X is Br, R¹³ is H and Z is N. | | |
| H | Br | F | H | Br | F |
| Me | Br | F | Me | Br | F |
| Et | Br | F | Et | Br | F |
| n-Pr | Br | F | n-Pr | Br | F |
| i-Pr | Br | F | i-Pr | Br | F |
| n-Bu | Br | F | n-Bu | Br | F |
| i-Bu | Br | F | i-Bu | Br | F |
| s-Bu | Br | F | s-Bu | Br | F |
| t-Bu | Br | F | t-Bu | Br | F |
| c-Pr | Br | F | c-Pr | Br | F |
| c-PrCH₂ | Br | F | c-PrCH₂ | Br | F |
| 1-CH₃-c-Pr | Br | F | 1-CH₃-c-Pr | Br | F |
| 2-CH₃-c-Pr | Br | F | 2-CH₃-c-Pr | Br | F |
| 1,1'-bicyclopropyl-2-yl | Br | F | 1,1'-bicyclopropyl-2-yl | Br | F |
| 1,1'-bicyclopropyl-1-yl | Br | F | 1,1'-bicyclopropyl-1-yl | Br | F |
| (1R,2S)-1,1'-bicylopropyl-2-yl | Br | F | (1R,2S)-1,1'-bicylopropyl-2-yl | Br | F |
| R² is Me, X is Br, R¹³ is H and Z is N. | | | R² is Cl, X is Br, R¹³ is H and Z is N. | | |
| H | Br | Cl | H | Br | Cl |
| Me | Br | Cl | Me | Br | Cl |
| Et | Br | Cl | Et | Br | Cl |
| n-Pr | Br | Cl | n-Pr | Br | Cl |
| i-Pr | Br | Cl | i-Pr | Br | Cl |
| n-Bu | Br | Cl | n-Bu | Br | Cl |

TABLE 2-continued

| | | | | | |
|---|---|---|---|---|---|
| i-Bu | Br | Cl | i-Bu | Br | Cl |
| s-Bu | Br | Cl | s-Bu | Br | Cl |
| t-Bu | Br | Cl | t-Bu | Br | Cl |
| c-Pr | Br | Cl | c-Pr | Br | Cl |
| c-PrCH$_2$ | Br | Cl | c-PrCH$_2$ | Br | Cl |
| 1-CH$_3$-c-Pr | Br | Cl | 1-CH$_3$-c-Pr | Br | Cl |
| 2-CH$_3$-c-Pr | Br | Cl | 2-CH$_3$-c-Pr | Br | Cl |
| 1,1'-bicyclopropyl-2-yl | Br | Cl | 1,1'-bicyclopropyl-2-yl | Br | Cl |
| 1,1'-bicyclopropyl-1-yl | Br | Cl | 1,1'-bicyclopropyl-1-yl | Br | Cl |
| (1R,2R)-1,1'-bicyclopropyl-2-yl | Br | Cl | (1R,2R)-1,1'-bicyclopropyl-2-yl | Br | Cl |
| H | Br | Br | H | Br | Br |
| Me | Br | Br | Me | Br | Br |
| Et | Br | Br | Et | Br | Br |
| n-Pr | Br | Br | n-Pr | Br | Br |
| i-Pr | Br | Br | i-Pr | Br | Br |
| n-Bu | Br | Br | n-Bu | Br | Br |
| i-Bu | Br | Br | i-Bu | Br | Br |
| s-Bu | Br | Br | s-Bu | Br | Br |
| t-Bu | Br | Br | t-Bu | Br | Br |
| c-Pr | Br | Br | c-Pr | Br | Br |
| c-PrCH$_2$ | Br | Br | c-PrCH$_2$ | Br | Br |
| 1-CH$_3$-c-Pr | Br | Br | 1-CH$_3$-c-Pr | Br | Br |
| 2-CH$_3$-c-Pr | Br | Br | 2-CH$_3$-c-Pr | Br | Br |
| 1,1'-bicyclopropyl-2-yl | Br | Br | 1,1'-bicyclopropyl-2-yl | Br | Br |
| 1,1'-bicyclopropyl-1-yl | Br | Br | 1,1'-bicyclopropyl-1-yl | Br | Br |
| H | Cl | F | H | Cl | F |
| Me | Cl | F | Me | Cl | F |
| Et | Cl | F | Et | Cl | F |
| n-Pr | Cl | F | n-Pr | Cl | F |
| i-Pr | Cl | F | i-Pr | Cl | F |
| R$^2$ is Me, X is Br, R$^{13}$ is H and Z is N. | | | R$^2$ is Cl, X is Br, R$^{13}$ is H and Z is N. | | |
| n-Bu | Cl | F | n-Bu | Cl | F |
| i-Bu | Cl | F | i-Bu | Cl | F |
| s-Bu | Cl | F | s-Bu | Cl | F |
| t-Bu | Cl | F | t-Bu | Cl | F |
| c-Pr | Cl | F | c-Pr | Cl | F |
| c-PrCH$_2$ | Cl | F | c-PrCH$_2$ | Cl | F |
| 1-CH$_3$-c-Pr | Cl | F | 1-CH$_3$-c-Pr | Cl | F |
| 2-CH$_3$-c-Pr | Cl | F | 2-CH$_3$-c-Pr | Cl | F |
| 1,1'-bicyclopropyl-2-yl | Cl | F | 1,1'-bicyclopropyl-2-yl | Cl | F |
| 1,1'-bicyclopropyl-1-yl | Cl | F | 1,1'-bicyclopropyl-1-yl | Cl | F |
| (1S,2R)-1,1'-bicyclopropyl-2-yl | Cl | F | (1S,2R)-1,1'-bicyclopropyl-2-yl | Cl | F |
| H | Cl | Cl | H | Cl | Cl |
| Me | Cl | Cl | Me | Cl | Cl |
| Et | Cl | Cl | Et | Cl | Cl |
| n-Pr | Cl | Cl | n-Pr | Cl | Cl |
| i-Pr | Cl | Cl | i-Pr | Cl | Cl |
| n-Bu | Cl | Cl | n-Bu | Cl | Cl |
| i-Bu | Cl | Cl | i-Bu | Cl | Cl |
| s-Bu | Cl | Cl | s-Bu | Cl | Cl |
| t-Bu | Cl | Cl | t-Bu | Cl | Cl |
| c-Pr | Cl | Cl | c-Pr | Cl | Cl |
| c-PrCH$_2$ | Cl | Cl | c-PrCH$_2$ | Cl | Cl |
| 1-CH$_3$-c-Pr | Cl | Cl | 1-CH$_3$-c-Pr | Cl | Cl |
| 2-CH$_3$-c-Pr | Cl | Cl | 2-CH$_3$-c-Pr | Cl | Cl |
| 1,1'-bicyclopropyl-2-yl | Cl | Cl | 1,1'-bicyclopropyl-2-yl | Cl | Cl |
| 1,1'-bicyclopropyl-1-yl | Cl | Cl | 1,1'-bicyclopropyl-1-yl | Cl | Cl |
| (1R,2R)-1,1'-bicyclopropyl-2-yl | Cl | Cl | (1R,2R)-1,1'-bicyclopropyl-2-yl | Cl | Cl |
| H | Cl | Br | H | Cl | Br |
| Me | Cl | Br | Me | Cl | Br |
| Et | Cl | Br | Et | Cl | Br |
| n-Pr | Cl | Br | n-Pr | Cl | Br |
| i-Pr | Cl | Br | i-Pr | Cl | Br |
| n-Bu | Cl | Br | n-Bu | Cl | Br |
| i-Bu | Cl | Br | i-Bu | Cl | Br |
| s-Bu | Cl | Br | s-Bu | Cl | Br |
| t-Bu | Cl | Br | t-Bu | Cl | Br |
| R$^2$ is Me, X is Br, R$^{13}$ is H and Z is N. | | | R$^2$ is Cl, X is Br, R$^{13}$ is H and Z is N. | | |
| c-Pr | Cl | Br | c-Pr | Cl | Br |
| c-PrCH$_2$ | Cl | Br | c-PrCH$_2$ | Cl | Br |
| 1-CH$_3$-c-Pr | Cl | Br | 1-CH$_3$-c-Pr | Cl | Br |
| 2-CH$_3$-c-Pr | Cl | Br | 2-CH$_3$-c-Pr | Cl | Br |
| 1,1'-bicyclopropyl-2-yl | Cl | Br | 1,1'-bicyclopropyl-2-yl | Cl | Br |
| 1,1'-bicyclopropyl-1-yl | Cl | Br | 1,1'-bicyclopropyl-1-yl | Cl | Br |
| H | CF$_3$ | F | H | CF$_3$ | F |
| Me | CF$_3$ | F | Me | CF$_3$ | F |
| t-Bu | CF$_3$ | F | t-Bu | CF$_3$ | F |
| 1-CH$_3$-c-Pr | CF$_3$ | F | 1-CH$_3$-c-Pr | CF$_3$ | F |

TABLE 2-continued

| | | | | | |
|---|---|---|---|---|---|
| 2-CH$_3$-c-Pr | CF$_3$ | F | 2-CH$_3$-c-Pr | CF$_3$ | F |
| 1,1'-bicyclopropyl-1-yl | CF$_3$ | F | 1,1'-bicyclopropyl-1-yl | CF$_3$ | F |
| (1R,2S)-1,1'-bicyclopropyl-2-yl | CF$_3$ | F | (1R,2S)-1,1'-bicyclopropyl-2-yl | CF$_3$ | F |
| H | CF$_3$ | Cl | H | CF$_3$ | Cl |
| Me | CF$_3$ | Cl | Me | CF$_3$ | Cl |
| t-Bu | CF$_3$ | Cl | t-Bu | CF$_3$ | Cl |
| 1-CH$_3$-c-Pr | CF$_3$ | Cl | 1-CH$_3$-c-Pr | CF$_3$ | Cl |
| 2-CH$_3$-c-Pr | CF$_3$ | Cl | 2-CH$_3$-c-Pr | CF$_3$ | Cl |
| 1,1'-bicyclopropyl-2-yl | CF$_3$ | Cl | 1,1'-bicyclopropyl-2-yl | CF$_3$ | Cl |
| 1,1'-bicyclopropyl-1-yl | CF$_3$ | Cl | 1,1'-bicyclopropyl-1-yl | CF$_3$ | Cl |
| H | CF$_3$ | Br | H | CF$_3$ | Br |
| Me | CF$_3$ | Br | Me | CF$_3$ | Br |
| t-Bu | CF$_3$ | Br | t-Bu | CF$_3$ | Br |
| 1-CH$_3$-c-Pr | CF$_3$ | Br | 1-CH$_3$-c-Pr | CF$_3$ | Br |
| 2-CH$_3$-c-Pr | CF$_3$ | Br | 2-CH$_3$-c-Pr | CF$_3$ | Br |
| 1,1'-bicyclopropyl-2-yl | CF$_3$ | Br | 1,1'-bicyclopropyl-2-yl | CF$_3$ | Br |
| H | OCH$_2$CF$_3$ | F | H | OCH$_2$CF$_3$ | F |
| Me | OCH$_2$CF$_3$ | F | Me | OCH$_2$CF$_3$ | F |
| t-Bu | OCH$_2$CF$_3$ | F | t-Bu | OCH$_2$CF$_3$ | F |
| 1,1'-bicyclopropyl-1-yl | OCH$_2$CF$_3$ | F | 1,1'-bicyclopropyl-1-yl | OCH$_2$CF$_3$ | F |
| H | OCH$_2$CF$_3$ | Cl | H | OCH$_2$CF$_3$ | Cl |
| Me | OCH$_2$CF$_3$ | Cl | Me | OCH$_2$CF$_3$ | Cl |
| t-Bu | OCH$_2$CF$_3$ | Cl | t-Bu | OCH$_2$CF$_3$ | Cl |
| 1,1'-bicyclopropyl-1-yl | OCH$_2$CF$_3$ | Cl | 1,1'-bicyclopropyl-1-yl | OCH$_2$CF$_3$ | Cl |
| H | OCH$_2$CF$_3$ | Br | H | OCH$_2$CF$_3$ | Br |
| Me | OCH$_2$CF$_3$ | Br | Me | OCH$_2$CF$_3$ | Br |
| R$^2$ is Me, X is Br, R$^{13}$ is H and Z is N. | | | R$^2$ is Cl, X is Br, R$^{13}$ is H and Z is N. | | |
| t-Bu | OCH$_2$CF$_3$ | Br | t-Bu | OCH$_2$CF$_3$ | Br |
| 1,1'-bicyclopropyl-1-yl | OCH$_2$CF$_3$ | Br | 1,1'-bicyclopropyl-1-yl | OCH$_2$CF$_3$ | Br |
| H | OCF$_2$H | F | H | OCF$_2$H | F |
| Me | OCF$_2$H | F | Me | OCF$_2$H | F |
| t-Bu | OCF$_2$H | F | t-Bu | OCF$_2$H | F |
| 1,1'-bicyclopropyl-2-yl | OCF$_2$H | F | 1,1'-bicyclopropyl-2-yl | OCF$_2$H | F |
| H | OCF$_2$H | Cl | H | OCF$_2$H | Cl |
| Me | OCF$_2$H | Cl | Me | OCF$_2$H | Cl |
| t-Bu | OCF$_2$H | Cl | t-Bu | OCF$_2$H | Cl |
| 1,1'-bicyclopropyl-1-yl | OCF$_2$H | Cl | 1,1'-bicyclopropyl-1-yl | OCF$_2$H | Cl |
| H | OCF$_2$H | Br | H | OCF$_2$H | Br |
| Me | OCF$_2$H | Br | Me | OCF$_2$H | Br |
| t-Bu | OCF$_2$H | Br | t-Bu | OCF$_2$H | Br |
| R$^2$ is Me, X is Br, R$^{13}$ is H and Z is CH. | | | R$^2$ is Cl, X is Br, R$^{13}$ is H and Z is CH. | | |
| H | Br | F | H | Br | F |
| Me | Br | F | Me | Br | F |
| t-Bu | Br | F | t-Bu | Br | F |
| c-Pr | Br | F | c-Pr | Br | F |
| c-PrCH$_2$ | Br | F | c-PrCH$_2$ | Br | F |
| 1,1'-bicyclopropyl-2-yl | Br | F | 1,1'-bicyclopropyl-2-yl | Br | F |
| 1,1'-bicyclopropyl-1-yl | Br | F | 1,1'-bicyclopropyl-1-yl | Br | F |
| (1R,2S)-1,1'-bicyclopropyl-2-yl | Br | F | (1R,2S)-1,1'-bicyclopropyl-2-yl | Br | F |
| (1R,2R)-1,1'-bicyclopropyl-2-yl | Br | F | (1R,2R)-1,1'-bicyclopropyl-2-yl | Br | F |
| H | Br | Cl | H | Br | Cl |
| Me | Br | Cl | Me | Br | Cl |
| t-Bu | Br | Cl | t-Bu | Br | Cl |
| c-Pr | Br | Cl | c-Pr | Br | Cl |
| c-PrCH$_2$ | Br | Cl | c-PrCH$_2$ | Br | Cl |
| 1,1'-bicyclopropyl-2-yl | Br | Cl | 1,1'-bicyclopropyl-2-yl | Br | Cl |
| 1,1'-bicyclopropyl-1-yl | Br | Cl | 1,1'-bicyclopropyl-1-yl | Br | Cl |
| H | Br | Br | H | Br | Br |
| Me | Br | Br | Me | Br | Br |
| t-Bu | Br | Br | t-Bu | Br | Br |
| c-Pr | Br | Br | c-Pr | Br | Br |
| R$^2$ is Me, X is Br, R$^{13}$ is H and Z is CH. | | | R$^2$ is Cl, X is Br, R$^{13}$ is H and Z is CH. | | |
| c-PrCH$_2$ | Br | Br | c-PrCH$_2$ | Br | Br |
| 1,1'-bicyclopropyl-2-yl | Br | Br | 1,1'-bicyclopropyl-2-yl | Br | Br |
| 1,1'-bicyclopropyl-1-yl | Br | Br | 1,1'-bicyclopropyl-1-yl | Br | Br |
| H | Cl | F | H | Cl | F |
| Me | Cl | F | Me | Cl | F |
| t-Bu | Cl | F | t-Bu | Cl | F |
| c-Pr | Cl | F | c-Pr | Cl | F |
| c-PrCH$_2$ | Cl | F | c-PrCH$_2$ | Cl | F |
| 1,1'-bicyclopropyl-2-yl | Cl | F | 1,1'-bicyclopropyl-2-yl | Cl | F |
| 1,1'-bicyclopropyl-1-yl | Cl | F | 1,1'-bicyclopropyl-1-yl | Cl | F |
| (1R,2R)-1,1'-bicyclopropyl-2-yl | Cl | F | (1R,2R)-1,1'-bicyclopropyl-2-yl | Cl | F |
| H | Cl | Cl | H | Cl | Cl |
| Me | Cl | Cl | Me | Cl | Cl |
| t-Bu | Cl | Cl | t-Bu | Cl | Cl |
| c-Pr | Cl | Cl | c-Pr | Cl | Cl |

TABLE 2-continued

| | | | | | |
|---|---|---|---|---|---|
| c-PrCH₂ | Cl | Cl | c-PrCH₂ | Cl | Cl |
| 1,1'-bicyclopropyl-2-yl | Cl | Cl | 1,1'-bicyclopropyl-2-yl | Cl | Cl |
| 1,1'-bicyclopropyl-1-yl | Cl | Cl | 1,1'-bicyclopropyl-1-yl | Cl | Cl |
| (1S,2R)-1,1'-bicyclopropyl-2-yl | Cl | Cl | (1S,2R)-1,1'-bicyclopropyl-2-yl | Cl | Cl |
| H | Cl | Br | H | Cl | Br |
| Me | Cl | Br | Me | Cl | Br |
| t-Bu | Cl | Br | t-Bu | Cl | Br |
| c-Pr | Cl | Br | c-Pr | Cl | Br |
| c-PrCH₂ | Cl | Br | c-PrCH₂ | Cl | Br |
| 1,1'-bicyclopropyl-2-yl | Cl | Br | 1,1'-bicyclopropyl-2-yl | Cl | Br |
| 1,1'-bicyclopropyl-1-yl | Cl | Br | 1,1'-bicyclopropyl-1-yl | Cl | Br |
| H | CF₃ | F | H | CF₃ | F |
| Me | CF₃ | F | Me | CF₃ | F |
| t-Bu | CF₃ | F | t-Bu | CF₃ | F |
| 2-CH₃-c-Pr | CF₃ | F | c-Pr | CF₃ | F |
| 1,1'-bicyclopropyl-2-yl | CF₃ | F | 1,1'-bicyclopropyl-2-yl | CF₃ | F |
| H | CF₃ | Cl | H | CF₃ | Cl |
| Me | CF₃ | Cl | Me | CF₃ | Cl |
| t-Bu | CF₃ | Cl | t-Bu | CF₃ | Cl |
| Me | CF₃ | Cl | Me | CF₃ | Br |
| Et | CF₃ | Br | Et | CF₃ | Br |
| $R^2$ is Me, X is Br, $R^{13}$ is H and Z is CH. | | | $R^2$ is Cl, X is Br, $R^{13}$ is H and Z is CH. | | |
| c-Pr | CF₃ | Br | c-Pr | CF₃ | Br |
| c-PrCH₂ | CF₃ | Br | c-PrCH₂ | CF₃ | Br |
| 1,1'-bicyclopropyl-2-yl | CF₃ | Br | 1,1'-bicyclopropyl-2-yl | CF₃ | Br |
| Me | OCH₂CF₃ | F | Me | OCH₂CF₃ | F |
| Et | OCH₂CF₃ | F | Et | OCH₂CF₃ | F |
| c-Pr | OCH₂CF₃ | F | c-Pr | OCH₂CF₃ | Cl |
| c-PrCH₂ | OCH₂CF₃ | Cl | c-PrCH₂ | OCH₂CF₃ | Cl |
| 1,1'-bicyclopropyl-2-yl | OCH₂CF₃ | Cl | 1,1'-bicyclopropyl-2-yl | OCH₂CF₃ | Cl |
| Me | OCH₂CF₃ | Br | Me | OCH₂CF₃ | Br |
| Et | OCH₂CF₃ | Br | Et | OCH₂CF₃ | Br |
| Me | OCF₂H | F | Me | OCF₂H | F |
| Et | OCF₂H | F | Et | OCF₂H | F |
| c-Pr | OCF₂H | Cl | c-Pr | OCF₂H | Cl |
| c-PrCH₂ | OCF₂H | Cl | c-PrCH₂ | OCF₂H | Cl |
| 1,1'-bicyclopropyl-2-yl | OCF₂H | Cl | 1,1'-bicyclopropyl-2-yl | OCF₂H | Cl |
| Me | OCF₂H | Br | Me | OCF₂H | Br |
| Et | OCF₂H | Br | Et | OCF₂H | Br |
| $R^2$ is Me, X is Br, $R^{13}$ is F and Z is N. | | | $R^2$ is Cl, X is Br, $R^{13}$ is F and Z is N. | | |
| H | Br | F | H | Br | F |
| Me | Br | F | Me | Br | F |
| t-Bu | Br | F | t-Bu | Br | F |
| c-Pr | Br | F | c-Pr | Br | F |
| c-PrCH₂ | Br | F | c-PrCH₂ | Br | F |
| 1,1'-bicyclopropyl-2-yl | Br | F | 1,1'-bicyclopropyl-2-yl | Br | F |
| 1,1'-bicyclopropyl-1-yl | Br | F | 1,1'-bicyclopropyl-1-yl | Br | F |
| H | Br | Cl | H | Br | Cl |
| Me | Br | Cl | Me | Br | Cl |
| t-Bu | Br | Cl | t-Bu | Br | Cl |
| c-Pr | Br | Cl | c-Pr | Br | Cl |
| c-PrCH₂ | Br | Cl | c-PrCH₂ | Br | Cl |
| 1,1'-bicyclopropyl-1-yl | Br | Cl | 1,1'-bicyclopropyl-1-yl | Br | Cl |
| H | Br | Br | H | Br | Br |
| Me | Br | Br | Me | Br | Br |
| t-Bu | Br | Br | t-Bu | Br | Br |
| $R^2$ is Me, X is Br, $R^{13}$ is F and Z is N. | | | $R^2$ is Cl, X is Br, $R^{13}$ is F and Z is N. | | |
| c-Pr | Br | Br | c-Pr | Br | Br |
| c-PrCH₂ | Br | Br | c-PrCH₂ | Br | Br |
| 1,1'-bicyclopropyl-1-yl | Br | Br | 1,1'-bicyclopropyl-1-yl | Br | Br |
| (1R,2S)-1,1'-bicyclopropyl-2-yl | Br | Br | (1R,2S)-1,1'-bicyclopropyl-2-yl | Br | Br |
| H | Cl | F | H | Cl | F |
| Me | Cl | F | Me | Cl | F |
| t-Bu | Cl | F | t-Bu | Cl | F |
| c-Pr | Cl | F | c-Pr | Cl | F |
| c-PrCH₂ | Cl | F | c-PrCH₂ | Cl | F |
| 1,1'-bicyclopropyl-2-yl | Cl | F | 1,1'-bicyclopropyl-2-yl | Cl | F |
| H | Cl | Cl | H | Cl | Cl |
| Me | Cl | Cl | Me | Cl | Cl |
| t-Bu | Cl | Cl | t-Bu | Cl | Cl |
| c-Pr | Cl | Cl | c-Pr | Cl | Cl |
| c-PrCH₂ | Cl | Cl | c-PrCH₂ | Cl | Cl |
| 1,1'-bicyclopropyl-1-yl | Cl | Cl | 1,1'-bicyclopropyl-1-yl | Cl | Cl |
| H | Cl | Br | H | Cl | Br |
| Me | Cl | Br | Me | Cl | Br |
| t-Bu | Cl | Br | t-Bu | Cl | Br |
| c-Pr | Cl | Br | c-Pr | Cl | Br |

TABLE 2-continued

| | | | | | |
|---|---|---|---|---|---|
| c-PrCH₂ | Cl | Br | c-PrCH₂ | Cl | Br |
| 1,1'-bicyclopropyl-2-yl | Cl | Br | 1,1'-bicyclopropyl-2-yl | Cl | Br |
| 1,1'-bicyclopropyl-1-yl | Cl | Br | 1,1'-bicyclopropyl-1-yl | Cl | Br |
| H | CF₃ | F | H | CF₃ | F |
| Me | CF₃ | F | Me | CF₃ | F |
| t-Bu | CF₃ | F | t-Bu | CF₃ | F |
| 2-CH₃-c-Pr | CF₃ | F | c-Pr | CF₃ | F |
| 1,1'-bicyclopropyl-2-yl | CF₃ | F | 1,1'-bicyclopropyl-2-yl | CF₃ | F |
| H | CF₃ | Cl | H | CF₃ | Cl |
| Me | CF₃ | Cl | Me | CF₃ | Cl |
| t-Bu | CF₃ | Cl | t-Bu | CF₃ | Cl |
| Me | CF₃ | Br | Me | CF₃ | Br |
| Et | CF₃ | Br | Et | CF₃ | Br |
| c-Pr | CF₃ | Br | c-Pr | CF₃ | Br |
| c-PrCH₂ | CF₃ | Br | c-PrCH₂ | CF₃ | Br |
| 1,1'-bicyclopropyl-2-yl | CF₃ | Br | 1,1'-bicyclopropyl-2-yl | CF₃ | Br |
| $R^2$ is Me, X is Br, $R^{13}$ is F and Z is N. | | | $R^2$ is Cl, X is Br, $R^{13}$ is F and Z is N. | | |
| Me | OCH₂CF₃ | F | Me | OCH₂CF₃ | F |
| Et | OCH₂CF₃ | F | Et | OCH₂CF₃ | F |
| c-Pr | OCH₂CF₃ | Cl | c-Pr | OCH₂CF₃ | Cl |
| c-PrCH₂ | OCH₂CF₃ | Cl | c-PrCH₂ | OCH₂CF₃ | Cl |
| 1,1'-bicyclopropyl-1-yl | OCH₂CF₃ | Cl | 1,1'-bicyclopropyl-1-yl | OCH₂CF₃ | Cl |
| Me | OCH₂CF₃ | Br | Me | OCH₂CF₃ | Br |
| Et | OCH₂CF₃ | Br | Et | OCH₂CF₃ | Br |
| Me | OCF₂H | F | Me | OCF₂H | F |
| Et | OCF₂H | F | Et | OCF₂H | F |
| c-Pr | OCF₂H | Cl | c-Pr | OCF₂H | Cl |
| c-PrCH₂ | OCF₂H | Cl | c-PrCH₂ | OCF₂H | Cl |
| 1,1'-bicyclopropyl-1-yl | OCF₂H | Cl | 1,1'-bicyclopropyl-1-yl | OCF₂H | Cl |
| Me | OCF₂H | Br | Me | OCF₂H | Br |
| Et | OCF₂H | Br | Et | OCF₂H | Br |
| $R^2$ is Me, X is Br, $R^{13}$ is Cl and Z is N. | | | $R^2$ is Cl, X is Br, $R^{13}$ is Cl and Z is N. | | |
| H | Br | F | H | Br | F |
| Me | Br | F | Me | Br | F |
| t-Bu | Br | F | t-Bu | Br | F |
| c-Pr | Br | F | c-Pr | Br | F |
| c-PrCH₂ | Br | F | c-PrCH₂ | Br | F |
| 1,1'-bicyclopropyl-2-yl | Br | F | 1,1'-bicyclopropyl-2-yl | Br | F |
| 1,1'-bicyclopropyl-1-yl | Br | F | 1,1'-bicyclopropyl-1-yl | Br | F |
| H | Br | Cl | H | Br | Cl |
| Me | Br | Cl | Me | Br | Cl |
| t-Bu | Br | Cl | t-Bu | Br | Cl |
| c-Pr | Br | Cl | c-Pr | Br | Cl |
| c-PrCH₂ | Br | Cl | c-PrCH₂ | Br | Cl |
| 1,1'-bicyclopropyl-2-yl | Br | Cl | 1,1'-bicyclopropyl-2-yl | Br | Cl |
| (1R,2S)-1,1'-bicyclopropyl-2-yl | Br | Cl | (1R,2S)-1,1'-bicyclopropyl-2-yl | Br | Cl |
| H | Br | Br | H | Br | Br |
| Me | Br | Br | Me | Br | Br |
| t-Bu | Br | Br | t-Bu | Br | Br |
| c-Pr | Br | Br | c-Pr | Br | Br |
| c-PrCH₂ | Br | Br | c-PrCH₂ | Br | Br |
| $R^2$ is Me, X is Br, $R^{13}$ is Cl and Z is N. | | | $R^2$ is Cl, X is Br, $R^{13}$ is Cl and Z is N. | | |
| 1,1'-bicyclopropyl-1-yl | Br | Br | 1,1'-bicyclopropyl-1-yl | Br | Br |
| (1R,2R)-1,1'-bicyclopropyl-2-yl | Br | Br | (1R,2R)-1,1'-bicyclopropyl-2-yl | Br | Br |
| H | Cl | F | H | Cl | F |
| Me | Cl | F | Me | Cl | F |
| t-Bu | Cl | F | t-Bu | Cl | F |
| c-Pr | Cl | F | c-Pr | Cl | F |
| c-PrCH₂ | Cl | F | c-PrCH₂ | Cl | F |
| 1,1'-bicyclopropyl-2-yl | Cl | F | 1,1'-bicyclopropyl-2-yl | Cl | F |
| H | Cl | Cl | H | Cl | Cl |
| Me | Cl | Cl | Me | Cl | Cl |
| t-Bu | Cl | Cl | t-Bu | Cl | Cl |
| c-Pr | Cl | Cl | c-Pr | Cl | Cl |
| c-PrCH₂ | Cl | Cl | c-PrCH₂ | Cl | Cl |
| 1,1'-bicyclopropyl-2-yl | Cl | Cl | 1,1'-bicyclopropyl-2-yl | Cl | Cl |
| 1,1'-bicyclopropyl-1-yl | Cl | Cl | 1,1'-bicyclopropyl-1-yl | Cl | Cl |
| H | Cl | Br | H | Cl | Br |
| Me | Cl | Br | Me | Cl | Br |
| t-Bu | Cl | Br | t-Bu | Cl | Br |
| c-Pr | Cl | Br | c-Pr | Cl | Br |
| c-PrCH₂ | Cl | Br | c-PrCH₂ | Cl | Br |
| 1,1'-bicyclopropyl-2-yl | Cl | Br | 1,1'-bicyclopropyl-2-yl | Cl | Br |
| 1,1'-bicyclopropyl-1-yl | Cl | Br | 1,1'-bicyclopropyl-1-yl | Cl | Br |
| H | CF₃ | F | H | CF₃ | F |
| Me | CF₃ | F | Me | CF₃ | F |
| t-Bu | CF₃ | F | t-Bu | CF₃ | F |

TABLE 2-continued

| | | | | | |
|---|---|---|---|---|---|
| 2-CH₃-c-Pr | CF₃ | F | c-Pr | CF₃ | F |
| 1,1'-bicyclopropyl-2-yl | CF₃ | F | 1,1'-bicyclopropyl-2-yl | CF₃ | F |
| 1,1'-bicyclopropyl-1-yl | CF₃ | F | 1,1'-bicyclopropyl-1-yl | CF₃ | F |
| H | CF₃ | Cl | H | CF₃ | Cl |
| Me | CF₃ | Cl | Me | CF₃ | Cl |
| t-Bu | CF₃ | Cl | t-Bu | CF₃ | Cl |
| Me | CF₃ | Br | Me | CF₃ | Br |
| Et | CF₃ | Br | Et | CF₃ | Br |
| c-Pr | CF₃ | Br | c-Pr | CF₃ | Br |
| c-PrCH₂ | CF₃ | Br | c-PrCH₂ | CF₃ | Br |
| 1,1'-bicyclopropyl-2-yl | CF₃ | Br | 1,1'-bicyclopropyl-2-yl | CF₃ | Br |
| $R^2$ is Me, X is Br, $R^{13}$ is Cl and Z is N. | | | $R^2$ is Cl, X is Br, $R^{13}$ is Cl and Z is N. | | |
| Me | OCH₂CF₃ | F | Me | OCH₂CF₃ | F |
| Et | OCH₂CF₃ | F | Et | OCH₂CF₃ | F |
| c-Pr | OCH₂CF₃ | Cl | c-Pr | OCH₂CF₃ | Cl |
| c-PrCH₂ | OCH₂CF₃ | Cl | c-PrCH₂ | OCH₂CF₃ | Cl |
| 1,1'-bicyclopropyl-1-yl | OCH₂CF₃ | Cl | 1,1'-bicyclopropyl-1-yl | OCH₂CF₃ | Cl |
| Me | OCH₂CF₃ | Br | Me | OCH₂CF₃ | Br |
| Et | OCH₂CF₃ | Br | Et | OCH₂CF₃ | Br |
| Me | OCF₂H | F | Me | OCF₂H | F |
| Et | OCF₂H | F | Et | OCF₂H | F |
| c-Pr | OCF₂H | Cl | c-Pr | OCF₂H | Cl |
| c-PrCH₂ | OCF₂H | Cl | c-PrCH₂ | OCF₂H | Cl |
| 1,1'-bicyclopropyl-2-yl | OCF₂H | F | 1,1'-bicyclopropyl-2-yl | OCF₂H | F |
| Me | OCF₂H | Br | Me | OCF₂H | Br |
| Et | OCF₂H | Br | Et | OCF₂H | Br |
| $R^2$ is Me, X is Cl, $R^{13}$ is H and Z is N. | | | $R^2$ is Me, X is Cl, $R^{13}$ is H and Z is N. | | |
| H | Br | F | H | Br | Cl |
| Me | Br | F | Me | Br | Cl |
| Et | Br | F | Et | Br | Cl |
| n-Pr | Br | F | n-Pr | Br | Cl |
| i-Pr | Br | F | i-Pr | Br | Cl |
| n-Bu | Br | F | n-Bu | Br | Cl |
| i-Bu | Br | F | i-Bu | Br | Cl |
| s-Bu | Br | F | s-Bu | Br | Cl |
| t-Bu | Br | F | t-Bu | Br | Cl |
| c-Pr | Br | F | c-Pr | Br | Cl |
| c-PrCH₂ | Br | F | c-PrCH₂ | Br | Cl |
| 1-CH₃-c-Pr | Br | F | 1-CH₃-c-Pr | Br | Cl |
| 2-CH₃-c-Pr | Br | F | 2-CH₃-c-Pr | Br | Cl |
| 1,1'-bicyclopropyl-2-yl | Br | F | 1,1'-bicyclopropyl-2-yl | Br | Cl |
| 1,1'-bicyclopropyl-1-yl | Br | F | 1,1'-bicyclopropyl-1-yl | Br | Cl |
| (1R,2S)-1,1'-bicyclopropyl-2-yl | Br | F | (1R,2R)-1,1'-bicyclopropyl-2-yl | Br | Cl |
| H | Br | Br | H | Cl | F |
| Me | Br | Br | Me | Cl | F |
| Et | Br | Br | Et | Cl | F |
| $R^2$ is Me, X is Cl, $R^{13}$ is H and Z is N. | | | $R^2$ is Me, X is Cl, $R^{13}$ is H and Z is N. | | |
| n-Pr | Br | Br | n-Pr | Cl | F |
| i-Pr | Br | Br | i-Pr | Cl | F |
| n-Bu | Br | Br | n-Bu | Cl | F |
| i-Bu | Br | Br | i-Bu | Cl | F |
| s-Bu | Br | Br | s-Bu | Cl | F |
| t-Bu | Br | Br | t-Bu | Cl | F |
| c-Pr | Br | Br | c-Pr | Cl | F |
| c-PrCH₂ | Br | Br | c-PrCH₂ | Cl | F |
| 1-CH₃-c-Pr | Br | Br | 1-CH₃-c-Pr | Cl | F |
| 2-CH₃-c-Pr | Br | Br | 2-CH₃-c-Pr | Cl | F |
| 1,1'-bicyclopropyl-2-yl | Br | Br | 1,1'-bicyclopropyl-2-yl | Cl | F |
| 1,1'-bicyclopropyl-1-yl | Br | Br | 1,1'-bicyclopropyl-1-yl | Cl | F |
| (1S,2R)-1,1'-bicyclopropyl-2-yl | Br | Br | (1S,2R)-1,1'-bicyclopropyl-2-yl | Cl | F |
| H | Cl | Cl | H | Cl | Br |
| Me | Cl | Cl | Me | Cl | Br |
| Et | Cl | Cl | Et | Cl | Br |
| n-Pr | Cl | Cl | n-Pr | Cl | Br |
| i-Pr | Cl | Cl | i-Pr | Cl | Br |
| n-Bu | Cl | Cl | n-Bu | Cl | Br |
| i-Bu | Cl | Cl | i-Bu | Cl | Br |
| s-Bu | Cl | Cl | s-Bu | Cl | Br |
| t-Bu | Cl | Cl | t-Bu | Cl | Br |
| c-Pr | Cl | Cl | c-Pr | Cl | Br |
| c-PrCH₂ | Cl | Cl | c-PrCH₂ | Cl | Br |
| 1-CH₃-c-Pr | Cl | Cl | 1-CH₃-c-Pr | Cl | Br |
| 2-CH₃-c-Pr | Cl | Cl | 2-CH₃-c-Pr | Cl | Br |
| 1,1'-bicyclopropyl-2-yl | Cl | Cl | 1,1'-bicyclopropyl-2-yl | Cl | Br |
| 1,1'-bicyclopropyl-1-yl | Cl | Cl | 1,1'-bicyclopropyl-1-yl | Cl | Br |
| (1R,2R)-1,1'-bicyclopropyl-2-yl | Cl | Cl | (1R,2R)-1,1'-bicyclopropyl-2-yl | Cl | Br |
| H | CF₃ | F | H | CF₃ | Cl |

TABLE 2-continued

| | | |
|---|---|---|
| Me | CF₃ | F |
| t-Bu | CF₃ | F |
| 1-CH₃-c-Pr | CF₃ | F |
| 2-CH₃-c-Pr | CF₃ | F |
| 1,1'-bicyclopropyl-1-yl | CF₃ | F |
| (1R,2S)-1,1'-bicyclopropyl-2-yl | CF₃ | F |
| Me | CF₃ | Cl |
| t-Bu | CF₃ | Cl |
| 1-CH₃-c-Pr | CF₃ | Cl |
| 2-CH₃-c-Pr | CF₃ | Cl |
| 1,1'-bicyclopropyl-2-yl | CF₃ | Cl |
| 1,1'-bicyclopropyl-1-yl | CF₃ | Cl |

R² is Me, X is Cl, R¹³ is H and Z is N.

| | | |
|---|---|---|
| H | CF₃ | Br |
| Me | CF₃ | Br |
| t-Bu | CF₃ | Br |
| 1-CH₃-c-Pr | CF₃ | Br |
| 2-CH₃-c-Pr | CF₃ | Br |
| 1,1'-bicyclopropyl-1-yl | CF₃ | Br |
| H | OCF₂H | F |
| Me | OCF₂H | F |
| t-Bu | OCF₂H | F |
| 1,1'-bicyclopropyl-1-yl | OCF₂H | F |
| H | OCF₂H | Cl |
| Me | OCF₂H | Cl |
| t-Bu | OCF₂H | Cl |
| 1,1'-bicyclopropyl-2-yl | OCF₂H | Cl |
| H | OCF₂H | Br |
| Me | OCF₂H | Br |
| H | OCH₂CF₃ | F |
| Me | OCH₂CF₃ | F |
| t-Bu | OCH₂CF₃ | F |
| 1-CH₃-c-Pr | OCH₂CF₃ | F |
| 1,1'-bicyclopropyl-1-yl | OCH₂CF₃ | F |
| H | OCH₂CF₃ | Cl |
| Me | OCH₂CF₃ | Cl |
| t-Bu | OCH₂CF₃ | Cl |
| 2-CH₃-c-Pr | OCH₂CF₃ | Cl |
| 1,1'-bicyclopropyl-1-yl | OCH₂CF₃ | Cl |
| H | OCH₂CF₃ | Br |
| Me | OCH₂CF₃ | Br |
| t-Bu | OCH₂CF₃ | Br |
| 1-CH₃-c-Pr | OCH₂CF₃ | Br |
| 1,1'-bicyclopropyl-2-yl | OCH₂CF₃ | Br |
| t-Bu | OCF₂H | Br |

R² is Me, X is Cl, R¹³ is H and Z is CH.

| | | |
|---|---|---|
| H | Br | F |
| Me | Br | F |
| t-Bu | Br | F |
| c-Pr | Br | F |
| c-PrCH₂ | Br | F |
| 1,1'-bicyclopropyl-2-yl | Br | F |
| 1,1'-bicyclopropyl-1-yl | Br | F |
| (1R,2S)-1,1'-bicyclopropyl-2-yl | Br | F |
| (1R,2R)-1,1'-bicyclopropyl-2-yl | Br | F |
| H | Br | Br |
| Me | Br | Br |
| t-Bu | Br | Br |
| c-Pr | Br | Br |
| c-PrCH₂ | Br | Br |
| 1,1'-bicyclopropyl-2-yl | Br | Br |
| 1,1'-bicyclopropyl-1-yl | Br | Br |
| (1R,2R)-1,1'-bicyclopropyl-2-yl | Br | Br |
| H | Br | Cl |
| Me | Br | Cl |
| t-Bu | Br | Cl |
| c-Pr | Br | Cl |
| c-PrCH₂ | Br | Cl |
| 1,1'-bicyclopropyl-2-yl | Br | Cl |
| 1,1'-bicyclopropyl-1-yl | Br | Cl |
| (1R,2S)-1,1'-bicyclopropyl-2-yl | Br | Cl |
| (1R,2R)-1,1'-bicyclopropyl-2-yl | Br | Cl |
| H | Cl | F |
| Me | Cl | F |
| t-Bu | Cl | F |
| c-Pr | Cl | F |
| c-PrCH₂ | Cl | F |
| 1,1'-bicyclopropyl-2-yl | Cl | F |
| 1,1'-bicyclopropyl-1-yl | Cl | F |
| (1R,2R)-1,1'-bicyclopropyl-2-yl | Cl | F |

R² is Me, X is Cl, R¹³ is H and Z is CH.

| | | |
|---|---|---|
| H | Cl | Cl |
| Me | Cl | Cl |
| t-Bu | Cl | Cl |
| c-Pr | Cl | Cl |
| c-PrCH₂ | Cl | Cl |
| 1,1'-bicyclopropyl-2-yl | Cl | Cl |
| 1,1'-bicyclopropyl-1-yl | Cl | Cl |
| (1S,2R)-1,1'-bicyclopropyl-2-yl | Cl | Cl |
| H | CF₃ | F |
| Me | CF₃ | F |
| t-Bu | CF₃ | F |
| 2-CH₃-c-Pr | CF₃ | F |
| 1,1'-bicyclopropyl-2-yl | CF₃ | F |
| Me | OCH₂CF₃ | F |
| Et | OCH₂CF₃ | F |
| c-Pr | OCH₂CF₃ | F |
| Me | OCH₂CF₃ | Cl |
| c-PrCH₂ | OCH₂CF₃ | Cl |
| 1,1'-bicyclopropyl-1-yl | OCH₂CF₃ | Cl |
| Me | OCH₂CF₃ | Br |
| Et | OCH₂CF₃ | Br |
| Et | OCH₂CF₃ | Br |
| c-Pr | OCH₂CF₃ | Br |
| H | Cl | Br |
| Me | Cl | Br |
| t-Bu | Cl | Br |
| c-Pr | Cl | Br |
| c-PrCH₂ | Cl | Br |
| 1,1'-bicyclopropyl-2-yl | Cl | Br |
| 1,1'-bicyclopropyl-1-yl | Cl | Br |
| (1S,2R)-1,1'-bicyclopropyl-2-yl | Cl | Br |
| H | CF₃ | Cl |
| Me | CF₃ | Cl |
| t-Bu | CF₃ | Cl |
| Me | CF₃ | Cl |
| Et | CF₃ | Br |
| c-Pr | CF₃ | Br |
| c-PrCH₂ | CF₃ | Br |
| 1,1'-bicyclopropyl-1-yl | CF₃ | Br |
| Me | OCF₂H | F |
| Et | OCF₂H | F |
| c-Pr | OCF₂H | Cl |
| c-PrCH₂ | OCF₂H | Cl |
| 1,1'-bicyclopropyl-1-yl | OCF₂H | Cl |
| Me | OCF₂H | Br |
| Et | OCF₂H | Br |

R² is Me, X is Cl, R¹³ is F and Z is N.

| | | |
|---|---|---|
| H | Br | F |
| Me | Br | F |
| t-Bu | Br | F |
| c-Pr | Br | F |
| c-PrCH₂ | Br | F |
| 1,1'-bicyclopropyl-2-yl | Br | F |
| 1,1'-bicyclopropyl-1-yl | Br | F |
| H | Br | Br |
| Me | Br | Br |
| t-Bu | Br | Br |
| H | Br | Cl |
| Me | Br | Cl |
| t-Bu | Br | Cl |
| c-Pr | Br | Cl |
| c-PrCH₂ | Br | Cl |
| 1,1'-bicyclopropyl-2-yl | Br | Cl |
| 1,1'-bicyclopropyl-1-yl | Br | Cl |
| H | Cl | F |
| Me | Cl | F |
| t-Bu | Cl | F |

TABLE 2-continued

| $R^2$ is Me, X is Cl, $R^{13}$ is F and Z is N. | | | $R^2$ is Me, X is Cl, $R^{13}$ is F and Z is N. | | |
|---|---|---|---|---|---|
| c-Pr | Br | Br | c-Pr | Cl | F |
| c-PrCH$_2$ | Br | Br | c-PrCH$_2$ | Cl | F |
| 1,1'-bicyclopropyl-2-yl | Br | Br | 1,1'-bicyclopropyl-1-yl | Cl | F |
| (1R,2S)-1,1'-bicyclopropyl-2-yl | Br | Br | (1R,2S)-1,1'-bicyclopropyl-2-yl | Cl | F |
| H | Cl | Cl | H | Cl | Br |
| Me | Cl | Cl | Me | Cl | Br |
| t-Bu | Cl | Cl | t-Bu | Cl | Br |
| c-Pr | Cl | Cl | c-Pr | Cl | Br |
| c-PrCH$_2$ | Cl | Cl | c-PrCH$_2$ | Cl | Br |
| 1,1'-bicyclopropyl-2-yl | Cl | Cl | 1,1'-bicyclopropyl-2-yl | Cl | Br |
| 1,1'-bicyclopropyl-1-yl | Cl | Cl | 1,1'-bicyclopropyl-1-yl | Cl | Br |
| H | CF$_3$ | F | Me | OCH$_2$CF$_3$ | F |
| Me | CF$_3$ | F | Et | OCH$_2$CF$_3$ | F |
| t-Bu | CF$_3$ | F | c-Pr | OCH$_2$CF$_3$ | Cl |
| 2-CH$_3$-c-Pr | CF$_3$ | F | c-PrCH$_2$ | OCH$_2$CF$_3$ | Cl |
| 1,1'-bicyclopropyl-2-yl | CF$_3$ | F | 1,1'-bicyclopropyl-1-yl | OCH$_2$CF$_3$ | Cl |
| H | CF$_3$ | Cl | Me | OCH$_2$CF$_3$ | Br |
| Me | CF$_3$ | Cl | Et | OCH$_2$CF$_3$ | Br |
| t-Bu | CF$_3$ | Cl | Me | OCF$_2$H | F |
| c-Pr | CF$_3$ | Cl | Et | OCF$_2$H | F |
| Me | CF$_3$ | Br | c-Pr | OCF$_2$H | Cl |
| Et | CF$_3$ | Br | c-PrCH$_2$ | OCF$_2$H | Cl |
| c-Pr | CF$_3$ | Br | 1,1'-bicyclopropyl-2-yl | OCF$_2$H | Cl |
| c-PrCH$_2$ | CF$_3$ | Br | Me | OCF$_2$H | Br |
| 1,1'-bicyclopropyl-1-yl | CF$_3$ | Br | Et | OCF$_2$H | Br |
| $R^2$ is Me, X is Cl, $R^{13}$ is Cl and Z is N. | | | $R^2$ is Me, X is Cl, $R^{13}$ is Cl and Z is N. | | |
| H | Br | F | H | Br | Cl |
| Me | Br | F | Me | Br | Cl |
| t-Bu | Br | F | t-Bu | Br | Cl |
| c-Pr | Br | F | c-Pr | Br | Cl |
| c-PrCH$_2$ | Br | F | c-PrCH$_2$ | Br | Cl |
| 1,1'-bicyclopropyl-2-yl | Br | F | 1,1'-bicyclopropyl-2-yl | Br | Cl |
| 1,1'-bicyclopropyl-1-yl | Br | F | (1R,2S)-1,1'-bicyclopropyl-2-yl | Br | Cl |
| H | Br | Br | H | Cl | F |
| $R^2$ is Me, X is Cl, $R^{13}$ is Cl and Z is N. | | | $R^2$ is Me, X is Cl, $R^{13}$ is Cl and Z is N. | | |
| Me | Br | Br | Me | Cl | F |
| t-Bu | Br | Br | t-Bu | Cl | F |
| c-Pr | Br | Br | c-Pr | Cl | F |
| c-PrCH$_2$ | Br | Br | c-PrCH$_2$ | Cl | F |
| 1,1'-bicyclopropyl-1-yl | Br | Br | 1,1'-bicyclopropyl-2-yl | Cl | F |
| (1R,2R)-1,1'-bicyclopropyl-2-yl | Br | Br | (1R,2R)-1,1'-bicyclopropyl-2-yl | Cl | F |
| H | Cl | Br | H | Cl | Cl |
| Me | Cl | Br | Me | Cl | Cl |
| t-Bu | Cl | Br | t-Bu | Cl | Cl |
| c-Pr | Cl | Br | c-Pr | Cl | Cl |
| c-PrCH$_2$ | Cl | Br | c-PrCH$_2$ | Cl | Cl |
| 1,1'-bicyclopropyl-2-yl | Cl | Br | 1,1'-bicyclopropyl-2-yl | Cl | Cl |
| 1,1'-bicyclopropyl-1-yl | Cl | Br | 1,1'-bicyclopropyl-1-yl | Cl | Cl |
| H | CF$_3$ | F | Me | OCH$_2$CF$_3$ | F |
| Me | CF$_3$ | F | Et | OCH$_2$CF$_3$ | F |
| t-Bu | CF$_3$ | F | c-Pr | OCH$_2$CF$_3$ | Cl |
| 2-CH$_3$-c-Pr | CF$_3$ | F | c-PrCH$_2$ | OCH$_2$CF$_3$ | Cl |
| 1,1'-bicyclopropyl-2-yl | CF$_3$ | F | 1,1'-bicyclopropyl-1-yl | OCH$_2$CF$_3$ | Cl |
| 1,1'-bicyclopropyl-1-yl | CF$_3$ | F | Me | OCH$_2$CF$_3$ | Br |
| H | CF$_3$ | Cl | Et | OCH$_2$CF$_3$ | Br |
| Me | CF$_3$ | Cl | Me | OCF$_2$H | F |
| t-Bu | CF$_3$ | Cl | Et | OCF$_2$H | F |
| Me | CF$_3$ | Br | c-Pr | OCF$_2$H | Cl |
| Et | CF$_3$ | Br | c-PrCH$_2$ | OCF$_2$H | Cl |
| c-Pr | CF$_3$ | Br | 1,1'-bicyclopropyl-2-yl | OCF$_2$H | F |
| c-PrCH$_2$ | CF$_3$ | Br | Me | OCF$_2$H | Br |
| 1,1'-bicyclopropyl-1-yl | CF$_3$ | Br | Et | OCF$_2$H | Br |

The present disclosure includes Table 3 which is constructed the same as above Table 2 except that the compound of Formula 3 of Table 2 (i.e. 1-methyl-1H-imidazole) is replaced with 1-butyl-1H-imidazole (i.e. $R^5$ is n-Bu, $R^6$, $R^7$ and $R^8$ are H) in Table 3. $R^2$, $R^3$, $R^{11}$, $R^{12}$ and $R^{13}$ in Table 3 are as listed in Table 2.

What is claimed is:

1. A method for preparing a compound of Formula 1

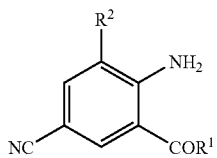

wherein
$R^1$ is $NHR^3$;
$R^2$ is $CH_3$ or Cl; and
$R^3$ is H, $C_1$-$C_4$ alkyl, cyclopropyl, cyclopropylcyclopropyl, cyclopropylmethyl or methylcyclopropyl;
comprising contacting (1) a compound of Formula 2

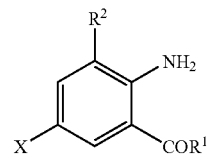

wherein X is Br or Cl;
with (2) a metal cyanide reagent comprising one or more compounds selected from the group consisting of alkali metal cyanides and copper(I) cyanide, (3) a copper(I) salt reagent, (4) an iodide salt reagent and (5) at least one compound of Formula 3

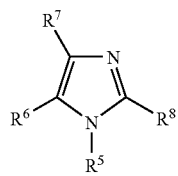

wherein
$R^5$ is H, phenyl or benzyl; or $C_1$-$C_{12}$ alkyl optionally substituted with $NR^9R^{10}$;
each $R^6$, $R^7$ and $R^8$ is independently H, $C_1$-$C_{12}$ alkyl, phenyl or benzyl; or
$R^6$ and $R^7$ are taken together as —CH=CH—CH=CH—; and
$R^9$ and $R^{10}$ are taken together as —CH=N—CH=CH— optionally substituted with up to 3 substituents independently selected from $C_1$-$C_{12}$ alkyl;
provided that when X is Cl, then $R^2$ is methyl.

2. The method of claim 1 wherein the copper(I) salt reagent and the iodide salt reagent comprise copper(I) iodide.

3. The method of claim 1 wherein the at least one compound of Formula 3 comprises one or more compounds selected from the group consisting of 1-methyl-1H-imidazole, 1-ethyl-1H-imidazole, 1-propyl-1H-imidazole, 1-butyl-1H-imidazole, 1-pentyl-1H-imidazole, 1-hexyl-1H-imidazole, 4-methylimidazole, 1,1'-(1,4-butanediyl)bis-1H-imidazole, 1,1'-(1,5-pentanediyl)bis-1H-imidazole and 1,1'-(1,6-hexanediyl)bis-1H-imidazole.

4. The method of claim 3 wherein the at least one compound of Formula 3 comprises one or more compounds selected from the group consisting of 1-methyl-1H-imidazole, 1-butyl-1H-imidazole, 4-methylimidazole and 1,1'-(1,6-hexanediyl)bis-1H-imidazole.

5. The method of claim 4 wherein the at least one compound of Formula 3 comprises 1-methyl-1H-imidazole or 1-butyl-1H-imidazole.

6. The method of claim 1 wherein the compound of Formula 2 is contacted with a suitable organic solvent to form a mixture, and then the metal cyanide reagent, the copper(I) salt reagent, the iodide salt reagent and the at least one compound of Formula 3 are sequentially added to the mixture.

7. The method of claim 6 wherein the suitable organic solvent comprises one or more solvents selected from the group consisting of xylenes, toluene, chlorobenzene, methoxybenzene, 1,2,4-trimethylbenzene, 1,3,5-trimethylbenzene, ethylbenzene, (1-methylethyl)benzene, $C_1$-$C_3$ alkyl-substituted naphthalenes, ShellSol A100 and ShellSol A150.

8. The method of claim 7 wherein the suitable organic solvent comprises one or more solvents selected from the group consisting of xylenes, toluene, 1,2,4-trimethylbenzene, 1,3,5-trimethylbenzene and 1-methylnaphthalene.

9. The method of claim 1 wherein the metal cyanide reagent comprises one or more compounds selected from the group consisting of sodium cyanide and potassium cyanide.

10. The method of claim 9 wherein the metal cyanide reagent comprises sodium cyanide.

11. The method of claim 1 wherein X is Br and the compound of Formula 1 is prepared as a solid comprising: contacting a compound of Formula 2 with a suitable organic solvent to form a mixture, and then sequentially adding the metal cyanide reagent, the copper(I) salt reagent, the iodide salt reagent and the compound or compounds of Formula 3, maintaining the temperature of the mixture between about 145 and 180° C. for about 5 to about 8 h, cooling the mixture to between about 0 and 50° C., adding water to the mixture, optionally stirring for about 1 to about 24 h, and then recovering a compound of Formula 1 as a solid from the mixture.

12. The method of claim 11 wherein the compound of Formula 1 is 2-amino-5-cyano-N,3-dimethylbenzamide.

13. The method of claim 1 wherein X is Cl and the compound of Formula 1 is prepared as a solid comprising contacting a compound of Formula 2 with a suitable organic solvent to form a mixture, and then sequentially adding the metal cyanide reagent, the copper(I) salt reagent, the iodide salt reagent and the compound or compounds of Formula 3, maintaining the temperature of the mixture between about 150 and 200° C. for about 5 to about 24 h, cooling the mixture to between about 0 and 50° C., adding water to the mixture, optionally stirring for about 1 to about 24 h, and then recovering a compound of Formula 1 as a solid from the mixture.

14. The method of claim 13 wherein the compound of Formula 1 is 2-amino-5-cyano-N,3-dimethylbenzamide.

* * * * *